US012790577B2

(12) United States Patent
Trunfio et al.

(10) Patent No.: US 12,790,577 B2
(45) Date of Patent: Nov. 10, 2026

(54) MONITORING AND CONTROL OF BIOPROCESSES

(71) Applicant: Sartorius Stedim Data Analytics AB, Umeå (SE)

(72) Inventors: Nicholas Trunfio, Billerica, MA (US); Christopher Peter McCready, London (CA)

(73) Assignee: Sartorius Stedim Data Analytics AB, Umeå (SE)

( * ) Notice: Subject to any disclaimer, the term of this patent is extended or adjusted under 35 U.S.C. 154(b) by 492 days.

(21) Appl. No.: 18/027,045

(22) PCT Filed: Sep. 9, 2021

(86) PCT No.: PCT/EP2021/074866
§ 371 (c)(1),
(2) Date: Mar. 17, 2023

(87) PCT Pub. No.: WO2022/069180
PCT Pub. Date: Apr. 7, 2022

(65) Prior Publication Data
US 2023/0323275 A1 Oct. 12, 2023

(30) Foreign Application Priority Data
Oct. 2, 2020 (EP) .................................... 20199899

(51) Int. Cl.
*C12M 1/34* (2006.01)
*C12M 1/36* (2006.01)

(52) U.S. Cl.
CPC ............ *C12M 41/36* (2013.01); *C12M 41/38* (2013.01); *C12M 41/48* (2013.01)

(58) Field of Classification Search
CPC ...... C12M 41/36; C12M 41/38; C12M 41/48; G16B 40/00; H04B 7/0641; H04B 7/0658;
(Continued)

(56) References Cited

U.S. PATENT DOCUMENTS

2016/0152936 A1 6/2016 Bargh et al.

FOREIGN PATENT DOCUMENTS

EP 3 291 038 A1 3/2018
WO WO 2014/020327 A1 2/2014
(Continued)

OTHER PUBLICATIONS

International Search Report and Written Opinion for International Application No. PCT/EP2021/074866 mailed Dec. 6, 2021.
(Continued)

*Primary Examiner* — Lydia Edwards
(74) *Attorney, Agent, or Firm* — Wolf, Greenfield & Sacks, P.C.

(57) ABSTRACT

A computer implemented method for monitoring a bioprocess comprising a cell culture in a bioreactor is provided. The method including the steps of: obtaining measurements of the amount of biomass and the amount of one or more metabolites in the bioreactor as a function of bioprocess maturity, using the measurements to determining one or more metabolic condition variables; using a pre-trained multivariate model to determine the value of one or more latent variables as a function of bioprocess maturity, wherein the multivariate model is a linear model that uses process variables including the metabolic condition variables as predictor variables and maturity as a response variable; comparing the value(s) of the one or more latent variables to one or more predetermined values as a function of maturity;
(Continued)

and determining on the basis of the comparison whether the bioprocess is operating normally.

19 Claims, 43 Drawing Sheets

(58) Field of Classification Search
CPC ... H04B 7/0663; H04B 7/0639; G05B 13/048
See application file for complete search history.

(56) References Cited

FOREIGN PATENT DOCUMENTS

| | | |
|---|---|---|
| WO | WO 2019/129891 A1 | 7/2019 |
| WO | WO 2020/120232 A1 | 6/2020 |

OTHER PUBLICATIONS

Gao et al., Multivariate Analysis of Cell Culture Bioprocess Data. American Pharmaceutical Review. Apr. 2020:78-82.

Solle et al., Between the poles of data-driven and mechanistic modeling for process operation. Chemie Ingenieur Technik. May 2017;89(5):542-61.

[No Author Listed], *SIMCA 15 User Guide*. Sartorius Stedim Data Analytics AB. Guide edition date: Jun. 10, 2020. pp. 1-100.

[No Author Listed], Metabolic flux analysis. Wikipedia.Aug. 16, 2020. 2 Pages.

Karra et al., Mutli-Scale Modeling of Heterogeneities in Mammalian Cell Culture Processes. Ind. Eng. Chem. Res. 2010.49(17): 7990-8006.

Kyriakopoulos et al, A framework for the systematic design of fed-batch strategies in mammalian cell culture. Biotechnology and bioengineering 111.12 (2014): 2466-2476.

Lee et al., Intracellular metabolic flux analysis of CHO cells supplemented with wheat hydrolysates for improved mAb production and cell-growth. Wiley Online Library. Sep. 29, 2014. 12 Pages.

Lopez-Meza et al., Using simple models to describe the kinetics of growth, glucose consumption, and monoclonal antibody formation in naive and infliximab producer CHO cells. Cytotechnology. 2016. 68:1287-1300.

Mesquita et al., Metabolic fluxes-oriented control of bioreactors: a novel approach to tune micro-aeration and substrate feeding in fermentations. Microbial Cell Factories. 2019. 18:150. 17 pages.

Mesquita et al., Metabolic fluxes-oriented control of bioreactors: a novel approach to tune micro-aeration and substrate feeding in fermentations. Additional Files 1. 2019. 12 Pages.

Orth et al., What is flux balance analysis? Computational Biology. Nature Biotechnology. Mar. 2010. 28(3):245-8.

Popp et al., A Hybrid Approach Identifies Metabolic Signatures of High-Producers for Chinese Hamster Ovary Clone Selection and Process Optimization. Systems Biotechnology. Biotechnology and Bioengineering. Aug. 20, 2015. 37 Pages.

Monitoring

C

D

C

D

E

F

C

D

B e)

e)

a)

b)

MONITORING AND CONTROL OF BIOPROCESSES

CROSS REFERENCE TO RELATED APPLICATIONS

This application is a national stage filing under 35 U.S.C. § 371 of international application number PCT/EP2021/074866, filed Sep. 9, 2021, which claims the benefit of European application number EP 20199899.4, filed Oct. 2, 2020, each of which is incorporated by reference herein in its entirety.

FIELD OF THE PRESENT DISCLOSURE

The present disclosure relates to computer implemented methods, computer programs and systems for the monitoring and control of bioprocesses. Particular methods, programs and systems of the disclosure use multivariate models including one or more variables representative of the metabolic condition of cells in a bioprocess.

BACKGROUND

Upstream bioprocesses use living organisms, such as CHO (Chinese Hamster Ovary) or *E. coli* cells, to produce a desired product, for example a substance with therapeutic effects (e.g. monoclonal antibodies, mAbs). Therapeutic effects of such products are dictated by aspects of their molecular structure, such as e.g. glycosylation profiles (particularly in the case of mAbs). These aspects are collectively referred to as "critical quality attributes" (CQAs). In order to market biological products, biomanufacturers are often required to prove to regulatory agencies that they can reliably operate their process in a consistent manner, such that the CQAs are guaranteed to meet specification by virtue of the way the process was run. Statistical process analysis methods, including univariate batch process analysis and multivariate statistical analysis, can be used to assess satisfactory performance of a bioprocess. In particular, multivariate statistical models (including principal component analysis—PCA—and (orthogonal) partial least square regression—(O)PLS) have become a popular tool for identifying process conditions that are important to ensure that CQAs are within specification (collectively referred to as "critical process parameters", CPPs) and to establish acceptable ranges of these process conditions as a bioprocess progresses to completion. Such tools have been implemented in the Umetrics® software suite (Sartorius Stedim Data Analytics), which is a leading data analytics software for modelling and optimizing biopharmaceutical development and manufacturing processes.

In a typical bioprocess analysis, a series of process variables (e.g. a few dozen process variables including temperature, concentration of key nutrients and metabolites, pH, volume, gas concentrations, viable cell density, etc.) are measured during completion of the bioprocess. These process variables together represent the "process condition". Many of these variables are highly correlated and as such methods such as PCA and PLS can be used to identify summary variables that capture the correlation structure in the data. These (typically relatively few) variables can then be extracted and the range of values of theses variables that define a "normal" process condition can be estimated.

All of these approaches model the impact of process parameters on a product produced by cells without any understanding of how the process parameters impact the functioning of the cells and how this ultimately results in changes in CQAs in the product. This results in the definition of the critical process parameters as a set of process conditions that are identified as critical to maintain within acceptable (potentially maturity-dependent) ranges. Because all of these approaches relate CQAs to acceptable ranges of process parameters, they result in a relative lack of flexibility in relation to the process conditions that are used. Indeed, the product CQAs are then effectively tied to the process conditions that characterised the process design space described in the product specification, and changes to these process conditions are therefore limited. To put it simply, in order to guarantee CQAs, a manufacturer is thereafter required to keep CPPs within the predetermined maturity dependent ranges that have been established. This has dramatic practical consequences in the scale up process, since any change in scale is likely to require the characterisation of a new process design space. This makes it slow and costly to perform the scale up process, and to effect necessary or beneficial changes that may be effected in a production scale process.

Therefore, a need exists for a system and method for improved methods for monitoring and controlling bioprocesses.

SUMMARY

According to a first aspect of the disclosure, there is provided a computer-implemented method for monitoring a bioprocess comprising a cell culture in a bioreactor, the method including the steps of:

obtaining measurements of the amount of biomass and the amount of one or more metabolites in the bioreactor as a function of bioprocess maturity;

determining one or more metabolic condition variables selected from: the specific transport rates between the cells and a culture medium in the bioreactor for some or all of the one or more metabolites as a function of bioprocess maturity, the internal concentration of one or more metabolites as a function of bioprocess maturity, and reaction rates for one or more metabolic reactions that form part of the cell's metabolism as a function of bioprocess maturity;

using a pre-trained multivariate model to determine the value of one or more latent variables as a function of bioprocess maturity, wherein the multivariate model is a linear model that uses process variables including the metabolic condition variables as predictor variables;

comparing the value(s) of the one or more latent variables to one or more predetermined values as a function of maturity; and determining on the basis of the comparison whether the bioprocess is operating normally.

The present inventors hypothesised that models that are more informative as to the underlying causes of departure from a normal or optimal evolution of a process could be obtained by describing the process using variables that capture the metabolic condition of the cells in the bioprocess instead or in addition to the process parameters that have been previously used to monitor process evolution. In other words, the invention is based at least in part on the discovery that the metabolic condition of the cells can be seen as a maturity-dependent evolving process that can be characterised using a multivariate batch evolution modelling approach.

Cellular metabolism is the causal reason for the correlation structure exploited by the batch evolution modelling technique described above. As an example, protein concentration increases in tandem with decreasing glutamine concentrations and increasing glutamate concentrations. This is because if the cell is considered as the factory, then metabolism is the process that governs how raw materials (nutrients like glutamine, in this particular example) are used to construct the final product (protein, in this example) as well as the waste created during that production (by-products like glutamate, in this example). Therefore, the cellular metabolism provides a far more complete characterisation of the process condition than the macroscopic properties currently used as input to batch evolution models presently. Using information about the cell metabolism as input to a multivariate batch evolution model therefore provides a better characterisation of the process path because it describes the evolution of the cell's metabolic process directly instead of indirectly describing this evolution through observed macroscopic process conditions that can be measured.

Additionally, using information about the cell metabolism as input to a multivariate batch evolution model enables the characterisation of a process design space in terms of metabolic processes rather than (or in addition to) macroscopic measurements. Product specifications are currently tied to macroscopic measurements (process conditions that are associated with acceptable CQAs). However, the characteristics of a cellular product, such as e.g. a protein, is dependent on the metabolic condition of the cell. In other words, all critical quality attributes are affected by the metabolic condition of the cell, and many macroscopic properties of the culture are responsible for the resulting protein quality primarily because of the impact that the macroscopic properties have on metabolism. Because it is possible according to the present invention to tie a product specification to metabolic properties, far more flexible corrections of process deviations become possible. Indeed, any macroscopic process change that corrects the metabolic condition is acceptable. This contrasts with the present situation in which a manufacturer can only make very limited changes as the macroscopic process conditions must be kept within limits set when the product specification was defined (and agreed with regulatory agencies such as e.g. the U.S. Food and Drugs Administration (FDA) or the European Medicines Agency (EMA), etc). Furthermore, such a definition enables biological products to be manufactured at the scale which makes appropriate sense economically, and enable it to change over time because a process that maintains the metabolic condition consistently will be covered by the initial specification even if the process parameters need to be changed to operate at a new scale. In addition, this may enable manufacturers to bring their product to market faster. This is because the metabolic design space can be created at lab scale and then the regulatory filing (product specification approval) and scale-up activities can be pursued in parallel instead of sequentially.

The method of the first aspect may have any one or any combination of the following optional features.

The multivariate model is advantageously a linear model that uses process variables including the metabolic condition variables as predictor variables and maturity as a response variable.

The step of determining is performed at least in part based on the measurements of the amount of biomass and the amount of one or more metabolites in the bioreactor as a function of bioprocess maturity. Thus, the method comprises determining, at least in part based on the measurements of the amount of biomass and the amount of one or more metabolites in the bioreactor as a function of bioprocess maturity, one or more metabolic condition variables. The step of determining may comprise using a model of conservation of mass in the bioprocess and the measurements of the amount of biomass and the amount of one or more metabolites in the bioreactor to determine the specific transport rates between the cells and a culture medium in the bioreactor for some or all of the one or more metabolites as a function of maturity (i.e. at the maturity associated with the measurements used in the model). The step of determining may comprise using: (a) a metabolic model and (b) the measurements of the amount of biomass and the amount of one or more metabolites in the bioreactor and/or the specific transport rates between the cells and a culture medium in the bioreactor for some or all of the one or more metabolites, to determine one or both of the internal concentration of one or more metabolites as a function of bioprocess maturity, and reaction rates for one or more metabolic reactions that form part of the cell's metabolism, as a function of maturity (i.e. at the maturity associated with the measurements used in the model).

The method may further comprise outputting a signal to a user if the comparison step indicates that the bioprocess is not operating normally. A signal may be output through a user interface such as a screen, or through any other means such as audio or haptic signalling.

Obtaining measurements of the amount of biomass and the amount of one or more metabolites in the bioreactor as a function of bioprocess maturity may comprise obtaining measurements of the amount of biomass and the amount of one or more metabolites, wherein each measurement is associated with a bioprocess maturity value. The measurements may comprise measurements for a plurality of bioprocess maturity values, or a single bioprocess maturity value. Where the measurements comprise measurements for a plurality of bioprocess maturity values, the step of determining one or more metabolic condition variables may be performed separately for each maturity value at which the metabolic condition variables are determined. Where the measurements comprise measurements for a plurality of bioprocess maturity values, a plurality of values may be obtained for each of the one or more latent variables. Comparing the value(s) of the one or more latent variables to one or more predetermined values may comprise comparing the values of the one or more latent variables at each of the plurality of maturities, with respective predetermined values.

The multivariate model may have been trained using data including metabolic condition variables at a plurality of maturities.

The multivariate model may be a PLS or OPLS model. The multivariate model may be a PLS model as defined in equations (1) and (2), where in equations (1) and (2): X is the m×n matrix of process variables at maturities m, Y is the m×1 matrix of maturity values, and T is the m×/matrix of score values that describe the aspects of the process variables that are most correlated with maturity, including the one or more latent variables.

The multivariate model may be a principal component regression. The multivariate model may be a PCR model where PCA is applied on the matrix X of process variables at maturities m, and the matrix Y of maturity values is regressed on the principal components thus obtained to identify the principal components most correlated with maturity, the PCA scores representing latent variables describing the aspects of the process variables that are most correlated with maturity. The multivariate model may be a PCA, the PCA scores representing latent variables describing the aspects of the process variables that are most variable across training data acquired at a plurality of maturities.

Comparing the value(s) of the one or more latent variables to one or more predetermined values may comprise comparing the value for a latent variable to the average value for the latent variable in a set of bioprocesses that are considered to operate normally. A bioprocess may be considered to operate normally if the value of one or more latent variables is within a predetermined range of the average value for the respective latent variables in a set of bioprocesses that are considered to operate normally. The predetermined range may be defined as a function of the standard deviation associated with the average value of the respective latent variables. A bioprocess may be considered to operate normally if the value of one or more latent variables t is within a range defined as average(t)±n*SD(t), where average(t) is the average value of the latent variable tin a set of bioprocesses that are considered to operate normally, SD(t) is the standard deviation associated with average(t), and n is a predetermined constant (which may be the same for the subrange average(t)+n*SD(t) and for the subrange average (t)-n*SD(t), or may differ between these subranges). In embodiments, n is 1, 2, 3 or a value that results in a chosen confidence interval, for example a 95% confidence interval. In embodiments, a bioprocess may be considered to operate normally if the value of one or more latent variables t is within a range defined as a confidence interval, e.g. a 95% confidence interval, around average(t), based on an assumed distribution of t. An assumed distribution may be a Gaussian (normal) distribution, a chi-squared distribution, etc. Where the assumed distribution is a normal distribution, a p % confidence interval (where p can be e.g. 95) may be equivalent to a range of average(t)±n*SD(t), where n is a single value that results in the p % confidence interval (e.g. n may be about 1.96 for a 95% confidence interval).

A bioprocess may be considered to operate normally if it resulted or is predicted to result in a product that complies with a predetermined specification. A predetermined specification may comprise acceptable ranges for one or more critical quality attributes.

Obtaining measurements of the amount of biomass and the amount of one or more metabolites in the bioreactor as a function of bioprocess maturity may comprise measuring amount of biomass and the amount of one or more metabolites in the bioreactor as a function of bioprocess maturity, receiving previously obtained measurements, or a combination of these.

The process variables used as predictor variables in the linear model may include, in addition to the metabolic condition variables, one or more variables derived from the specific transport rates and/or reaction rates, such as one or more variables that are linear combinations of one or more specific transport rates and/or reaction rates.

The process variables used as predictor variables in the linear model may include, in addition to the metabolic condition variables, one or more process conditions variables.

The internal concentration of one or more metabolites may refer to the calculated or estimated concentration of the metabolites within the cells or a part thereof.

Determining one or more metabolic condition variables may comprise determining the specific transport rate of the one or more metabolites between the cells and the culture medium, wherein the specific transport rate of a metabolite i is the amount of the metabolite transported between the cells and the culture medium, per cell and per unit of maturity. The specific transport rate of a metabolite i at a particular maturity m may be determined using equation (7):

[total change of metabolite amount in reactor]=[total flow of metabolite into reactor]−[total flow of metabolite out of reactor]+[secretion of metabolite by cells in reactor]−[consumption of metabolite by cells in reactor] (7).

The specific transport rate of a metabolite i at a particular maturity m ($qMet_m$) may be determined using equation (8) below:

$$\frac{d(V*[Met])}{dt} = \frac{F_F}{\rho_F}*[Met]_F - \frac{F_H}{\rho_H}*[Met]_H - \frac{F_B}{\rho_B}*[Met]_B + qMet*(VCD*V) \tag{8}$$

where V is the volume of the culture, [Met] is the metabolite concentration in the culture, t is the maturity, $F_F$ is the feed mass flow flowrate (if present), ρ is the medium density, $[Met]_F$ is the metabolite concentration in the feed flow (if present), $F_B$ is the bleed mass flow flowrate (if present), $F_H$ is the harvest mass flow flowrate (if present), and VCD is the viable cell density.

The specific transport rate of a metabolite i at a particular maturity m ($qMet_m$) may be determined using equation (8a):

$$\frac{d(V*[Met])}{dt} = \frac{F_F}{\rho}*[Met_F] - \frac{F_H+F_B}{\rho}*[Met] + qMet*(VCD*V) \tag{8a}$$

where V is the volume of the culture, [Met] is the metabolite concentration in the culture, t is the maturity, $F_F$ is the feed mass flow flowrate (if present), ρ is the medium density, $[Met]_F$ is the metabolite concentration in the feed flow (if present), $F_B$ is the bleed mass flow flowrate (if present), $F_H$ is the harvest mass flow flowrate (if present), and VCD is the viable cell density. Equation (8) may be solved using a first order finite approximation for the differential. The term $$-\frac{(F_H+F_B)}{\rho}*[Met]$$

may be replaced by a corresponding term $$-\frac{(F_B)}{\rho}*[Met]_B - \frac{(F_H)}{\rho}*[Met]_H$$

where $[Met_B]$ is the metabolite concentration in the bleed flow (if present), and $[Met]_H$ is the metabolite Concentration in the harvest flow (if present). This may be advantageous where the concentration of the metabolite in the harvest and/or bleed flows cannot be considered to be the same as that in the reactor.

The specific transport rate of a metabolite i at a particular maturity m ($qMet_m$) may be determined for a perfusion culture using equation (9a):

$$qMet_m = \frac{V*([Met]_{m+1}-[Met]_m) - \frac{F_{Fm}}{\rho}*[Met]_F*(t_{m+1}-t_m) + \frac{F_{Fm}}{\rho}*[Met]_m*(t_{m+1}-t_m)}{V*IVCD_m} \tag{9a}$$

where V is the volume of the culture, [Met] is the metabolite concentration in the culture, t is the maturity, $F_F$ is the feed mass flow flowrate, ρ is the medium density, $[Met]_F$ is the metabolite concentration in the feed flow, $F_B$ is the bleed mass flow flowrate, $F_H$ is the harvest mass flow flowrate, and IVCD is the integrated viable cell density between maturities m and m+1.

The specific transport rate of a metabolite i at a particular maturity m ($qMet_m$) may be determined for a fed-batch culture using equation (8b)

$$\frac{d(V*[Met])}{dt} = = \frac{F_F}{\rho_F}*[Met]_F + qMet*VCD*V \tag{8b}$$

The specific transport rate a metabolite i at a particular maturity m ($qMet_m$) may be determined for a fed-batch culture using equation (9b):

$$qMet_m = \frac{\frac{(V_{m+1}*[Met]_{m+1} - V_m*[Met]_m)}{(t_{m+1}-t_m)} - \frac{F_{Fm}}{\rho_F}*[Met]_{Fm}}{((V_{m+1}+V_m)/2)*((VCD_{m+1}+VCD_m)/2)} = \frac{(V_{m+1}*[Met]_{m+1} - V_m*[Met]_m) - \frac{F_{Fm}}{\rho_F}*[Met]_{Fm}*(t_{m+1}-t_m)}{((V_{m+1}+V_m)/2)*IVCD_m}. \tag{9b}$$

This may be particularly useful in embodiments where the feed-flow is continuous or semi-continuous, such as e.g. in drip feed flows.

The specific transport rate a metabolite i at a particular maturity m ($qMet_m$) may be determined for a fed-batch culture using equation (8d):

$$\frac{d(V*[pMet])}{dt} = qMet*(VCD*V) \tag{8d}$$

where [pMet] is a pseudo metabolite concentration that allows the feed flow to be eliminated from equation (8b). This may be particularly advantageous where a bolus feed strategy is implemented (i,e. the feed flow is provided as relatively large instantaneous additions). For metabolites that are provided in the feed flow, a pseudo metabolite concentration [pMet] may be obtained by: (i) using the measured (or otherwise determined, such as e.g. based on the initial reactor volume and the volumes provided in the one or more feed bolus) reactor volume and known feed concentrations to determine how much of the metabolite is added to the reactor with each feed, and (ii) subtracting the value in (i) from all measurements of the metabolite's concentration after the feed. For metabolites that are not present in the feed (or that can be assumed not to be present in the feed), a pseudo metabolite concentration [pMet] may be obtained by: (i) using the measured (or otherwise determined, such as e.g. based on the initial reactor volume and the volumes provided in the one or more feed bolus) reactor volume to determine the change in concentration due to dilution that is caused by each feed, and (ii) adding the value in (i) from all measurements of the metabolite's concentration after the feed.

Equation (8d) may be resolved for the metabolite transport rate qMet at maturity m using equation (9d)

$$qMet_m = \frac{\frac{d[pMet]}{dt}}{VCD_m} = \frac{[pMet]_{m+1} - [pMet]_m}{IVCD_m} \tag{9d}$$

The specific transport rate of a metabolite i at a particular maturity m ($qMet_m$) may be determined for an unfed batch culture using equation (8c):

$$\frac{d(V*[Met])}{dt} = qMet*(VCD*V) \tag{8c}$$

The specific transport rate of a metabolite i at a particular maturity m ($qMet_m$) may be determined for an unfed batch culture using equation (9c):

$$qMet_m = \frac{\frac{d[Met]}{dt}}{VCD_m} = \frac{[Met]_{m+1} - [Met]_m}{IVCD_m}. \tag{9c}$$

This may be particularly advantageous when it can be assumed that the volume V in the reactor is constant (step 1 of equation (9c)).

A function may be fitted to some or all of the metabolite data (i.e. a function that expresses the metabolite concentration as a function of bioprocess maturity for some or all of the metabolites at some or all of the maturity values). For example, this may be advantageous for the purpose of smoothing the metabolite data. Where a function has been fitted to metabolites data, this function can be used to obtain the term $$\frac{d([Met])}{dt}$$

in any of equations (9c), (8c) and (9d). For example, where the function expressing the concentration of a metabolite ($y_j$) is a polynomial of the form $$y_j \cong \sum_{i=0}^{i=n} c_i x_j^i$$

where n is the degree of the polynomial, and x is maturity (e.g. time), then a derivative of this may be determined analytically as $$\frac{d([Met])}{dt}_j = \sum_{i=0}^{n} c_i * i * x_j^{i-1}.$$

The specific transport rate of a metabolite may be a specific consumption rate or a specific production rate. A specific consumption rate may also be referred to as an uptake rate (or cellular uptake rate). A specific production rate may also be referred to as a secretion rate (or cellular secretion rate). A specific transport rate quantifies the rate of transport of a metabolite between an average cell and the culture medium.

Measurements of the amount of biomass in the bioreactor may comprise measurements of the viable cell density. Measurements of the amount of one or more metabolites in the bioreactor may comprise measurements of the amount or concentration of one or more metabolites in the cellular compartment, in the culture medium compartment, or in the cell culture as a whole.

Determining one or more metabolic condition variables may comprise determining reaction rates for one or more metabolic reactions that form part of the metabolism of the cells in the culture as a function of bioprocess maturity. The reaction rates for the one or more metabolic reactions may be determined at least in part using the specific transport rate of the one or more metabolites between the cells and a culture medium in the bioreactor as a function of bioprocess maturity.

Determining reaction rates for one or more metabolic reactions may comprise obtaining a metabolic model comprising said reactions and solving the metabolic model using at least the specific transport rate of the one or more metabolites as constraints of the metabolic model. A metabolic model comprises a stoichiometric matrix S and a set of reaction rates v and solving the metabolic model comprises determining reaction rates vthat satisfy:

$$\text{maximize/minimise } Z(x) = \sum_k \alpha_k * x_k^{\beta_k} \tag{3}$$

$$\text{subject to } S * v = \frac{dmet}{dt} \tag{4}$$

$$\forall\, i, \text{ lower bound}_i \le v_i \tag{5a}$$

$$\forall\, j, v_j \le \text{ upper bound}_j \tag{5b}$$

where x are the k variables that contribute to a cell goal expressed as objective function Z, α and β are coefficients that describe the impact of x on the cell objective function Z, $$\frac{dmet}{dt}$$

is the rate of change of internal concentration of the metabolites in the metabolic model, i and j are indices of sets of reaction rates in the metabolic model for which a lower bound and an upper bound, respectively, are available, wherein at least one lower bound and/or upper bound value is a predetermined function of a specific transport rate of one of the one or more metabolites; optionally wherein determining reaction rates for one or more metabolic reactions is performed using a flux balance analysis approach.

Using flux balance analysis equations (3)-(5b) are solved by setting S*v=0 and expressing Z as a function of one or more of the reaction rates v. In embodiments, obtaining a metabolic model comprises obtaining a metabolic network and deriving a stoichiometry matrix from said metabolic network, or obtaining a stoichiometry matrix. In embodiments, obtaining a metabolic model comprises obtaining one or more objective functions to be minimised or maximised. Suitable objective functions include e.g. the maximisation of biomass production, the maximisation of ATP production, the maximisation of protein secretion, etc.

Using the specific transport rate of the one or more metabolites as constraints of the metabolic model comprises specifying an allowable range of values for at least one of the metabolic reaction rates as a function of at least one of the specific transport rates. Using the specific transport rate of a metabolite i as a constraint of the metabolic model may comprise specifying:

$$\text{lowerbound}_i = f_{low,i}(q\text{Met}_i) \le v_{Exchange,i} \le \text{upperbound}_i = f_{up,i}(q\text{Met}_i) \tag{10}$$

where $q\text{Met}_i$ is the specific transport rate of metabolite i, $f_{low,i}$ is a first function, $f_{up,i}$ is a second function, and $v_{Exchange,i}$ is the rate of a reaction in the metabolic model that captures consumption or secretion of the metabolite i by the cell. As used herein, references to "the cell" may refer to an average cell in the bioprocess.

Determining or measuring any variable as a function of maturity may comprise determining or measuring the variable as a function of time.

Measuring a variable as a function of maturity may comprise measuring the variable inline or offline.

Determining or measuring any variable as a function of maturity may comprise iteratively determining or measuring the variable at a plurality of maturities, such as at successive time points.

The pre-trained multivariate model may have been trained using biomass and metabolite measurements as a function of maturity from a plurality of bioprocesses considered to operate normally, wherein the measurements include measurements at a plurality of maturities. The multiple maturities preferably include maturities that capture the evolution of the bioprocesses from their start to their completion. The number and/or frequency of measurements may depend on the circumstances, such as e.g. on practical considerations associated with the measuring process, on the kinetics of the bioprocess itself, etc.

The multivariate model may have been pre-trained using data from a plurality of similar bioprocesses considered to operate normally, wherein a similar bioprocess is one that uses the same cells for the same purpose. The multivariate model may have been pre-trained using data from a plurality of similar bioprocess in which at least some of the bioprocesses differ from each other by one or more process conditions as a function of maturity. Two bioprocesses may be considered to differ from each other by one or more process conditions as a function of maturity where said one or more process conditions differ between the bioprocesses for at least one of a plurality of maturities.

The method may further comprise predicting the effect of a change in one or more process conditions of the bioprocess on the one or more latent variables and/or the one or more metabolic condition variables.

At least some of the plurality of runs used to train the multivariate model may be associated with one or more critical quality attributes (CQAs). The method may further comprise using the values of one or more process variables including one or more metabolic condition variables and a model trained using the values of the one or more metabolic condition variables for the plurality of training runs and the corresponding CQAs to predict one or more CQAs of the bioprocess. The model may be a PLS model where the process variables are predictor variables and the CQAs are output variables.

The method may further comprise merging multiple measurements and/or metabolic condition variables into a single table where the measurements/variables are aligned by maturity. The method may further comprise subsampling or binning at least some of the measurements and/or metabolic condition variables. The method may further comprise smoothing and optionally supersampling at least some of the measurements and/or metabolic condition variables.

It is advantageous for the data to comprise as many of the measurements as possible for each of a plurality of maturity values. As such, where measurements were obtained at different maturity values, subsampling, binning and/or supersampling techniques can be used to obtain complete sets of measurements for each of a series of maturity values. Without wishing to be bound by theory, it is believed that the analysis performed by the multivariate analysis module is particularly robust to missing data. For example, if an entire observation (all reaction rates) are missing for a particular bioprocess at a particular maturity, the resulting model should still be able to produce useful information. If no observations are available for any of the bioprocesses used to calibrate the model at a particular maturity value, then the model may not perform as well for this particular maturity, but may still perform satisfactorily for other maturity values. For the purpose of the analysis performed by the systems biology module, it is believed to be advantageous for data to be available in relation to a large proportion (such as e.g. 50% or more) of the metabolites included in the metabolic model. Indeed, missing specific transport rates may cause errors to occur in the estimates of the other reaction rates in the metabolic model. As the skilled person understands, the complexity of the metabolic model (i.e. the reactions/pathways) that are included may be adapted to the available data in order to reduce the likelihood of such errors.

According to a second aspect, there is provided a computer implemented method for controlling a bioprocess comprising a cell culture in a bioreactor, the method comprising:

implementing the steps of any of the embodiments of the preceding aspect; and sending a signal to one or more effector device(s) to implement a corrective action if the comparison step indicates that the bioprocess is not operating normally. The method according to the present aspect may have any of the features disclosed in relation to the first aspect.

The method of the present aspect may further have any one or any combination of the following optional features.

The method may further comprise repeating the steps of the method of monitoring the bioprocess, after a predetermined period of time has elapsed since obtaining the preceding measurements.

The method may further comprise determining a corrective action to be implemented using the loadings associated with the one or more latent variables that are determined to be outside of a predetermined range as a function of maturity.

An effector device may be any device coupled to the bioreactor and which is configured to change one or more physical or chemical conditions in the bioreactor.

According to a third aspect, there is provided a system for monitoring a bioprocess comprising a cell culture in a bioreactor, the system including:

at least one processor; and at least one non-transitory computer readable medium containing instructions that, when executed by the at least one processor, cause the at least one processor to perform operations comprising:

obtaining measurements of the amount of biomass and the amount of one or more metabolites in the bioreactor as a function of bioprocess maturity;

determining one or more metabolic condition variables selected from: the specific transport rates between the cells and a culture medium in the bioreactor for some or all of the one or more metabolites as a function of bioprocess maturity, the internal concentration of one or more metabolites as a function of bioprocess maturity, and reaction rates for one or more metabolic reactions that form part of the cell's metabolism as a function of bioprocess maturity;

using a pre-trained multivariate model to determine the value of one or more latent variables as a function of bioprocess maturity, wherein the multivariate model is a linear model that uses process variables including the metabolic condition variables as predictor variables;

comparing the value(s) of the one or more latent variables to one or more predetermined values as a function of maturity; and determining on the basis of the comparison whether the bioprocess is operating normally.

The system according to the present aspect may be configured to implement the method of any embodiment of the first aspect. In particular, the at least one non-transitory computer readable medium may contain instructions that, when executed by the at least one processor, cause the at least one processor to perform operations comprising any of the operations described in relation to the first aspect.

According to a fourth aspect of the disclosure, there is provided a system for controlling a bioprocess, the system including:

a system for monitoring a bioprocess according to the third aspect; and at least one effector device operably connected to the processor of the system for monitoring a bioprocess.

According to a fifth aspect of the disclosure, there is provided a system for controlling a bioprocess, the system including:

at least one processor; and at least one non-transitory computer readable medium containing instructions that, when executed by the at least one processor, cause the at least one processor to perform operations comprising:

implementing the steps of any of the embodiments of the first aspect; and sending a signal to one or more effector device(s) to implement a corrective action if the comparison step indicates that the bioprocess is not operating normally.

The system according to the present aspect may be configured to implement the method of any embodiment of the second aspect. In particular, the at least one non-transitory computer readable medium may contain instructions that, when executed by the at least one processor, cause the at least one processor to perform operations comprising any of the operations described in relation to the second aspect.

According to a sixth aspect, there is provided a method of providing a tool for monitoring a bioprocess comprising a cell culture in a bioreactor, the method including the steps of:

obtaining measurements of the amount of biomass and the amount of one or more metabolites in the bioreactor at a plurality of bioprocess maturities for a plurality of bioprocesses that are considered to operate normally;

determining one or more metabolic condition variables selected from: the specific transport rates between the cells and a culture medium in the bioreactor for the one or more metabolites at the plurality of bioprocess maturities, the internal concentration of one or more metabolites at the plurality of bioprocess maturities, and reaction rates for one or more metabolic reactions that form part of the metabolism of the cells in the culture at the plurality of bioprocess maturities, for each of the bioprocesses;

using the specific transport rates and/or the reaction rates from the plurality of bioprocesses at the plurality of bioprocess maturities jointly to train a multivariate model to determine the value of one or more latent variables as a function of bioprocess maturity, wherein the multivariate model is a linear model that uses process variables including the metabolic condition variables as predictor variables;

defining one or more values of the one or more latent variables as a function of maturity that characterise the bioprocesses that are considered to function normally, optionally wherein the one or more values include the average of one or more latent variables as a function of maturity and/or one or more ranges defined as a function of the standard deviation around the average of a respective latent variable as a function of maturity.

The method may comprise any of the features of the first aspect.

According to a seventh aspect, there is provided a system for monitoring and/or controlling a bioprocess, the system including: at least one processor; and at least one non-transitory computer readable medium containing instructions that, when executed by the at least one processor, cause the at least one processor to perform the method of any of embodiment of the first or second aspect. The system may further comprise, in operable connection with the processor, one or more of:

a user interface, wherein the instructions further cause the processor to provide, to the user interface for outputting to a user, one or more of: the value of the one or more latent variables as a function of bioprocess maturity, the one or more predetermined values as a function of maturity, the result of the comparison step, and a signal indicating that the bioprocess has been determined to operate normally or to not operate normally;

one or more biomass sensor(s);

one or more metabolite sensor(s);

one or more process condition sensors; and one or more effector device(s).

According to an eighth aspect, there is provided a non-transitory computer readable medium comprising instructions that, when executed by at least one processor, cause the at least one processor to perform the method of any embodiment of the first, second or sixth aspect.

According to a ninth aspect, there is provided a computer program comprising code which, when the code is executed on a computer, causes the computer to perform the method of any embodiment of the first, second or sixth aspect.

According to a tenth aspect, there is provided a system for providing a tool for monitoring a bioprocess comprising a cell culture in a bioreactor, the system including:

at least one processor; and at least one non-transitory computer readable medium containing instructions that, when executed by the at least one processor, cause the at least one processor to perform operations comprising:

obtaining measurements of the amount of biomass and the amount of one or more metabolites in the bioreactor at a plurality of bioprocess maturities for a plurality of bioprocesses that are considered to operate normally;

determining one or more metabolic condition variables selected from: the specific transport rates between the cells and a culture medium in the bioreactor for the one or more metabolites at the plurality of bioprocess maturities, the internal concentration of one or more metabolites at the plurality of bioprocess maturities, and reaction rates for one or more metabolic reactions that form part of the metabolism of the cells in the culture at the plurality of bioprocess maturities, for each of the bioprocesses;

using the specific transport rates and/or the reaction rates from the plurality of bioprocesses at the plurality of bioprocess maturities jointly to train a multivariate model to determine the value of one or more latent variables as a function of bioprocess maturity, wherein the multivariate model is a linear model that uses process variables including the metabolic condition variables as predictor variables;

defining one or more values of the one or more latent variables as a function of maturity that characterise the bioprocesses that are considered to function normally, optionally wherein the one or more values include the average of one or more latent variables as a function of maturity and/or one or more ranges defined as a function of the standard deviation around the average of a respective latent variable as a function of maturity.

The system according to the present aspect may be configured to implement the method of any embodiment of the sixth aspect. In particular, the at least one non-transitory computer readable medium may contain instructions that, when executed by the at least one processor, cause the at least one processor to perform operations comprising any of the operations described in relation to the sixth aspect.

BRIEF DESCRIPTION OF THE DRAWINGS

Embodiments of the present disclosure will now be described by way of example with reference to the accompanying drawings in which.

Figure 1A:
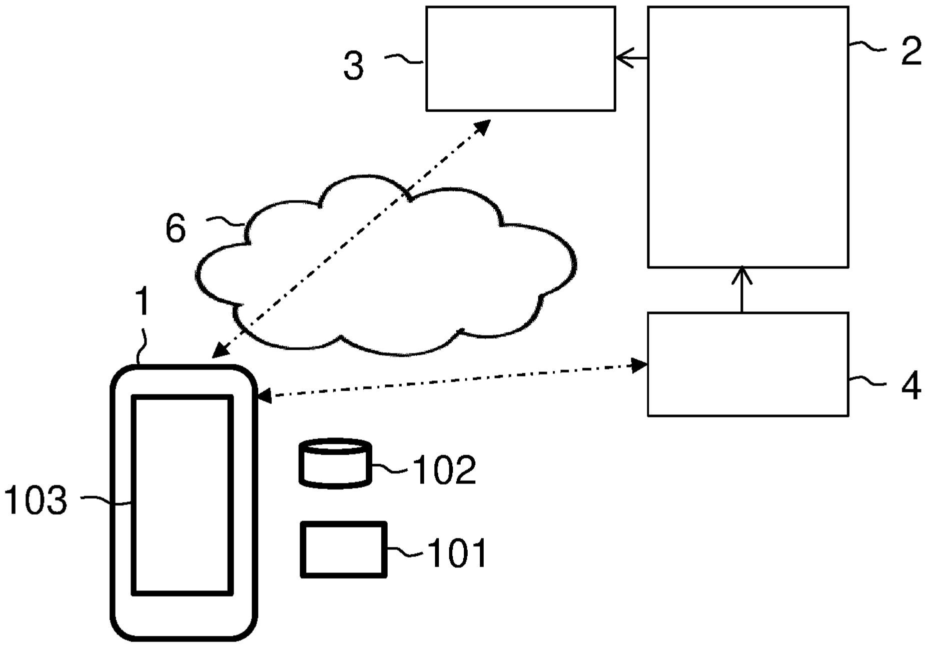
FIG. 1A illustrates schematically a system according to embodiments of the present disclosure.

Where the figures laid out herein illustrate embodiments of the present invention, these should not be construed as limiting to the scope of the invention. Where appropriate, like reference numerals will be used in different figures to relate to the same structural features of the illustrated embodiments.

DETAILED DESCRIPTION

Specific embodiments of the invention will be described below with reference to the figures.

As used herein, the term "bioprocess" (also referred to herein as "biomanufacturing process") refers to a process where biological components such as cells, parts thereof such as organelles or multicellular structures such as organoids or spheroids are maintained in a liquid medium in an artificial environment such as a bioreactor. In embodiments, the bioprocess refers to a cell culture. A bioprocess typically results in a product, which can include biomass and/or one or more compounds that are produced as a result of the activity of the biological components. A bioreactor can be a single use vessel or a reusable vessel in which a liquid medium suitable for carrying out a bioprocess can be contained. Example bioreactor systems suitable for bioprocesses are described in US 2016/0152936 and WO 2014/020327. For example, a bioreactor may be chosen from: advanced microbioreactors (such as e.g. Ambr® 250 or Ambr® 15 bioreactors from The Automation Partnership Ltd.), single use bioreactors (e.g. bag-based bioreactors such as Biostat® STR bioreactors from Sartorius Stedim Biotech GmbH), stainless steel bioreactors (such as e.g. 5 to 2,000 l bioreactors available in the Biostat® range from Sartorius Stedim Systems GmbH), etc. The present invention is applicable to any type of bioreactor and in particular to any vendor and any scale of bioreactor from benchtop systems to manufacturing scale systems.

A cell culture refers to a bioprocess whereby live cells are maintained in an artificial environment such as a bioreactor. The methods, tools and systems described herein are applicable to bioprocesses that use any types of cells that can be maintained in culture, whether eukaryotic or prokaryotic. The invention can in particular be used to monitor and/or control bioprocesses using cells types including but not limited to mammalian cells (such as Chinese hamster ovary (CHO) cells, human embryonic kidney (HEK) cells, Vero cells, etc.), non-mammalian animal cells (such as e.g. chicken embryo fibroblast (CEF) cells), insect cells (such as e.g. *D. melanogaster* cells, *B. mori* cells, etc.), bacterial cells (such as e.g. *E. coli* cells), fungal cells (such as e.g. *S. cerevisiae* cells), and plant cells (such as e.g. *A. thaliana* cells). A bioprocess typically results in the production of a product, which can be the cells themselves (e.g. a cell population for use in further bioprocesses, a cell population for use in cell therapy, a cell population for use as a product such as a probiotic, feedstock, etc.), a macromolecule or macromolecular structure such as a protein, peptide, nucleic acid or viral particle (e.g. a monoclonal antibody, immunogenic protein or peptide, a viral or non-viral vector for gene therapy, enzymes such as e.g. for use in the food industry, for environmental applications such as water purification, decontamination, etc.), or a small molecule (e.g. alcohols, sugars, amino acids, etc.).

Products of a bioprocess may have one or more critical quality attributes (CQAs). As used herein, a "critical quality attribute" is any property of a product (including in particular any chemical, physical, biological and microbiological property) that can be defined and measured to characterise the quality of a product. The quality characteristics of a product may be defined to ensure that the safety and efficacy of a product is maintained within predetermined boundaries. CQAs may include in particular the molecular structure of a small molecule or macromolecule (including in particular any of the primary, secondary and tertiary structure of a peptide or protein), the glycosylation profile of a protein or peptide, etc. A product may be associated with a "specification" which provides the values or ranges of values of one or more CQAs, that a product must comply with. A product may be referred to as "in-specification" (or "according to specification", "within specification", etc.) if all of its CQAs comply with the specification, and "non-specification" (or "out-of-specification") otherwise. CQAs may be associated with a set of critical process parameters (CPPs), and ranges of values of the CPPs (optionally maturity-dependent ranges) that lead to acceptable CQAs. A bioprocess run (i.e. a particular instance of execution of a bioprocess) may be referred to as "normal" or "in-specification" if the CPPs are within the predetermined ranges that are believed to lead to acceptable CQAs, and "not normal" or ("out-of-specification") otherwise. According to the prior art, CPPs are process parameters. The invention provides a way to define the CPPs for a bioprocess in terms of the metabolic condition of the cells in the bioprocess. In other words, the invention enables the operation of a bioprocess (including in particular the monitoring and/or control of a bioprocess within CQA specification) in terms of a metabolic design space instead or in addition to a process design space (the CQAs are maintained within specification by keeping the metabolic activity within specification instead of by keeping process parameters within specification).

As used herein, the term "process condition" refers to any measurable physico-chemical parameter of operation of a bioprocess. Process conditions may include in particular parameters of the culture medium and bioreactor operation, such as e.g. the pH, temperature, medium density, volumetric/mass flowrate of material in/out of the bioreactor, volume of the reactor, agitation rate, etc. Process conditions may also include measurements of the biomass in the bioreactor or the quantity of a metabolite in a compartment as a whole (including in particular the quantity of a metabolite in any of the cell compartment, culture compartment including culture medium and cells, and the culture medium compartment) of the bioprocess.

As used herein, the term "process output" refers to a value or set of values that quantify the desired outcome of a process. The desired outcome of a process may be the production of biomass itself, the production of one or more metabolites, the degradation of one or more metabolites, or a combination of these.

The term "metabolite" refers to any molecule that is consumed or produced by a cell in a bioprocess. Metabolites include in particular nutrients such as e.g. glucose, amino acids etc., by-products such as e.g. lactate and ammonia, desired products such as e.g. recombinant proteins or peptides, complex molecules that participate in biomass production such as e.g. lipids and nucleic acids, as well as any other molecules such as oxygen ($O_2$) that are consumed or produced by the cell. As the skilled person understands, depending on the particular situation, the same molecule may be considered a nutrient, a by-product or a desired product, and this may even change as a bioprocess is operated. However, all molecules that take part in cellular metabolism (whether as an input or output of reactions performed by the cellular machinery) are referred to herein as "metabolites".

The terms "cell metabolic condition" (also referred to herein as "metabolic condition") refers to the value of one or more variables that characterise the dynamics of the metabolism of cells in a bioprocess (i.e. metabolic activity of the cells in a bioprocess). This may include in particular the specific transport rate of a metabolite into/out of cells, the reaction rate of a metabolic reaction, the concentration of a metabolite inside a cell (also referred to herein as "internal metabolite concentration"), or any variable that is derived from one or more of these (e.g. using multivariate analysis techniques). The cell uptake or secretion rate of a metabolite (i.e. the specific transport rate of the metabolite into/out of cells) and the concentration of the metabolite inside a cell (which may be expressed in terms of units of mass per volume or per cell) may be considered to represent metabolic variables (in that they characterise the metabolism of the cell). Further, the concentration of the same metabolite in a compartment of the bioprocess (e.g. in the bulk composition or the liquid medium, which may be expressed in terms of units of mass per volume) may be considered to represent a process variable (in that it characterises a macroscopic process variable). For example, the concentration of oxygen or glucose in the liquid medium (e.g. in mass/volume) may be considered to be a process variable (also referred to herein as "process parameter"), describing the process at a macroscopic level (process condition), whereas the concentration of oxygen or glucose in the cells (e.g. in mass/cell) may be considered to be a metabolic variable, describing the metabolic condition of the cells.

As used herein, the term "maturity" refers to a measure of completion of a bioprocess. Maturity is commonly captured in terms of time from the start of a bioprocess to the end of the bioprocess. Therefore, the term "maturity" or "bioprocess maturity" may refer to an amount of time from a reference time point (e.g. the start of the bioprocess). As such, the wording "as a function of bioprocess maturity" (e.g. quantifying a variable "as a function of bioprocess maturity") may in some embodiments refer to "a function of time" (e.g. quantifying a variable "as a function of time, e.g. since the start of the bioprocess") However, any other measure that increases monotonically as a function of time could be used, such as e.g. the amount of a desired product (or undesired by-product) accumulating in the medium or extracted since the start of a bioprocess, the integrated cell density, etc. may be used. The maturity may be expressed in terms of percentage (or other fractional measure) or as an absolute value that progresses to a value (typically a maximum or minimum value), at which point the bioprocess is considered complete.

The term "multivariate statistical model" refers to a mathematical model that aims to capture the relationships between multiple variables. Common multivariate statistical models include principal components analysis (PCA), partial least square regression (PLS) and orthogonal PLS (OPLS). The term "multivariate statistical analysis" refers to the building (including but not limited to the design and parameterisation) and/or using of a multivariate statistical model.

Principal component analysis (PCA) is used to identify a set of orthogonal axes (referred to as "principal components) that capture progressively smaller amounts of the variance in the data. The first principal component (PC1) is the direction (axis) that maximises the variance of the projection of a set of data onto the PC1 axis. The second principal component (PC2) is the direction (axis) that is orthogonal to PC1 and that maximises the variance of the projection of the data onto the PC1 and PC2 axes. The coordinates of a data point in the new space defined by one or more principal components is sometimes referred to as "scores". PCA functions as a dimensionality reduction approach, resulting in scores for each data point that capture the contribution of multiple underlying variables to the diversity in the data. PCA can be used on historical data about a set of runs of a bioprocess, to characterise and distinguish good (normal) and bad (not normal) process conditions. This enables the retrospective identification of when a historical batch has deviated outside of acceptable process conditions, and to interpret which of the individual process variables are most responsible for the deviation observed in the global process condition. This can then be used to investigate how to avoid such a deviation in the future.

PLS is a regression tool that identifies a linear regression model by projecting a set of predicted variables and corresponding observable variables onto a new space. In other words, PLS identifies the relationship between a matrix of matrix of predictors X (dimension m×n) and a matrix of responses Y (dimension m×p) as:

$$X=TP^t+E \tag{1}$$

$$Y=UQ^t+F \tag{2}$$

where T and U are matrices of dimension m×I that are, respectively, the X score (projections of X onto a new space of "latent variables") and the Y scores (projections of Y onto a new space); P and Q are orthogonal loading matrices (that define the new spaces and respectively have dimensions n×I and p×I); and matrices E and F are error terms (both assumed to be IID—independent and identically distributed—random normal variables). The scores matrix T summarises the variation in the predictor variables in X, and the scores matrix U summarises variation in the responses in Y. The matrix P expresses the correlation between X and U, and the matrix Q expresses the correlation between Y and T. The decomposition of X and Y into a matrix of scores and corresponding loadings is performed so as to maximise the covariance between T and U. OPLS is a variant of PLS where the variation in X is separated into three parts: a predictive part that is correlated to Y ($TP^t$ as in the PLS model), an orthogonal part ($T_{orth}P_{orth}^t$ which captures systematic variability that is not correlated to Y) and a noise part (E as in the PLS model—which captures residual variation). Partial least squares (PLS) and orthogonal PLS (OPLS) regression can be used to characterise the impact that the process condition has on a desired process output (concentration of product, quality attribute, etc.). This can be performed by fitting an (O)PLS model as described above, with X including the one or more process variables that are believed to have an effect on the process output, and Y including the corresponding measures of process output. This can be used to identify which process variables can be manipulated, and how they should be manipulated, to improve or control a desired output.

The Umetrics® software suite (Sartorius Stedim Data Analytics) further includes so called "batch evolution models" (BEM) which describe the time-series evolution of process conditions, referred to as the process 'path'. The process paths are obtained by fitting an (O)PLS model as described above, but where X includes the one or more process variables that are believed to be of potential relevance, measured at multiple times (maturity values) over the evolution of the process, and Y includes the corresponding maturity values. For example, a set of n process variables may have been measured at m maturity values, and these n×m values may be included as a coefficient in the matrix X. The corresponding matrix Y is an m×1 matrix (i.e. a vector of length m) of maturity values. The T matrix therefore comprises scores values for each of the m maturity values and each of I identified latent variables that describe the aspects of the process variables that are most correlated with maturity. By training the BEM on process paths that resulted in the desired product quality at the end of the process, a "golden BEM" can be defined that describes the range of process paths that are acceptable for a future batch (leading to CQAs within specifications), using the values of the scores in T. This enables the monitoring of batches to know that an ongoing batch is within specification. It also means that if an ongoing batch looks like it will deviate from the accepted range of paths, then an alarm can be raised to the operator to let them know that corrective action needs to be taken to prevent loss of product. Furthermore, the process measurements that are contributing to the deviation in process condition can be highlighted to the operator (by analysing the variables in X that most contribute to the score in T that has been observed to deviate from the expected course) to assist in diagnosing the problem and identifying the appropriate course of corrective action. This can all be done in real-time. Furthermore, operators only need to consider a small set of summary parameters during normal batch operation with the option to drill-down into specifics with an appropriate subject matter expert only when something is going wrong.

The term "flux balance analysis" (FBA) refers to a mathematical method which is used for simulating the metabolism of a cell or part thereof. The method represents a metabolic network as a matrix of stoichiometry coefficients (stoichiometric matrix S, which defines the number of each metabolite that is produced or consumed by each reaction in the metabolic network) and a vector of fluxes v (the variables to be determined) which represent the reaction rates for each of the reactions in the matrix S. The method assumes that the system functions at pseudo steady state such that S.v=0. The method further defines an objection function Z (which describes cells goals in mathematical terms, according to an assumption of what the metabolism of the cell is optimised for) to be maximised (or minimised) and a set of constraints lowerbound≤v≤upperbound. In other words, the method solves:

$$\text{maximize/minimise } Z(x) = \sum_k \alpha_k * x_k^{\beta_k} \tag{3}$$

$$\text{subject to } S * v = \frac{dmet}{dt} \tag{4}$$

$$\text{and lowerbound} \leq V \leq \text{upperbound} \tag{5}$$

$$\text{assuming } S * v = 0 \tag{4a}$$

where x are the variables that define the cell goals (typically one or more of the reaction rates v), α and β are coefficients that describe the impact of x on the cell goals, met is the vector of internal metabolite concentrations (i.e. concentration of each metabolite in the cell or part thereof that is being modelled), t is time (or maturity), and lowerbound/upperbound are lower and upper bounds on acceptable reaction rates for each reaction. Equation (4a) does not have a unique solution because the number of reactions it typically higher than the number of metabolites, resulting in an under-determined system of equations with more variables than equations. This can be resolved for example using linear programming, quadratic programming, integer linear programming or mixed integer linear programming. All of these involve the specification of an objective function (to be minimised or maximised) and a set of constraints that specify a space (a convex polytope) over which the objective function is to be optimised. In linear programming, integer linear programming, and mixed integer linear programming, the objective function is linear and so are the constraints. In quadratic programming, the objective function is a quadratic function of several variables, and the constraints are linear. In integer linear programming, the variables are constrained to be integers, whereas mixed integer linear programming uses both integer and linear constraints. Alternatively, the above system of equations can be solved using any optimisation method known in the art, including nonlinear optimisation methods. A suitable optimisation method may advantageously be chosen depending on the form of the objective function. In particular, nonlinear optimisation methods may be advantageous when using objective functions that do not have a convex solution space. Briefly, nonlinear optimisation methods may start with an initial guess of the solution space from which they find a local optimum, and this process may be repeated a number of times to increase confidence that the global optimum has been found. The objective function and constraints are often chosen taking into account biological considerations. The objective function represents how each component in the system contributes to the production of product to be maximised (or minimised, as the case may be). A common choice of objective function is the biomass in the system, assuming that the metabolism of a cell is optimised to maximise the production of new biomass. In such cases, the objective function can be written as:

$$\max_{v} Z = v_{biomass} \tag{6}$$

where v is the vector of reaction rates (also referred to as "fluxes"), and $v_{biomass}$ is the pseudo reaction rate associated with the productions of biomass (as reviewed in e.g. Feist & Palsson, Current Opinion in Microbiology, Vol. 13, Issue 3, June 2010, pages 344-349). The stoichiometry of the biomass pseudo reaction may capture the mass fraction ($\gamma_i$) of the i metabolites needed to produce new cells (by producing e.g. RNA, DNA, proteins, etc.). For example, a biomass pseudo reaction could be provided as $\Sigma_i\gamma_i{*}[i]\rightarrow\text{biomass}+\Sigma_j\gamma_j{*}[j]$ where $\gamma_i$ is the mass fraction of the metabolites i (with concentration [i]) needed to produce the biomass (e.g. amino acids needed to produce protein, nucleotide sugars needed to create DNA and RNA, energy in the form of e.g. ATP, water, etc.) and $\gamma_i$ is the mass fraction of the metabolites j (with concentration [j]) that are by-products of the production of biomass (e.g. ADP/AMP, phosphate, hydrogen, etc.). Other possible choices for the objective function include maximising the amount of ATP produced (e.g. maximising the rate of production of ATP or the ATP yield, where ATP yield may normalise the rate of production of ATP to the specific uptake rate of a nutrient such as e.g. glucose), minimising the amount of nutrient consumed per biomass production, etc. (as reviewed in Schuetz, Kuepfer and Sauer, Mol. Syst Biol. 2007; 3:119). Alternatively, an objective function may include minimizing the overall intracellular flux (e.g. using an objective function of the form $$\min \sum_i v_i^2),$$

in which case quadratic programming may be used to solve the optimisation problem. Other choices of objective function may include maximizing ATP yield per flux unit (e.g. using an objective function of the form max $$\frac{v_{ATP}}{\sum_i v_i^2}\Bigg),$$

in which case a nonlinear solver may be used to solve the optimization problem. The constraints on the fluxes of each reaction (lowerbound/upperbound) can be set to arbitrary low/high values (i.e. very loose constraints). Alternatively, constraints on the fluxes can be determined experimentally. For example, where the flux rate vi of reaction i can be measured experimentally (producing the value $v_{i,exp}$), then the flux in the model can be constrained to be within some error $\varepsilon$ of the experimentally defined value, i.e.: $v_{i,exp}-\varepsilon<v_i i<v_{i,exp}+\varepsilon$.

The term "metabolic flux analysis" (MFA) refers to a method of analysing the metabolism of a cell or part thereof, which employs stoichiometric models (as described above in relation to "flux balance analysis", i.e. equations (3) to (5), but without requiring the pseudo-steady state assumption, i.e. without the assumption made in equation (4a)) of metabolism and experimental determination of intracellular fluxes, for example through isotope labelling techniques combined with NMR (nuclear magnetic resonance) or mass spectrometry detection. When using metabolic flux analysis, solving equations (3), (4) and (5) typically comprises identifying the reaction rates (fluxes) v and internal metabolite concentrations met that satisfy the specified constraints while minimising/maximising the objective function.

FIG. 1A shows an embodiment of a system for monitoring and/or controlling a bioprocess according to the present disclosure. The system comprises a computing device 1, which comprises a processor 101 and computer readable memory 102. In the embodiment shown, the computing device 1 also comprises a user interface 103, which is illustrated as a screen but may include any other means of conveying information to a user such as e.g. through audible or visual signals. The computing device 1 is operably connected, such as e.g. through a network 6, to a bioprocess control system comprising a bioreactor 2, one or more sensors 3, and one or more effectors 4. The computing device may be a smartphone, tablet, personal computer or other computing device. The computing device is configured to implement a method for monitoring a bioprocess, as described herein. In alternative embodiments, the computing device 1 is configured to communicate with a remote computing device (not shown), which is itself configured to implement a method of monitoring a bioprocess, as described herein. In such cases, the remote computing device may also be configured to send the result of the method of monitoring a bioprocess to the computing device. Communication between the computing device 1 and the remote computing device may be through a wired or wireless connection, and may occur over a local or public network such as e.g. over the public internet. Each of the sensor(s) 3 and optional effector(s) 4 may be in wired connection with the computing device 1, or may be able to communicate through a wireless connection, such as e.g. through WiFi, as illustrated. The connection between the computing device 1 and the effector(s) 4 and sensor(s) may be direct or indirect (such as e.g. through a remote computer). The one or more sensors 3 are configured to acquire data that relates to a bioprocess being performed in the bioreactor 2. The one or more effectors 4 are configured to control one or more process parameters of the bioprocess being performed in the bioreactor 2.

The one or more sensors 3 may each be on-line sensors (sometimes also referred to as "inline sensors"), which automatically measure a property of the bioprocess as it progresses (with or without requiring a sample of the culture to be extracted), or off-line sensors (for which a sample is obtained whether manually or automatically, and subsequently processed to obtain the measurement). Each measurement from a sensor (or quantity derived from such a measurement) represents a data point, which is associated with a maturity value. The one or more sensors 3 comprise a sensor that is configured to record the biomass in the bioreactor 2, referred to herein as a "biomass sensor". The biomass sensor may record a physical parameter from which the biomass in the bioreactor (typically in the form of the total cell density or the viable cell density) can be estimated. For example, biomass sensors based on optical density or capacitance are known in the art. The one or more sensors further comprise one or more sensors that measure the concentration of one or more metabolites, referred to herein as "metabolite sensors". A metabolite sensor may measure the concentration of a single or a plurality of metabolites (such as e.g. from a few metabolites to hundreds or even thousands of metabolites), in the culture as a whole, the culture medium compartment, the biomass compartment (i.e. the cells as a whole), or specific cellular compartments. Examples of metabolite sensors are known in the art and include NMR spectrometers, mass spectrometers, enzyme-based sensors (sometimes referred to as "biosensors", e.g. for the monitoring of glucose, lactate, etc.), etc. As used herein, sensors 3 (such as e.g. metabolite and biomass sensors) may also refer to systems that estimate the concentration of a metabolite or the amount of biomass from one or more measured variables (e.g. provided by other sensors). For example, a metabolite sensor may in practice be implemented as a processor (e.g. processor 101) receiving information from one or more sensors (e.g. measuring physical/chemical properties of the system) and using one or more mathematical models to estimate the concentration of a metabolite from this information. For example, a metabolite sensor may be implemented as a processor receiving spectra from a near infrared spectrometer and estimating the concentration of metabolites from these spectra. Such sensors may be referred to as "soft sensors" (by reference to their "measurements" being obtained using a software rather than by direct measurement). The one or more sensors 3 may optionally further include one or more sensors that measure further process conditions such as pH, volume of the culture, volumetric/mass flowrate of material in/out of the bioreactor, medium density, temperature, etc. Such sensors are known in the art. Whether one or more sensors 3 that measure further process conditions are necessary or advantageous may depend on at least the operating mode and the assumptions made by the material balance module as will be explained further below. For example, where the bioprocess is not operated as an unfed-batch, it may be advantageous to include one or more sensors measuring the amount and/or composition of the flows entering and/or leaving the bioreactor. Further, where the material balance module does not assume a constant volume in the bioreactor, it may be advantageous to include a sensor that measures the volume of liquid in the bioreactor (such as e.g. a level sensor).

Figure 1B:
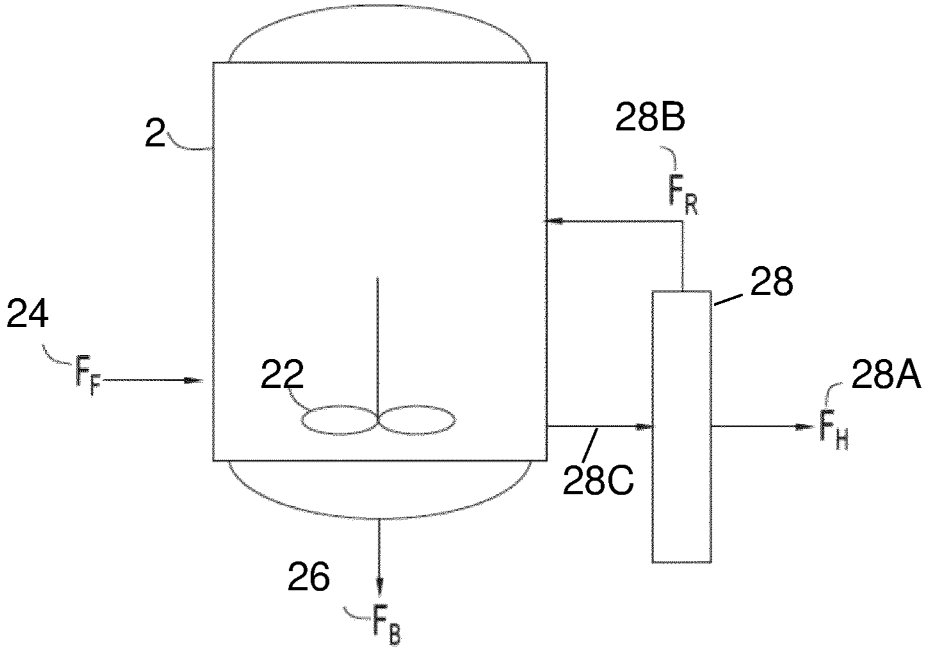
FIG. 1B shows a simplified process diagram for a generic bioprocess that can be implemented in a system such as that of FIG. 1A.

FIG. 1B shows a simplified process diagram for a generic bioprocess that can be implemented in the system of FIG. 1A. The bioprocess is implemented in the reactor 2, which in the embodiment shown is equipped with agitation means 22. Four flows are depicted, although depending on the particular situation any or all of these flows may be absent. A first flow 24 is a feed flow $F_F$ containing anything that is added to the culture in the bioreactor (typically this includes fresh medium, in which case the bioprocess may be referred to as a "fed-batch" process, "perfusion" process or "continuous" process), a second flow 26 is a bleed flow $F_B$ that has the same composition as the culture in the bioreactor, a third flow 28A is a harvest flow $F_H$ which is obtained through the processing of an auxiliary harvest stream 28C through a cell separation means 28 to produce the third (harvest) and fourth flow 28B, the fourth flow 28B being a recycle flow $F_R$ comprising the cells and any culture medium that has not been completely separated out in the cell separation means 28. In embodiments, the recycle flow $F_R$ may be ignored as considering only the harvest flow $F_H$ is sufficient to capture the flow that is effectively output from the bioreactor through the harvesting and cell separation process. Therefore, the reference to a harvest flow being present or absent may refer to the auxiliary harvest stream 28C (and derived harvest and recycle flows—$F_H$ and $F_R$) being present or absent. This harvest flow $F_H$ may be assumed to comprise medium that has the same composition as the medium in the reactor, but no or few cells. The feed, bleed and harvest flows ($F_F$, $F_B$, $F_H$ and $F_R$) may all be absent, in which case the bioprocess is referred to as an "unfed batch process" or simply "batch process". When a feed flow $F_F$ and a harvest flow $F_H$ are provided, the bioprocess may be referred to as a "perfusion" culture. When a feed flow $F_F$ and a bleed flow $F_B$ are provided such that the bioprocess is operated at (pseudo) steady-state (from a process condition point of view, i.e. maintaining in particular the volume of the culture constant), the bioprocess may be referred to as a "continuous" culture. When a feed flow $F_F$ is provided in the absence of output flows (bleed and harvest flows, $F_B$ and $F_H$), the bioprocess may be referred to as a "fed-batch" process. The present invention is applicable to all of the above operating modes.

Figure 1C:
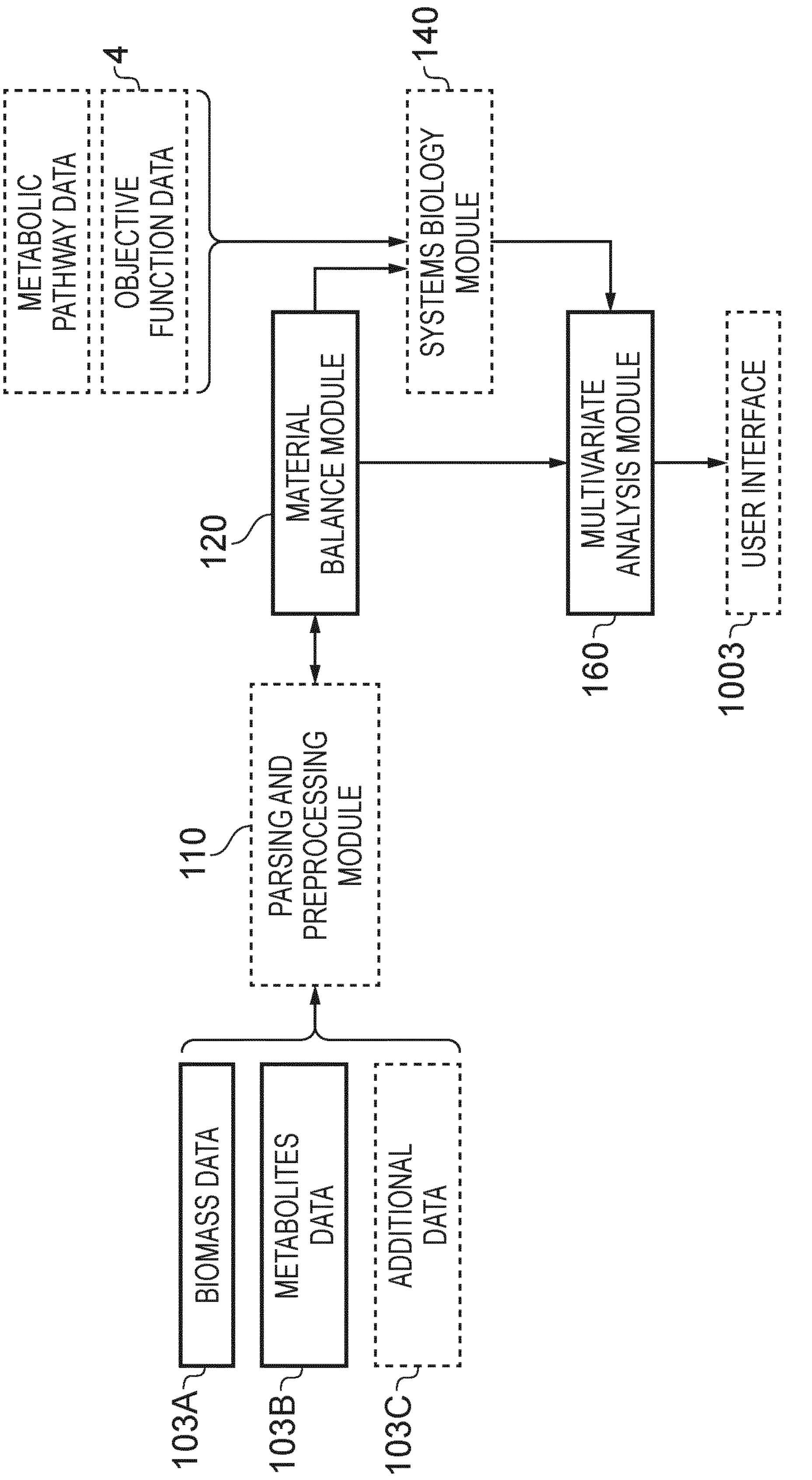
FIG. 1C illustrates schematically a computing architecture for implementing a method according to embodiments of the invention.

FIG. 1C illustrates schematically a computing architecture for implementing a method according to embodiments of the invention. On FIG. 1C, components that are optional are indicated as dashed boxes. The computing architecture may be embodied in a computer software product that is run by the computing device 1 or a remote computing device. Further some of the modules described below may be executed by the computing device 1 and others by a remote computer. The architecture comprises a parsing and preprocessing module 110, a material balance module 120, a systems biology module 140, and a multivariate analysis module 160. The multivariate analysis module 160 may output one or more results to a user interface 1003 (e.g. user interface 103 of computing device 1). The parsing and preprocessing module 110 takes as input data about one or more bioprocesses, for example data received from the one or more sensors 3, including biomass data 130A, metabolites data 130B, and optional additional data 103C such as e.g. further process data such as temperature, pH, etc. Each data point is associated with a maturity value.

The parsing and preprocessing module 110 converts the data generated by the sensors 103 into a format that can be used by the material balance module 120. This may involve one or more steps selected from: loading the data generated by each of the sensors in the physical apparatus description into the computer used for performing calculations, appending user specified metadata (such as e.g. a batch identifier, date, process condition of interest e.g. where a specific feeding scheme is being evaluated, etc.), merging multiple measurements into a single data table, aligning the measurements to a common set of maturities such as by subsampling or binning higher frequency data and/or smoothing and super-sampling lower frequency data—for example using methods such as linear interpolation, zero-order hold, etc.—(to obtain measurements associated with the same maturities even where sensors acquired measurements at different maturities and/or frequencies), and smoothing some or all of the measurements (e.g. by averaging across a sliding window along a series of measurements, or any other smoothing method known in the art such as e.g. using the Savistsky-Golay algorithm). Merging multiple measurements into a single data table may include combining data in a table where all data is aligned by maturity (e.g. one column per maturity value and one row per sensor). Where data from multiple batches is combined for joint analysis, multiple tables may be created one for each run. Smoothing some or all of the measurements may comprise fitting one or more models to the data, such as e.g. one or more polynomial models. This may result in a function expressing a measurement (e.g. the concentration of a metabolite ($y_j$)) as a polynomial function (e.g. using a method such as the Savitsky-Golay method) of the form $$y_j \cong \sum_{i=0}^{i=n} c_i x_j^i$$

where n is the degree of the polynomial, and x is maturity (e.g. time). In embodiments, the parsing and preprocessing module 110 may instead or in addition to smoothing the measurements data, smooth derived values such as e.g. pseudo metabolite concentrations and/or specific transport rates determined by the material balance module 120.

The material balance module 120 uses the biomass and metabolite concentration data and calculates a metabolite transport rate (qMet) for one or more (such as e.g. all) metabolites for which concentration data is available, at a plurality of maturities m. Concentration data may be available because it has been measured using one or more sensors 3, or because it is known for example by virtue of using a chemically defined medium. References to "measured metabolites" and "measured metabolite concentrations" as used herein refer to metabolites whose concentration is known, regardless of whether it is measured by sensors 3 or whether it has bene previously determined and/or is known as part of the characteristics of a medium that is used. The transport rate $qMet_n$ of a metabolite n, also referred to herein as "specific transport rate" of the metabolite n quantifies the flux of the metabolite between the cells and the culture medium in the bioreactor. This flux typically results from consumption and/or production of the metabolite by the cells, and may be expressed in units of a quantity of metabolite (e.g. mass or moles) per cell per unit of time or maturity. Where the metabolite is a nutrient, the specific transport rate may also be referred to as a "specific consumption rate". Where the metabolite is a product or by-product, the specific transport rate may be referred to as a "specific production rate". The specific transport rate for each metabolite may be calculated using a material balance equation such as equation (7) below:

[total change of metabolite amount in reactor]=[total flow of metabolite into reactor]−[total flow of metabolite out of reactor]+[secretion of metabolite by cells in reactor]−[consumption of metabolite by cells in reactor] (7)

Equation (7) expresses in mathematical form the conservation of mass in the system. At every maturity m (e.g. every time point t), equation (7) must be satisfied. The flows of metabolite in equation (7) may be expressed as mass flows or molar flows (as the latter can be converted to the former and vice-versa using molar mass, such that the conservation of mass expressed in the equation is verified regardless of the units chosen), and the skilled person would be able to convert one into the other. As such, references to mass flows are intended to encompass the use of the corresponding molar flows with corresponding adjustments for consistency of units within an equation. The flow of metabolite into the bioreactor depends on the value of the feed flow $F_F$ and the concentration of the metabolite in this flow (if this flow is present, i.e. $F_F \neq 0$). The flow of metabolite out of the bioreactor depends on the value of the harvest flow $F_H$ (if present) and the value of the bleed flow $F_B$ (if present), and the concentration of the metabolite in these respective flows.

The material balance described in equation (7) can be written for a general system (as illustrated on FIG. 1*b*) as equation (8) below:

$$\frac{d(V*[Met])}{dt} = \frac{F_F}{\rho_F}*[Met]_F - \frac{F_H}{\rho_H}*[Met]_H - \frac{F_B}{\rho_B}*[Met]_B + qMet*(VCD*V) \quad (8)$$

where qMet is the specific metabolite transport rate. In the formulation of equation (8), qMet is negative if the metabolite is being consumed, and positive if it is being produced. Equation (8) assumes that the harvest flow 28A contains the only material leaving the system through the auxiliary harvest flow 28C (i.e. the auxiliary harvest flow and the return flow do not need to be included in the model as material only leaves the system through the harvest flow), and that the cell separation device 28 functions such that the harvest flow 28A can be assumed to contain no cells. Equation (8) can be adapted to include an auxiliary harvest flow 28C (and corresponding [Met] and ρ) and a return flow 28B (and corresponding [Met] and ρ). Further, Equation (8) can be amended to model the removal of some cells through the harvest flow. In other words, additional terms can be added to Equation (8) and some can be removed depending on the set-up of the bioprocess and the assumptions made.

For a perfusion culture (where a feed flow, a bleed flow and a harvest flow are present), equation (8) can be used and assumptions made to facilitate its resolution for qMet. For example, assuming that the metabolite concentration is the same everywhere in the culture medium in the bioreactor, and hence also in the harvest flow and in the bleed flow (in other words, assuming that concentration gradients within the reactor are negligible such that $[Met]_B=[Met]_H=[Met]$), that the medium density is constant everywhere ($\rho=\rho_F=\rho_B=\rho_H$; in particular assuming that change in feed media density due to cell expansion and metabolite secretion is negligible) and that the number of cells lost in the bleed and harvest flows is negligible ($VCD_H=VCD_B=0$), equation (8) can be written as:

$$\frac{d(V*[Met])}{dt} = \frac{F_F}{\rho}*[Met]_F - \frac{(F_H+F_B)}{\rho}*[Met] + qMet*(VCD*V) \quad (8a)$$

where V is the volume of the culture, [Met] is the metabolite concentration in the culture, t is the maturity, $F_F$ is the feed mass flow flowrate, ρ is the medium density, $[Met]_F$ is the metabolite concentration in the feed flow, $F_B$ is the bleed mass flow flowrate, $F_H$ is the harvest mass flow flowrate, and VCD is the viable cell density. Assuming further that the volume of the culture is constant (i.e. $F_F=F_H+F_B$), and using a first-order finite difference approximation for the derivative, equation (8a) can be resolved for the metabolite transport rate qMet at maturity m as:

$$qMet_m = \frac{V*([Met]_{m+1}-[Met]_m) - \frac{F_{Fm}}{\rho}*[Met]_F*(t_{m+1}-t_m) + \frac{F_{Fm}}{\rho}*[Met]_m(t_{m+1}-t_m)}{V*IVCD_m} \quad (9a)$$

where the subscripts m and m+1 indicate a value at the $m^{th}$ and $m+1^{th}$ maturity and $IVCD_m$ is the integrated viable cell density between maturities m and m+1. In embodiments, $IVCD_m$ may be calculated as $((VCD_{m+1}+VCD_m)/2)*(t_{m+1}-t_m))$. Alternatively, in embodiments, a function may be fitted to the viable cell density data (i.e. a function that expresses the viable cell density as a function of time/maturity), for example for the purpose of smoothing the data in the parsing and preprocessing module 110. Such a function can be used to calculate the integrated viable cell density, by integrating the function at maturity m (e.g. analytically). For example, where the function expressing the concentration of a metabolite ($y_j$) is a polynomial (e.g.

using a method such as the Savitsky-Golay method) of the form $$y_j \cong \sum_{i=0}^{i=n} c_i x_j^i$$

where n is the degree of the polynomial, and x is maturity (e.g. time), then an integral of this can be determined analytically as $$\int \sum_{i=0}^{i=n} c_i x_j^i dx = \sum_{i=0}^{n} c_i * \frac{x_j^{i+1}}{i+1} + C$$

where C is a constant. Any methods to calculate an integrated viable cell density may be used in the methods described herein.

As the skilled person understand, the general equation in (7) can be expressed and solved for qMet differently depending on the operating mode (e.g. fed-batch, unfed-batch, etc.) and the assumptions made (e.g. variable volume, variable concentration in the various flows and in the bioreactor, etc.). The skilled person would be able to express and solve equation (7) accordingly, in light of the teaching provided herein. Further, whether a particular assumption is reasonable may depend on the situation, and the skilled person would be able to verify whether this is the case using well known techniques. For example, the skilled person would be able to verify whether the volume of a culture is constant (e.g. by examining the amounts of material flowing in and out of the bioreactor or using a level sensor), whether the medium density is constant (e.g. using a hydrometer), whether the concentration of one or more metabolites is the same in one or more compartments and/or flows (e.g. using one or more metabolite sensors to measure metabolite concentration separately in these compartments and/or flows), etc. The skilled person would further be aware that a particular assumption may be reasonable in one case but not in another. For example, the concentration of a small molecule metabolite in the culture medium may be likely to be the same in the bioreactor and in the out flows (harvest and/or bleed flows), whereas the concentration of a macromolecule may differ between the bioreactor and one or more of the out flows if the macromolecule is likely to be held up on filters or other structures.

For a fed-batch culture (where a feed flow is present, but no bleed flow or harvest flow are present, i.e. $F_H=F_B=0$), equation (8) can be written as:

$$\frac{d(V*[Met])}{dt} = \frac{F_F}{\rho_F} * [Met]_F + qMet * VCD * V \quad (8b)$$

Using a first-order finite difference approximation for the derivative, equation (8b) can be resolved for the metabolite transport rate qMet at maturity m as:

$$qMet_m = \frac{\frac{(V_{m+1} * [Met]_{m+1} - V_m * [Met]_m)}{(t_{m+1} - t_m)} - \frac{F_{Fm}}{\rho_F} * [Met]_{Fm}}{((V_{m+1} + V_m)/2) * ((VCD_{m+1} + VCD_m)/2)} = \frac{(V_{m+1} * [Met]_{m+1} - V_m * [Met]_m) - \frac{F_{Fm}}{\rho_F} * [Met]_{Fm} * (t_{m+1} - t_m)}{((V_{m+1} + V_m)/2) * IVCD_m}. \quad (9b)$$

The approach in equation (9b) may be particularly useful in embodiments where the feed-flow is continuous or semi-continuous, such as e.g. in drip feed flows. In embodiments where a bolus feed strategy is implemented (i.e. the feed flow is provided as relatively large instantaneous additions), Equation (8b) can be rewritten using a pseudo metabolite concentration [pMet], that allows the feed flow to be eliminated from equation (8b), i.e.

$$\frac{d(V*[pMet])}{dt} = qMet * (VCD * V). \quad (8d)$$

For metabolites that are provided in the feed flow, a pseudo metabolite concentration [pMet] may be obtained by: (i) using the measured (or otherwise determined, such as e.g. based on the initial reactor volume and the volumes provided in the one or more feed bolus) reactor volume and known feed concentrations to determine how much of the metabolite is added to the reactor with each feed, and (ii) subtracting the value in (i) from all measurements of the metabolite's concentration after the feed. For metabolites that are not present in the feed (or that can be assumed not to be present in the feed), a pseudo metabolite concentration [pMet] may be obtained by: (i) using the measured (or otherwise determined, such as e.g. based on the initial reactor volume and the volumes provided in the one or more feed bolus) reactor volume to determine the change in concentration due to dilution that is caused by each feed, and (ii) adding the value in (i) from all measurements of the metabolite's concentration after the feed. Equation (8d) can be resolved for the metabolite transport rate qMet at maturity m using a first-order finite difference approximation for the derivative:

$$qMet_m = \frac{\frac{d[pMet]}{dt}}{VCD_m} = \frac{[pMet]_{m+1} - [pMet]_m}{IVCD_m}. \quad (9d)$$

For an unfed-batch culture (where no feed flow, bleed flow or harvest flow is present, i.e. $F_F=F_H=F_B=0$), equation (8) can be written as:

$$\frac{d(V*[Met])}{dt} = qMet * (VCD * V). \quad (8c)$$

Assuming that the volume V in the reactor is constant (step 1 of equation (9c) below), and using a first order finite difference approximation for the derivative (step 2 of equation (9c) below), equation (8c) can be resolved for the metabolite transport rate qMet at maturity m as:

$$qMet_m = \frac{\frac{d[Met]}{dt}}{VCD_m} = \frac{[Met]_{m+1} - [Met]_m}{IVCD_m}. \quad (9c)$$

The integrated viable cell density may be calculated using any methods known in the art. In embodiments, the integrated viable cell density may be calculated, as explained above, using the trapezoidal rule or by integrating a function that may have been fitted to the viable cell density data. In embodiments, a function may be fitted to the metabolite data (i.e. a function that expresses the metabolite concentration as a function of time/maturity), for example for the purpose of smoothing the data in the parsing and preprocessing module 110. Such a function can be used to obtain the term $$\frac{d([Met])}{dt}$$

in any of the above equations (instead of using a first order finite difference approximation), by obtaining the derivative of the function at maturity m (e.g. analytically). For example, where the function expressing the concentration of a metabolite ($y_j$) is a polynomial (e.g. using a method such as the Savitsky-Golay method) of the form $$y_j \cong \sum_{i=0}^{i=n} c_i x_j^i$$

where n is the degree of the polynomial, and x is maturity (e.g. time), then a derivative of this can be determined analytically as $$\frac{d([Met])}{dt}_j = \Sigma_{i=0}^{n} c_i * i * x_j^{i-1}.$$

The equations for qMet as described above (or any corresponding equation that may be defined in view of the configuration of the process and the set of assumptions made) can be solved using the measured biomass and metabolite concentration to obtain a metabolite transport rate at every time point/maturity value where the above measurements are available. Further, this can be performed individually for each measured metabolite. The resulting metabolite transport rates characterise the metabolic condition of the cells in the culture as a function of maturity, and are expressed as an amount of metabolite (mass or moles) per cell per unit of maturity (i.e. typically per unit of time). These characteristics of the cell metabolic condition are captured at a "black box" level in the sense that they do not derive from a model that includes the metabolic processes that occur within the cells, but capture the effect of these processes in terms of which metabolites are produced and consumed by an average single cell. This represents very valuable information regarding the metabolic condition of the cells, which information can be used by the multivariate analysis module 160 to monitor the cell culture as will be described further below.

In addition to being directly usable by the multivariate analysis module 160, the output of the material balance module 120 may also be used by the systems biology module 140, which models the metabolic processes that occur within the cells in the culture in order to calculate at least cell metabolic reaction rates. There are multiple methods known in the art for simulating the metabolism of a cell using a metabolic network (i.e. a set of—often interrelated reactions that together capture some or all of the metabolic processes that occur within a cell), and all such methods may be used by the systems biology module 140. One such method is the flux balance analysis (FBA) method as explained above, which can calculate steady-state metabolic fluxes in a computationally inexpensive manner and without requiring detailed knowledge of enzymatic reaction rates. Alternatively, methods such as Metabolic Flux Analysis (MFA, which does not make the pseudo steady state hypothesis in Equation (4a)), Thermodynamic-based MFA (TMFA, which uses the Gibbs free energy to eliminate results that are not thermodynamically feasible), parsimonious flux balance analysis (which seeks to minimise the total flux through all reactions in the model while also optimising the objective function in equation (3)), enzyme capacity constrained flux balance analysis (which adds constraints to the flux values using enzyme kinetic data such as turnover rates), and other equivalents and modifications of FBA and MFA, as known in the art, may be used. In other words, any approach to determine the cell metabolic reaction rates associated with a metabolic network may be used. In particular, any approach may be used that solves equation 3, subject to the constraints of Equation 4, (with or without making the further assumption of equation (4a)) and one or more boundary constraints such as those of equation (5) (where a lower and/or upper bound may be available for any flux v, i.e. there may be arbitrary sets of fluxes $v_i$ and $v_j$—which may be partially or fully overlapping sets, and may not include all fluxes in the model S, such that ∀i, lower $bound_i \leq v_i$ and ∀j, $v_j \leq \leq$ upper $bound_j$). In embodiments, the systems biology module 140 may calculate further values in addition to the cell metabolic reaction rates, such as e.g. the concentration of one or more metabolites in the cells. This may be the case, for example, where MFA is used to model the metabolic processes that occur within the cell. Any such outputs may also represent metabolic condition variables and may be used by the multivariate analysis module 160 as will be explained further below.

The objective function can be chosen as e.g. the maximisation of biomass, thereby expressing the optimization problem as a calculation of all internal reaction rates, v, that lead to a maximum amount of biomass, Z, being produced in order to simulate cell growth (see equation (6) above). Any other objective function known in the art may be used, as explained above, such as e.g. maximising the production of ATP, maximising the production (or the secretion rate) of a desired product (e.g. if a cell has been specifically engineered to maximise said production), etc. Further, different objective functions may be used at different stages of a bioprocess (i.e. at different maturity values). For example, an objective function that maximises biomass production may be used during the growth phase of a cell culture, and an objective function that maximises a protein production rate may be used in the stationary phase of a cell culture.

The constraints on at least some of the reaction rates v may advantageously be expressed as functions of the specific transport rates determined by the material balance module 120 (where such specific transport rates are available). In particular, the reaction rates v that relate to the transport of a metabolite between the cellular compartment and the culture medium is advantageously constrained using the corresponding specific transport rate determined by the material balance module 120. For example, the constraints on a reaction rate that represents the transport reaction corresponding to the specific transport rate (e.g. secretion of a protein, consumption of glucose from the medium, etc.) may be expressed as:

$$\text{lowerbound}_i = f_{low,i}(q\text{Met}_i) \leq v_{Exchange,i} \leq \text{upperbound}_i = f_{up,i}(q\text{Met}_i) \quad (10)$$

where $f_{low}$ is a first function of qMet; and $f_{up}$ is a second function of $qMet_i$. The functions $f_{low,i}$ and $f_{up,i}$ may both be linear functions of $qMet_i$. For example, $f_{low,i}$ ($qMet_i$) may be chosen as (1−x)*qMet; (where x is a value between 0 and 1, such as e.g. 0.1, 0.2, 0.3, 0.4, etc.). Similarly, $f_{up,i}$ ($qMet_i$) may be chosen as (1+x)

*$qMet_i$ (where x is a value between 0 and 1, such as e.g. 0.1, 0.2, 0.3, 0.4, etc.). In embodiments where x is the same for both functions, this effectively in $v_{Exchange,i}$ being constrained in the interval $qMet_i \pm (x*qMet_i)$. In embodiments where x is e.g. 0.1 (respectively 0.2, 0.3, 0.4 etc.), this results in $v_{Exchange}$, being constrained to be within 10% (respectively 20%, 30%, 40% etc) of $qMet_r$. Further, some reaction rates v may be loosely constrained to include a wide range of possible values (i.e. setting a lowerbound and a high upperbound), for example where no specific transport rate is available that could be used to set the constraints. Further, some reaction rates v may be constrained using prior knowledge of likely reaction rates, such as e.g. obtained from literature or prior experimentation. For example, for a reaction that only works in one direction, the lowerbound may be set to 0. Similarly, realistic upper and lower bounds for some reaction rates may be obtainable from measurements obtained using similar cells and/or enzymes.

The stoichiometry matrix S may contain coefficients that correspond to a metabolic network that captures any part of a cell's metabolism that is assumed to be potentially relevant to the bioprocess. Metabolic networks and pathways that make up such networks are available from multiple databases for many model cell lines and organisms, including e.g. CHO cells and *E. coli* cells. Further, relevant subsets of these metabolic networks and pathways may be selected based on prior knowledge or automatically extracted based on the information available (e.g. using the metabolites for which specific transport rates are available and any other metabolites that are involved whether directly or indirectly in their consumption or production, using information about what enzymes are expressed by a cell such as e.g. obtained through gene expression analysis, etc.). In embodiments, metabolic networks that are limited to the central carbon metabolism may be used. In other embodiments, genome scale metabolic networks may be used. Metabolic networks/pathways that are specific to the cell type used or a related cell type are preferably used.

In embodiments, the systems biology module 140 may execute the following operations: 1) generate or receive (e.g. from a user, database, etc.) a stoichiometric matrix S; 2) generate or receive (e.g. from a user, database, etc.) an objective function Z; 3) for a plurality of (such as e.g. each) maturity points for which specific transport rates have been determined by the material balance module 120, calculate all reaction rates v, by solving equation (3) (or (6), as the case may be) subject to the constraints in equations (4) (or (4a), where a pseudo steady state assumption is made, such as when a flux balance analysis approach is used) and (5) (or (10), where specific transport rates—from the material balance module 120—are available that correspond to the particular reaction rate to be constrained).

In other words, the equations for vas described above (or any corresponding equation that may be defined using a model of cellular metabolism) can be solved using the metabolite transport rates at every time point/maturity value where these were calculated by the material balance module 120. The resulting reaction rates further characterise the metabolic condition of the cells in the culture as a function of maturity, as they not only capture the transport of metabolites between a cell and the culture medium, but also any reaction within the cell that has been included in the model (at least some of which consume or produce the metabolites that have been measured). In embodiments, the stoichiometric matrix S and the optimization function used for every maturity (e.g. time point) may be the same. However, in other embodiments, the stoichiometric matrix S and/or the optimization function (Equation (3)) may be chosen independently (and hence may differ) at every time point. For example, different stoichiometric matrices S may be used at different time points when a metabolic network is constructed from different data (e.g. transcripts) at different time points. As another example, the optimization problem may be modified to reflect different objectives Z depending on the culture phase, such as e.g. maximizing biomass during growth phase and maximizing protein production during stationary phase. As such, the systems biology module 140 generating or receiving a stoichiometric matrix S may comprise the systems biology module 140 generating or receiving a plurality of stoichiometric matrices each associated with one or more maturities. Similarly, the systems biology module 140 generating or receiving an objective function Z may comprise the systems biology module 140 generating or receiving a plurality of objective functions Z each associated with one or more maturities.

Figure 4:
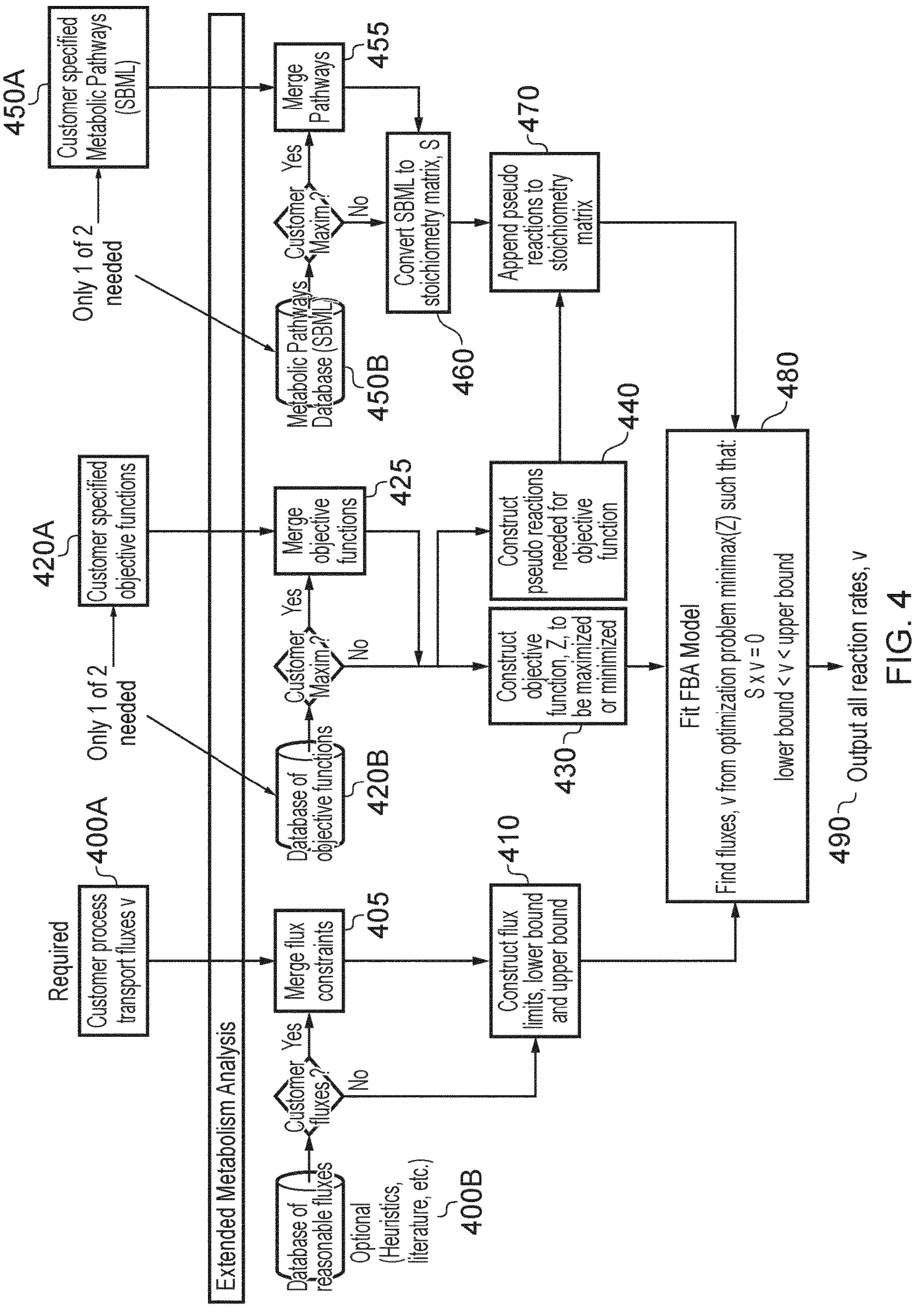
FIG. 4 is a flowchart illustrating a method for determining cell metabolic reaction rates according to embodiments of the present disclosure; in particular, the flowchart illustrates a method of determining reaction rates associated with a metabolic network using a flux balance analysis approach.

As specific embodiment of a method for determining cell metabolic reaction rates that can be implemented by the systems biology module 140 is illustrated on FIG. 4. At step 400A, specific transport rates are received from the material balance module 120. These represent experimentally derived constraints on the metabolic fluxes. At step 400B, additional information on "reasonable" fluxes is optionally obtained from prior knowledge (e.g. data base, default settings, etc.). These represent prior knowledge derived constraints on the metabolic fluxes. At step 405, the experimentally derived constraints are combined with the optional prior knowledge derived constraints, for example by using an experimentally derived constraint wherever available, and using prior knowledge derived constraint otherwise. At step 410, flux boundaries are created using the constraints from step 405. For example, the flux boundaries may be created as functions (e.g. predetermined linear functions) of the constraints from step 410, as explained above.

At steps 420A/420B, one or more cell goals to be optimised are received from a user and/or a database, respectively. At step 425, any user defined cell goals that may have been received are merged with any database-derived cell goals that may have been received. At step 430, an objective function Z is constructed which reflects the cell goals. At step 440, any pseudo-reaction that may be needed to tie the objective function to the metabolic network that will be modelled is optionally created. For example, where the objective function reflects the goal of maximising the production of ATP, a pseudo-reaction may be created which captures the outputs of all reactions that produce ATP. This may be achieved, for example, by including a pseudo reaction that consumes ATP, such as e.g.

$$1ATP \xrightarrow{v_{ATP\_Drain}} 1ADP + 1pi + 1H^+$$

where pi is a phosphate. As the skilled person understands, other formulations of a pseudo reaction that can be associated with the objective function of maximising ATP production may be used (such as e.g. expressed in terms of AMP instead of ATP, etc.). Maximising the flux through such a pseudo reaction (i.e. $Z=\max(v_{ATP\_Drain})$) is equivalent to requiring the solution to maximise fluxes on all reactions that produce ATP. Similarly, where the objective function reflects the goal of maximising biomass production, a pseudo reaction that captures the metabolites that are assumed to be necessary for the production of biomass (and their respective "stoichiometries") may be designed, as explained above.

At steps 450A/450B, a set of metabolic pathways (also referred to herein as a metabolic network) is received from a user and/or a database. At step 455, any user defined and any database derived metabolic pathways are merged into a single metabolic network. At step 460, the metabolic network is converted into a stoichiometry matrix S. At step 470, any pseudo-reactions created at step 440 are added to the stoichiometry matrix S. In embodiments, pseudo reactions that capture the objectives to be used may not be necessary and/or may already be included in a metabolic network received from a user and/or a database. As such, steps 440 and 470 may not be performed. At step 480, the stoichiometry matrix S, objective function Z and flux boundaries lowerbound/upperbound are used to fit a metabolic model (such as a flux balance analysis model b finding the fluxes v that maximise/minimise Z, subject to the constraints that $$\frac{dm}{dt} = S*v$$

(where S*v=0 when using flux balance analysis) and lowerbound<v<upperbound, At step 490, all reaction rates v (solutions of the flux balance analysis) are output.

Turning back to FIG. 1C, the function of the multivariate analysis module 160 will now be described. The multivariate analysis module 160 takes inputs from the material balance module 120 (in the form of the qMetthat have been determined as explained above for a plurality of time/maturity values over the course of one or more bioprocesses), and optionally also from the systems biology module 140 (in the form of at least the reaction rates v- and optionally also the internal metabolites concentrations m—that have been determined as explained above for a plurality of time/maturity values over the course of one or more bioprocesses, if available). Each of these inputs provides information about the cell metabolic condition at a given time/maturity during a bioprocess. The inputs from the systems biology module 140 are not required for the functioning of the multivariate analysis module, but they advantageously provide further (potentially more complete/detailed) information about the metabolic condition of the cells. Therefore, embodiments in which the multivariate analysis module 160 takes inputs from the material balance module 120, and embodiments in which the multivariate analysis module 160 takes inputs from the material balance module 120 and the systems biology module 140 are both explicitly envisaged herein. The multivariate analysis module uses this information to characterise the evolution of the bioprocess over time, in a manner that takes into account the cell metabolic condition. This is accomplished using one or more multivariate analysis models as described above, where the variables representing the cell metabolic condition are used instead or in addition to process variables that were previously used in such analyses. This may be advantageously accomplished using a batch evolution modelling process as explained above. In particular, this may be accomplished using a PLS model where, in equations (1) and (2):

- X is the m×n matrix of measured/calculated process variables (including but not limited to the cell metabolic condition variables qMet and/or v values obtained from the material balance module 120 and the systems biology module 140, respectively, and optionally any other process condition that may have been measured) with m being the maturities where these values were calculated (such as e.g. maturities where measurements were available) or measured, and n being the number of measured/calculated variables,
- Y is the m×1 matrix of maturity values,
- T is the m×I matrix of score values that describe the aspects of the measured/calculated process variables that are most correlated with maturity,
- P is the n×I matrix of loading weights that define the relationship between the original measured/calculated process variables and the new scores (in T)—using/latent variables (principal components) to describe the relationship between the original measured/calculated process variables and the maturities,
- E is the residual of X containing the variability of the measured/calculated process variables (including but not limited to the cell metabolic condition variables, i.e. specific transport and/or reaction rates) that is not described by the/principal components;
- U is the m×I matrix of scores that describe the aspects of the maturity variable that are most correlated with the measured/calculated process variables (including but not limited to the cell metabolic condition variables, i.e. specific transport and/or reaction rates);
- Q is the 1×I matrix of loading weights that define the relationship between the original maturity values and the new scores (in U); and
- F is the residual of Y that contains the variability of the maturity variable that is not described by the/principal components.

In other words, the PLS model projects the set of measured/calculated process variables (including the variables that characterise the cell metabolic condition, i.e. the reaction rates v, internal metabolites concentrations (when these have been determined) and/or specific transport rates qMet) and the corresponding maturities t onto principal components that maximize the covariance between the principal components extracted from the measured/calculated process variables and the principal components extracted from the maturity variable. The loadings in P and Q are selected to maximise the covariance between the measured/calculated variables (including at least cell metabolic condition variables) and the maturity. The scores in U describe the variability in maturity, and the set of scores in T describe the variability in the predictive variables X. From a large set of predictor variables in X (many of which are likely to be correlated with each other) recorded as a function of maturity (in Y), the model finds a smaller space that captures much of the variability in the data. Intuitively, the PLS takes as input a large set of highly correlated reaction rates and finds the consistent patterns between these, to identify a smaller set of variables that can be interpreted as drivers of metabolic shifts, and relates the changes in terms of these variables to the maturity. The score values T can then be used as summary variables that characterise the cell metabolic condition as a bioprocess progresses. The parameters of the PLS model (loadings and weights) can be quantified using a series of related bioprocesses (e.g. including data from runs that are considered normal, i.e. resulting in a product "within specification", whether the runs were obtained using the same or different process parameters), in order to define a range of values of the scores that are acceptable. This can be referred to as a model calibration procedure, or model training procedure. The results of the model calibration process can then be used to monitor a new bioprocess (i.e. to implement a monitoring step or a prediction method by using the loadings in P to calculate scores T for new bioprocesses and compare these to the scores for historical bioprocesses that are within specification). In embodiments where the multivariate analysis module 160 takes inputs from the systems biology module 140, these inputs (and as such the variables in X) may include rates that correspond to the specific transport rates obtained by the material balance analysis module 120 (where corresponding rates are rates that are present in the metabolic model and capture the same process as the specific transport rate, i.e. the net input/output of a metabolite in/out of the cells). For example, the material balance analysis module 120 may determine specific transport rates for glucose and lactate, e.g. qGlucose=1 and qLactate=1. These may be used to apply constraints on the corresponding rates calculated by the systems biology module 140, for example 0.7<qGlucose<1.3 and 0.7<qLactate<1.3. The systems biology module 140 will calculate reaction rates v which include those uptake rates and rates of all internal reactions that have been included in the model, such that the objective function is optimised, and qGlucose, qLactate are within the specified ranges. The inputs from the systems biology module 140 may therefore include those qGlucose, qLactate, instead or in addition to the values from the material balance analysis module 120. In embodiments, such as e.g. when using particular implementations of the FBA and constraints approach as described herein, the rates provided by the systems biology module 140 and that correspond to the specific transport rates obtained by the material balance analysis module 120 are identical to those respective corresponding rates. In embodiments where the rates from the material balance analysis module 120 have corresponding rates in the output of the systems biology module 140, it may in practice be sufficient for the multivariate analysis module 160 to receive inputs from the systems biology module 140. Therefore, the multivariate analysis module 160 receiving inputs from the systems biology module 140 and from the material balance analysis module 120 may comprise the multivariate analysis module 160 receiving inputs from the systems biology module 140 and from the material balance analysis module 120 via the systems biology module 140 (i.e. as part of the inputs from the systems biology module 140). This is particularly the case where the corresponding rates are expected to be the same. As the skilled person understands, both sets of inputs (i.e. from the material balance analysis module 120 and from the systems biology module 140) may nevertheless be received by the multivariate analysis module 160, for example to verify that the corresponding rates are indeed the same. In embodiments where the rates from the material balance analysis module 120 have corresponding rates in the output of the systems biology module 140, the multivariate analysis module 160 may receive inputs from both the systems biology module 140 and the material balance analysis module 120, and may, for each rate that has a corresponding rate received from both module, use the rate from one or the other module, or a rate derived from both rates (such as e.g. by averaging the corresponding rates).

Figure 2:
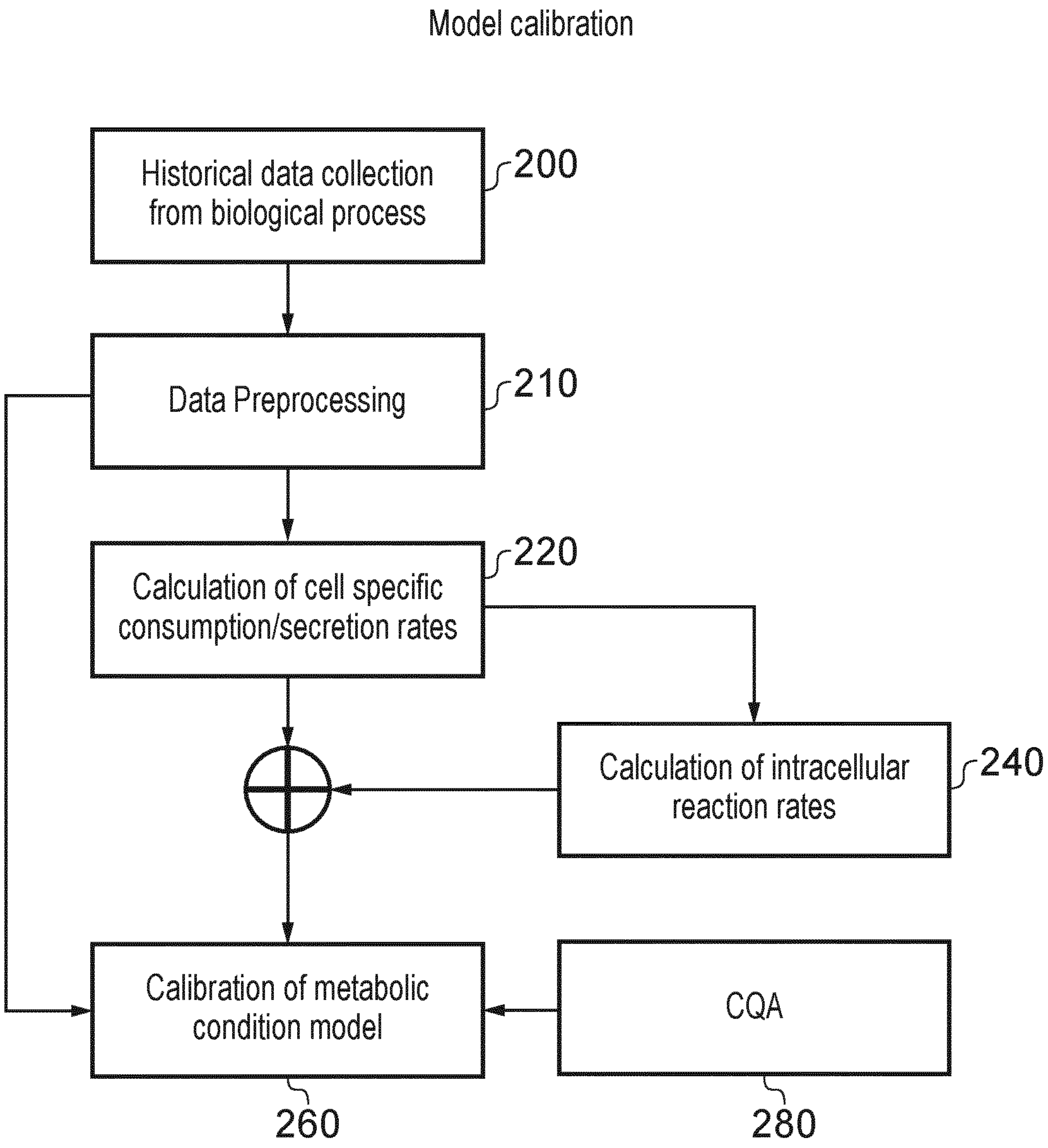
FIG. 2 is a flowchart illustrating a method of providing a tool according to embodiments of the present disclosure; in particular, the flowchart illustrates a model calibration procedure, which results in a calibrated model that can be used to monitor a bioprocess.

FIG. 2 illustrates schematically a model calibration procedure, through which a tool for monitoring a bioprocess may be provided. At step 200, data is obtained in relation to one or more runs of a bioprocess which resulted in a product within specification. The data includes biomass data 103A, metabolites data 103B and optional additional data 103C. Obtaining data may include collecting historical data (i.e. obtaining data from a data store, such as e.g. database 102) or obtaining data by performing one or more runs of a bioprocess and measuring the biomass and concentration of one or more metabolites at a plurality of time points (maturity values). The data preferably includes enough observations to build a representative data set capturing common cause variation in metabolism. The data may additionally include enough observations to capture special cause variation. Common cause variation refers to variations in metabolism that are expected during the normal course of a bioprocess, such as e.g. when the cells progress from an exponential growth phase to a stationary growth phase. Special cause variation refers to variations in metabolism that are the result of a change in a process condition, such as e.g. a change in temperature, pH or bulk media composition. A change in a process condition may be introduced deliberately, for example in order to test the effect of the process condition change on the output of the bioprocess. Where the data only includes data that captures common cause variation, the model resulting from calibration using said data can be used to monitor a process by performing fault detection, i.e. determining whether a bioprocess is operating in expected ("normal") conditions. Where the data additionally includes data that captures special cause variation, the model resulting from calibration using said data may be used to monitor a process by performing fault detection (identifying where a bioprocess has not proceeded in expected ("normal") conditions), and to perform a predictive analysis whereby the effect of a change in process conditions on the bioprocess may be predicted. A data set may be considered to include "enough observations" to capture common and/or special causes of variation when one or more convergence criteria are met. For example, a data set may be considered to include "enough observations" when the standard deviation of the trajectories of the scores for the first n (where n can be e.g. 1, 2, 3, 4 or 5) principal components as a function of maturity remains stable (e.g. does not change by more than e.g. 10%—or any other appropriate value which may be chosen depending on the context and user preferences—at any maturity value) as additional data is added. For example, let us consider a data set including 4 runs of a bioprocess. This data set can be used to calculate specific transport rates and optionally reaction rates as described herein, which in turn can be used to calibrate a PLS model. The T scores associated with each run, as a function of their maturity (each forming a trajectory $[t[comp1]_{m=1}, t[comp1]_{m=2}, \ldots, t[comp1]_{m=m}]$, $t[comp2]_{m=1}, t[comp2]_{m=2}, \ldots, t[comp2]_{m=m}]$, for each run), can be extracted from the PLS model. An average score trajectory and associated standard deviation can then be obtained at each maturity value using the trajectories of the 4 runs ($avg(t[comp1]_{m=1})$ and $sd(t[comp1]_{m=1})$, $avg(t[comp2]_{m=1})$ and $sd(t[comp2]_{m=1})$, etc.). The process can be repeated using an additional run of the bioprocess (i.e. including the 4 previous runs and a fifth run). This will result in new trajectories, average trajectories and standard deviations. If the standard deviation around the average trajectory of the first component score is, at all maturity values, within 10% of the previously obtained standard deviation, then the data may be considered to include "enough observations" to capture the variation that is present in the series of runs on which the model was calibrated (which may be e.g. common cause variation only if all runs did not include any special cause of variation, such as e.g. if all process conditions were maintained between the runs, or common and special cause variation if some of the runs included special cause variation). As the skilled person understands, other approaches to determining an acceptable range of scores and when this has been sufficiently characterised (i.e. what convergence criteria to use) may be used. For example, the concept of a "golden batch" (which represents a normal batch) and an acceptable range of CQA (e.g. a "safe/effective range") may be used to define when the process has been sufficiently characterised (i.e. what convergence criteria to use). For example, different convergence criteria may be used depending on the range of value of critical quality attributes that characterize safe and effective product relative to the range of value considered to be within the "golden batch". Where the range of value considered to be within the "golden batch" is narrow relative to the range of value for a safe and effective product, a few batches within the "golden batch" range may be sufficient to characterise the "golden batch". This is because precise delineation of the range of scores associated with a golden batch is less critical where there is a comparatively wide tolerance from a safety and effectiveness point of view. In other words, if we have a large 'safety factor' to ensure that the "golden batch" range is well within the range of acceptable CQAs then a lower level of certainty in relation to exactly where the "golden batch" range is may be acceptable. By contrast, where the range of value considered to be within the "golden batch" approaches the range of value for a safe and effective product, a larger number of batches within the range may be required. Further, what is considered an acceptable level of (un)certainty may depend on the context, such as e.g. the intended use of the product. Therefore, appropriate convergence criteria to be used for a particular bioprocess are typically determined on a case-by-case basis. Such decisions may further be made in line with guidance from regulatory agency, such as e.g. in view of the Q8-Q10 Quality Guidelines from The International Council for Harmonisation of Technical Requirements for Pharmaceuticals for Human Use (ICH) (available at https://www.ich.org/page/quality-guidelines).

At step 210, the data is processed by the parsing and preprocessing module 110. At step 220, specific transfer rates are calculated by the material balance module 120, for one or more metabolites for which data is available. At step 240, reaction rates are optionally calculated by the systems biology module 140, using the specific transfer rates from step 220. At step 260, a metabolic condition model is calibrated by the multivariate analysis model 160. This may include in particular the following steps. A matrix of maturities for all runs (i.e. the Y matrix) may be obtained using observation-wise unfolding. Observation-wise unfolding comprises concatenating the series of maturity values for a first run, followed by the series of maturity values for a second run, etc. For example, if 3 runs were performed and each run had 6 samples taken, then a matrix of maturity values of size 18×1 would be obtained. A matrix of cell metabolic condition variables for all runs (i.e. forming part or all of the X matrix) may be obtained by stacking the rates determined at step 220 and/or the rates determined at step 260 "on top" of on another such that every column contains data about a particular rate and every row contains data about a maturity value. In the example above, if 95 rates were calculated, then the X matrix would be of size 18×95. Additional optional columns may be added to the output of steps 220,260 in the X matrix. For example, variables that are calculated as a function of other reaction rates (such as e.g. summing up the rate of all reactions that produce a currency metabolite like ATP) may be added. Instead or in addition to this, variables that represent process conditions (e.g. temperature, pH etc.) can be included in the X matrix. Partial Least Square regression is then used to find the scores (T and U), loading weights (P and Q) and residuals (E and F) from the X and Y matrices constructed in the steps above.

Figure 5:
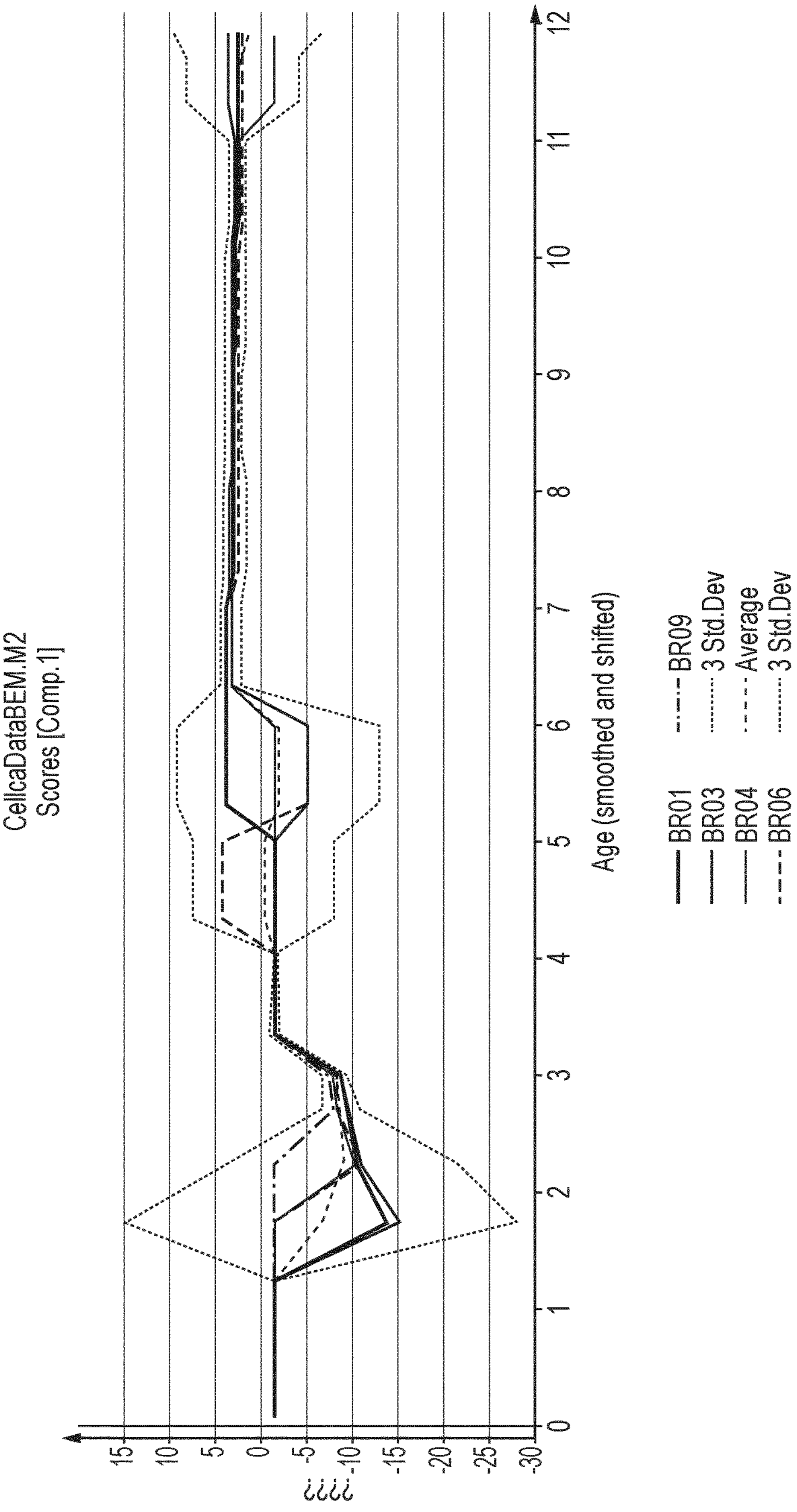
FIG. 5 shows exemplary multivariate control charts derived from the metabolic condition of cells in the bioprocess; in particular, the charts show the scores along the first and second principal components (respectively top and bottom panels) as a function of maturity, for 5 separate instances of a bioprocess (continuous lines), as well as the respective average of these scores (dashed line in the middle of each envelope) and the ±3 standard deviations envelope around the respective average (dashed envelope lines)
Figure 5:
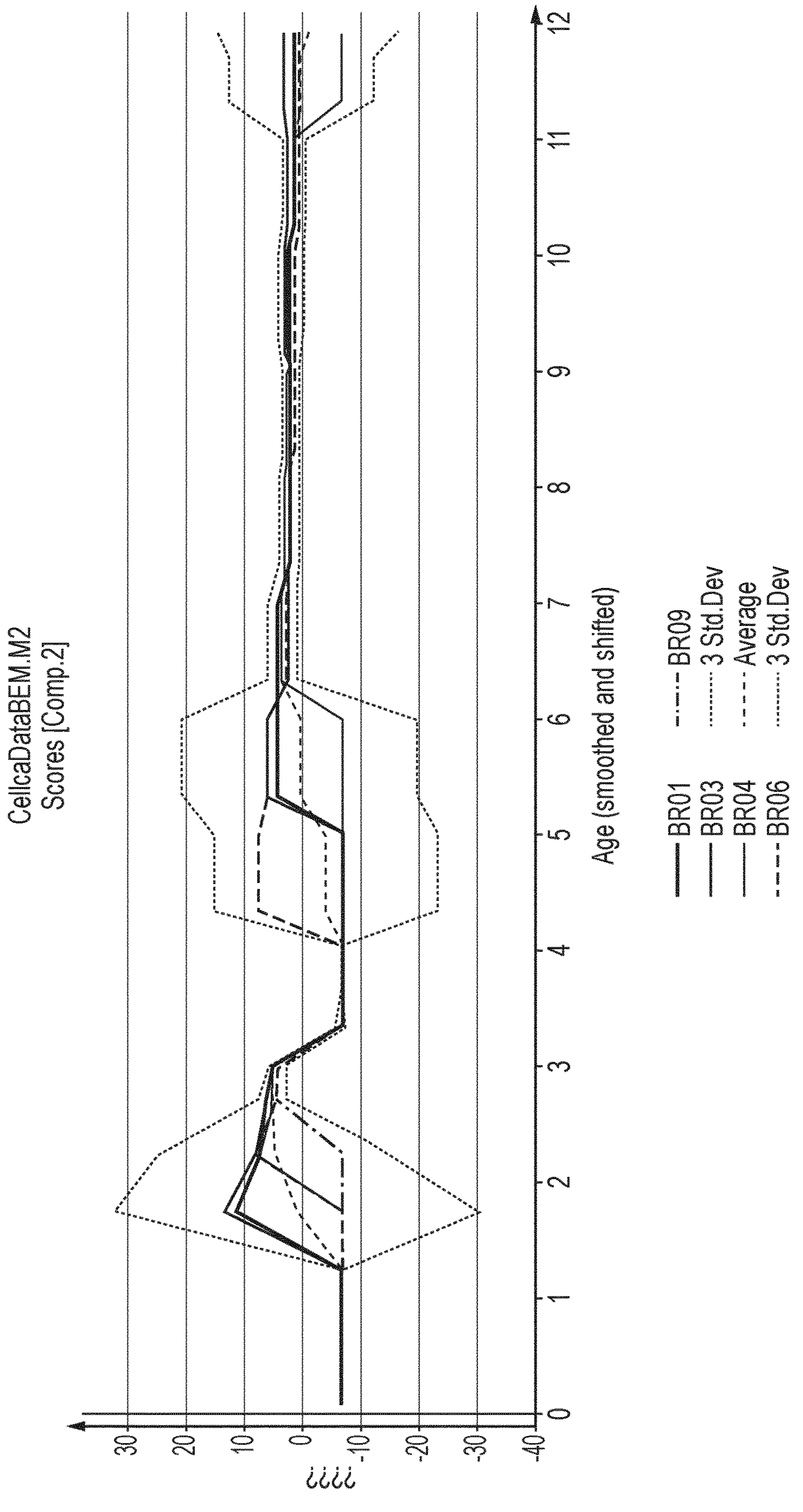

Knowledge of the critical quality attributes of the product of the bioprocess may then be combined 280 with the information from the model, to define runs that are considered normal and/or to correlate measured or predicted CQAs with the metabolic condition information in the model (for example using the reaction rates and/or internal metabolites concentrations, alone or in combination with process conditions, as predictor variables of a PLS model to predict CQAs). The score values in T for those normal runs may then be used to define the normal evolution of internal metabolic conditions by defining an acceptable region (such as e.g. a±n standard deviation (SD) window, where n can be chosen as e.g. 1, 2, 3 or a value that results in a chosen confidence interval e.g. a 95% confidence interval) around the average score value for each maturity value (which may in the simplest case represent a point in time). This is illustrated in FIG. 5, which shows the scores t for the first and second principal components (respectively top and bottom panels) for five runs, as well as the average score over time and the ±3 standard deviations envelope around the average score. Other models may be used at step 260, such as e.g. a PCA (as part of a principal component regression, PCR) or (O)PLS model. For example, such models could be used to define multivariate scores as a function of maturity, which scores could be used to monitor the evolution of a process. When using PCR, the matrix X (matrix of process variables including metabolic condition variables, for all maturities) may be subject to principal component analysis (PCA). The vector Y (vector of maturities) may be used as a vector of outcomes that is regressed on one or more of the principal components as covariates, for example using linear regression. Compared to PLS, PCR has the disadvantage that it creates the score space by looking for variation in X independently of Y. In other words, while the PCA identifies the most process variables that vary the most in the data set, it does so by essentially treating the process variables at the plurality of maturities as replicates (losing the maturity information). This means that the PCA scores are not may not capture the aspects of the process variables that vary particularly as a function of time (although it will capture the variability in the process variables as a whole and as such is nonetheless informative). The PCA scores for one or more of the principal components thus obtained, for a set of batches considered to have run normally (i.e. according to specification) can be obtained, as a function of time, and used to define a "normal" trajectory (for each such principal component), and confidence envelope as already described.

Figure 3:
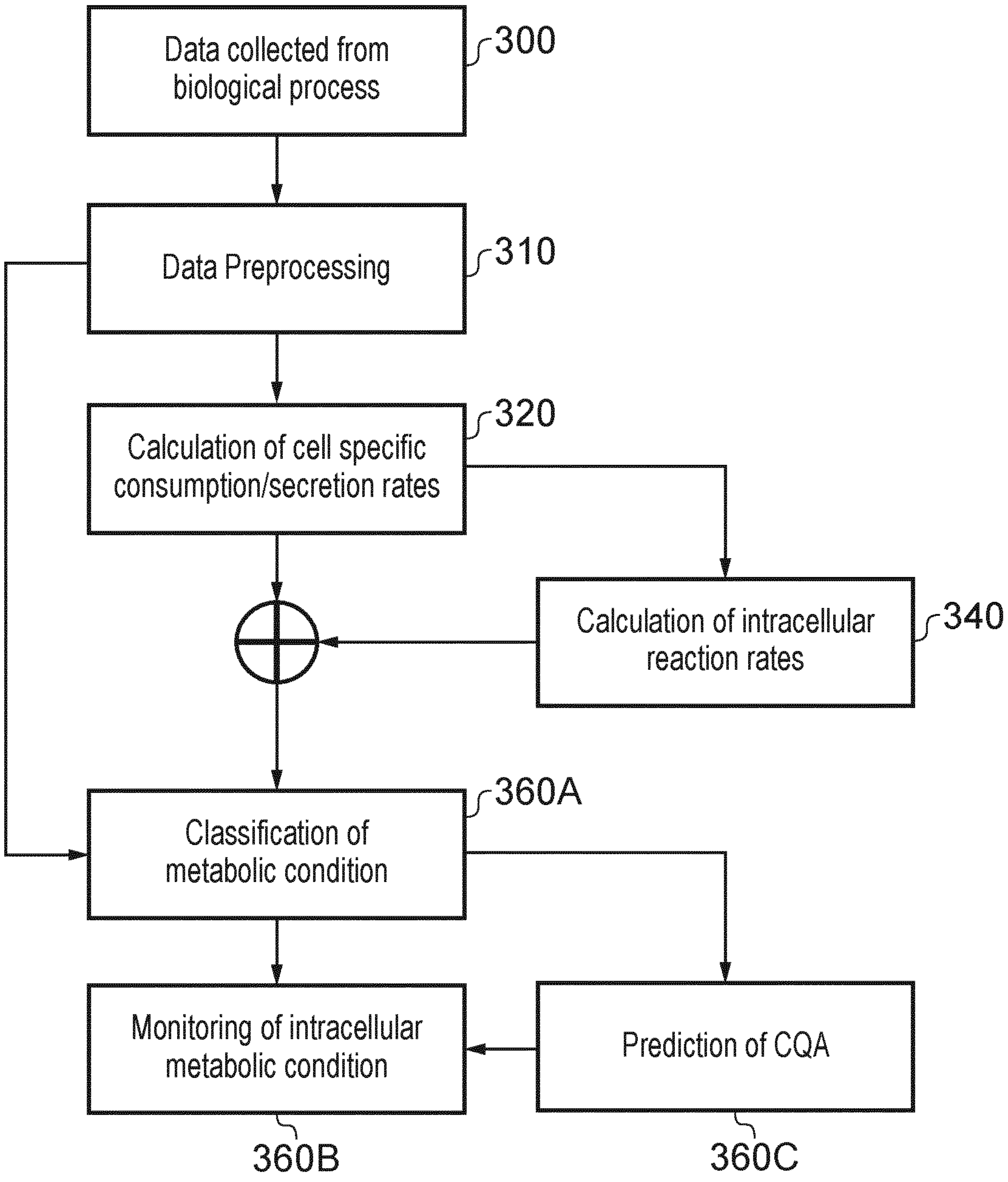
FIG. 3 is a flowchart illustrating a method of monitoring a bioprocess according to embodiments of the present disclosure; in particular, the flowchart illustrates a model prediction procedure through which critical quality attributes of a product of a bioprocess can be monitored.
Figure 6:
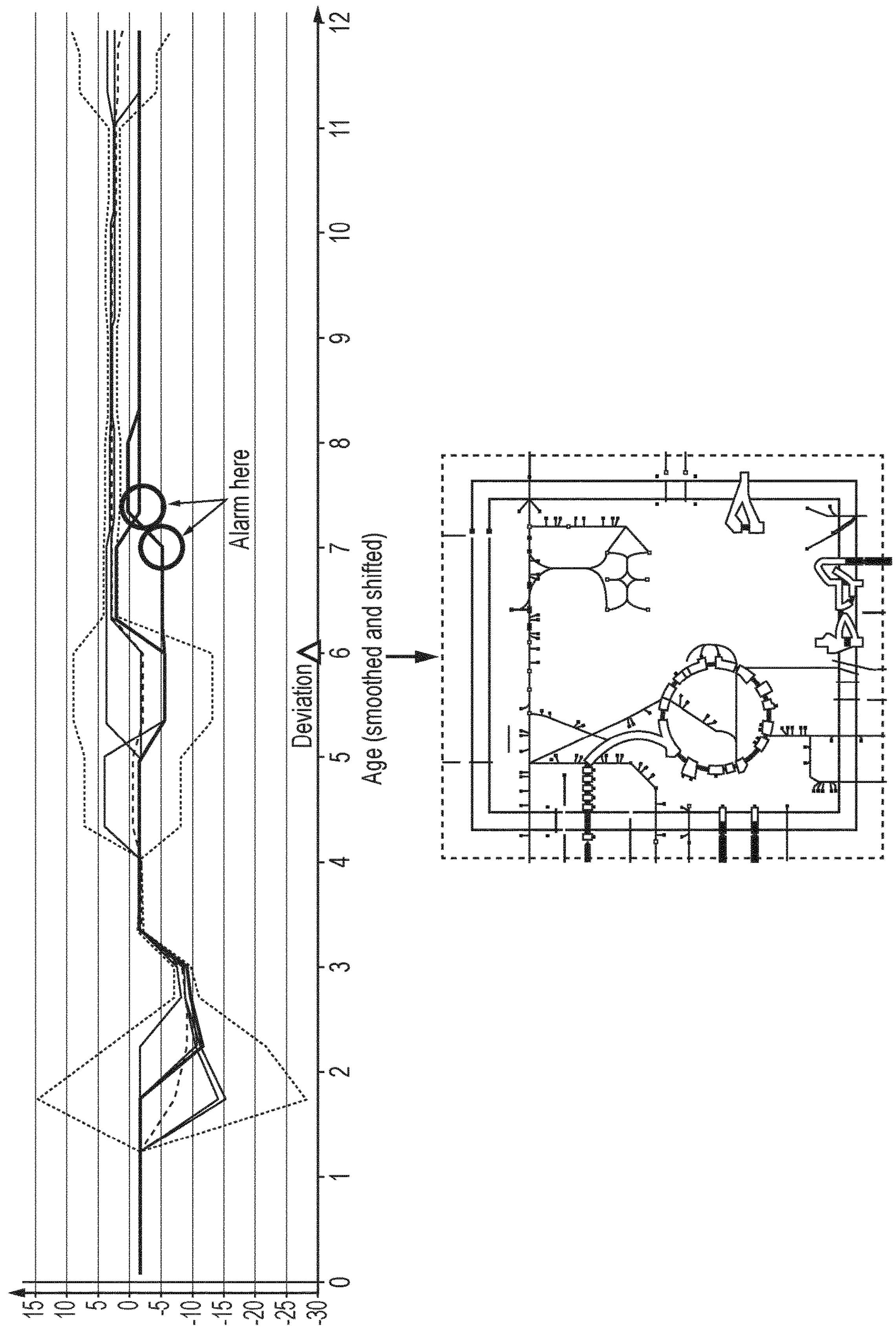
FIG. 6 shows an exemplary multivariate control chart derived from the internal metabolic condition of cells; green solid lines (lines that remain within the dashed envelope throughout their course))=score values calculated from metabolic activity in historical batches (each line is an individual batch); green dashed line (dashed line in the middle of the dashed envelope)—their average value; red dashed lines (dashed envelope)—the ±3 standard deviations limit defining the normal metabolic condition; blue solid lines (the two solid lines that are not within the dashed envelope throughout their course)=new batches that were monitored with the BEM: a deviation (temperature shift) was deliberately implemented at day 7 which causes it to go outside the control limits; this caused changes in the TCA cycle and Ox-Redox state (see highlighted path on the illustrated metabolic network) which were captured by the model.

FIG. 3 illustrates schematically a bioprocess monitoring procedure, which uses a tool obtained by calibrating a model as described in relation to FIG. 2. At step 300, data is obtained in relation to a run of a bioprocess to be monitored. The data includes biomass data 103A, metabolites data 103B and optional additional data 103C. At step 310, the data is optionally processed by the parsing and preprocessing module 110. At step 320, specific transfer rates are calculated by the material balance module 120, for one or more metabolites for which data is available. At step 340, reaction rates are optionally calculated by the systems biology module 140, using the specific transfer rates from step 320. At step 360A, a pre-calibrated metabolic condition model is used to classify the metabolic condition of the bioprocess (optionally supplemented with information about the process conditions) between normal and "not normal" classes, by calculating the metabolic condition of the cells in the bioprocess and comparing this to the expected metabolic condition of the cells in a normal bioprocess. Where the model is a PLS model, the previously calibrated loading weights P may be used to project the rates calculated at steps 320, 340 onto the one or more principal components that form the new space defined by P, in order to obtain the new variables T that capture the metabolic condition of the cells in the bioprocess. In other words, the previously calibrated loading weights P may be used to calculate scores T for the new run. In embodiments where process conditions and/or optional derived variables were included in the model calibration, these may also be used in the projection step. Comparing the metabolic condition of the cells in the bioprocess to the expected metabolic condition of the cells in a normal bioprocess may comprise comparing one or more of the scores T obtained for the bioprocess with a confidence envelope (which can be e.g. a confidence interval or a standard deviation envelope, i.e. an envelope defined as the range of values between ±n standard deviations of an average value—where n can be e.g. 1, 2 or 3, or any value that is equivalent to a p % confidence interval under a chosen statistical distribution, and n can be the same or different for the subrange above the average value and the subrange below the average value, i.e. the range need not be symmetrical around the average) for a set of runs that are considered normal (such as e.g. runs that are known to result in in-specification product). The metabolic condition of the cells in the bioprocess at a particular maturity value may be classified as "normal" if the T score for at least the first principal component falls within the standard deviation envelope, and "not normal" otherwise. The metabolic condition of the cells in the bioprocess at a particular maturity value may be classified as "normal" if the T score for at least the first and the second principal components (or the first, second and third, or any number of the principal components) fall within the respective confidence envelope, and "not normal" otherwise. Any number of principal components (up to the number of variables in the data) can be extracted, and any of these can in principle be monitored. However, successive additional principal components capture progressively smaller amounts of the variability in the data. Further, from a process monitoring point of view it may be advantageous for as few principal components to be monitored as may be necessary to capture a departure from a normal state. Indeed, increasing the number of principal components that are monitored may increase the complexity of the monitoring process and reduce the flexibility of the process condition definition, with limited gain in terms of ensuring that the process runs according to specification. Therefore, it may be advantageous for only the first (or only the first two, only the first three, etc.) principal component to be monitored. In embodiments, the number of principal components to be extracted (and optionally monitored) is determined by cross-validation where one or more additional principal components are extracted and/or monitored if this results in an increased cross-validation rate when predicting the values in Y from the values in X. A step 360B, a fault may be identified if the metabolic condition of the cells in the bioprocess is classified as "not normal". The fault may be reported to a user in real time (i.e. as soon as it is identified at step 360A). In embodiments, the identification of a fault may cause a signal to be send to a user interface or to an effector device, in order for corrective action to be taken by an operator or automatically by the effector device. At step 360C, one or more critical quality attributes may be predicted based on the metabolic condition of the cells, for example using a pre-trained predictive model such as PLS. Steps 300 to 360A and optionally 360B and 360C may be repeated for every time point/maturity value at which data is acquired. An exemplary result is illustrated on FIG. 6, which shows the scores t for the first principal component for three normal runs, as well as the average score over time and the ±3 standard deviations envelope around the average score for the normal runs, and the scores for the first principal component for two runs in which a process condition change (temperature shift) that result in an out-of-specification product were deliberately included at day 7. As can be seen on FIG. 6, these changes caused the metabolic condition of the cells in the bioprocess to move outside of the standard deviation envelope for a normal process, thereby triggering an alarm. Further, using the information in the loading weights P, it was possible to trace back the effect on the first component score to the TCA cycle and Ox-Redox state (see highlighted path on the illustrated metabolic network) which were captured by the model.

Thus, the invention finds uses in monitoring bioprocesses to ensure that they remain within specification. This also enables for alarms to be raised for the process operators so that corrective action can be taken to bring the batch back in-specification or to end a batch early to avoid the waste of further resources.

EXAMPLES

Exemplary methods of calibrating a model, as well as exemplary methods for monitoring a bioprocess will now be described.

Materials and Methods

Unfed Batch Culture (Example 1)

Figure 7:
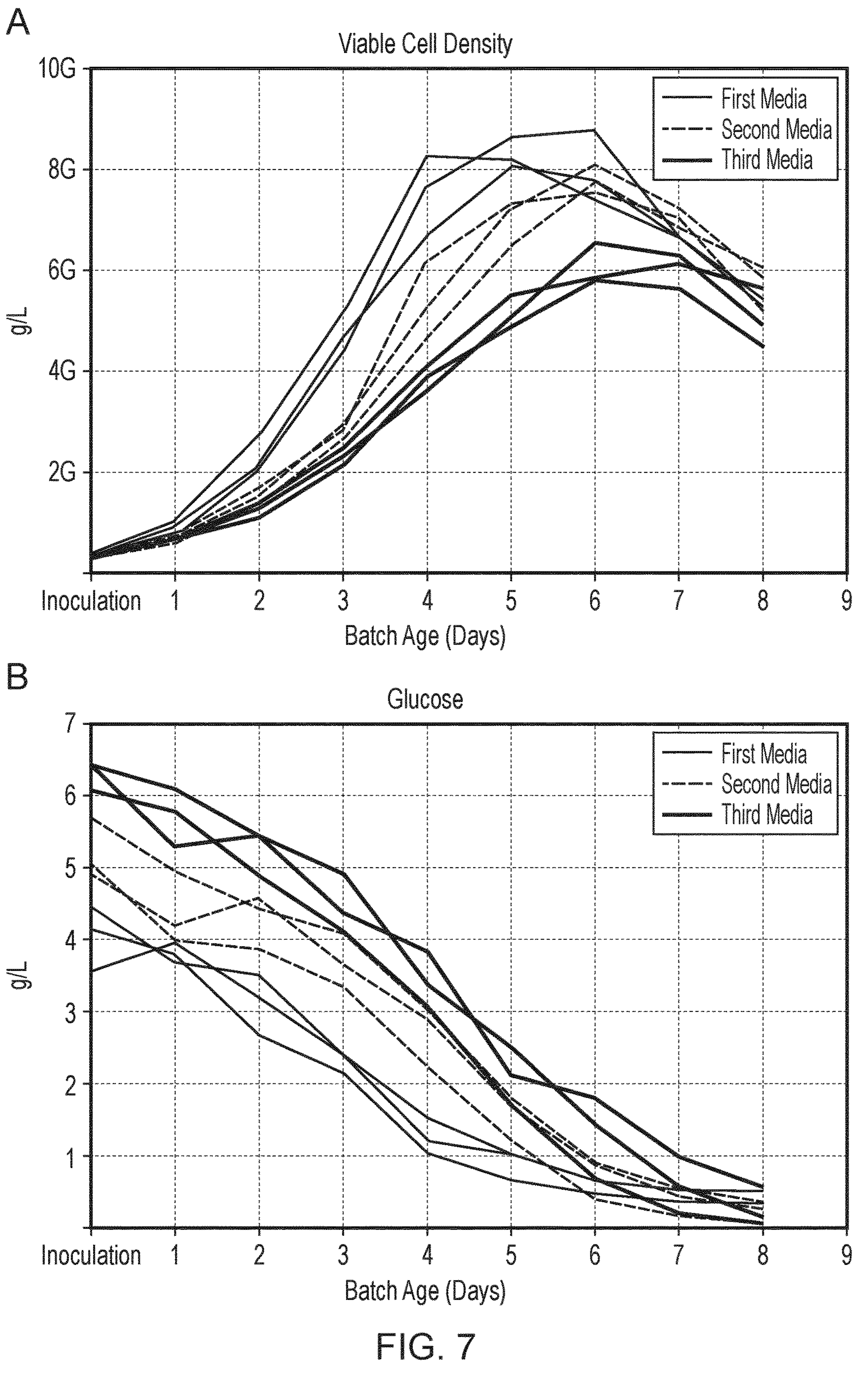
FIG. 7 shows simulated raw data from multiple sensors as a function of maturity (here shown as batch age in days) in an unfed-batch bioprocess run with 3 different media (. (A) viable cell density data; (B) Glucose concentration, (C) Lactate concentration and (D) Glutamine concentration.
Figure 7:
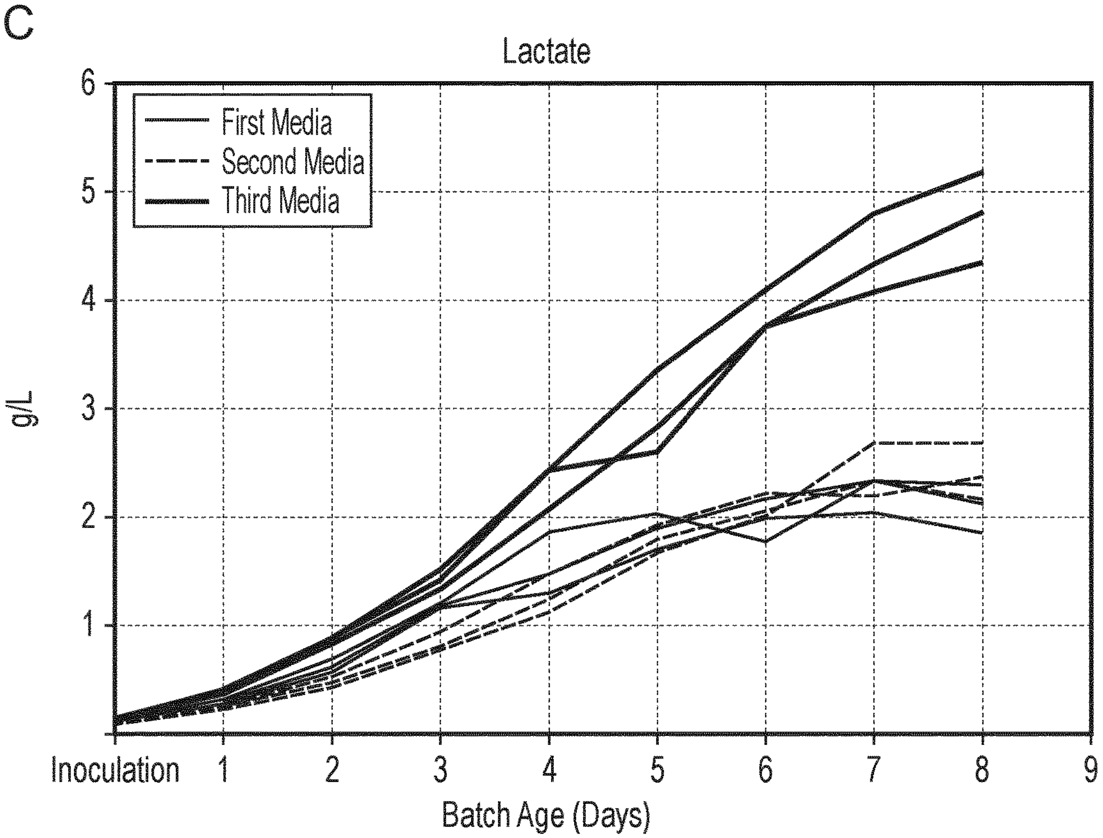
Figure 7:
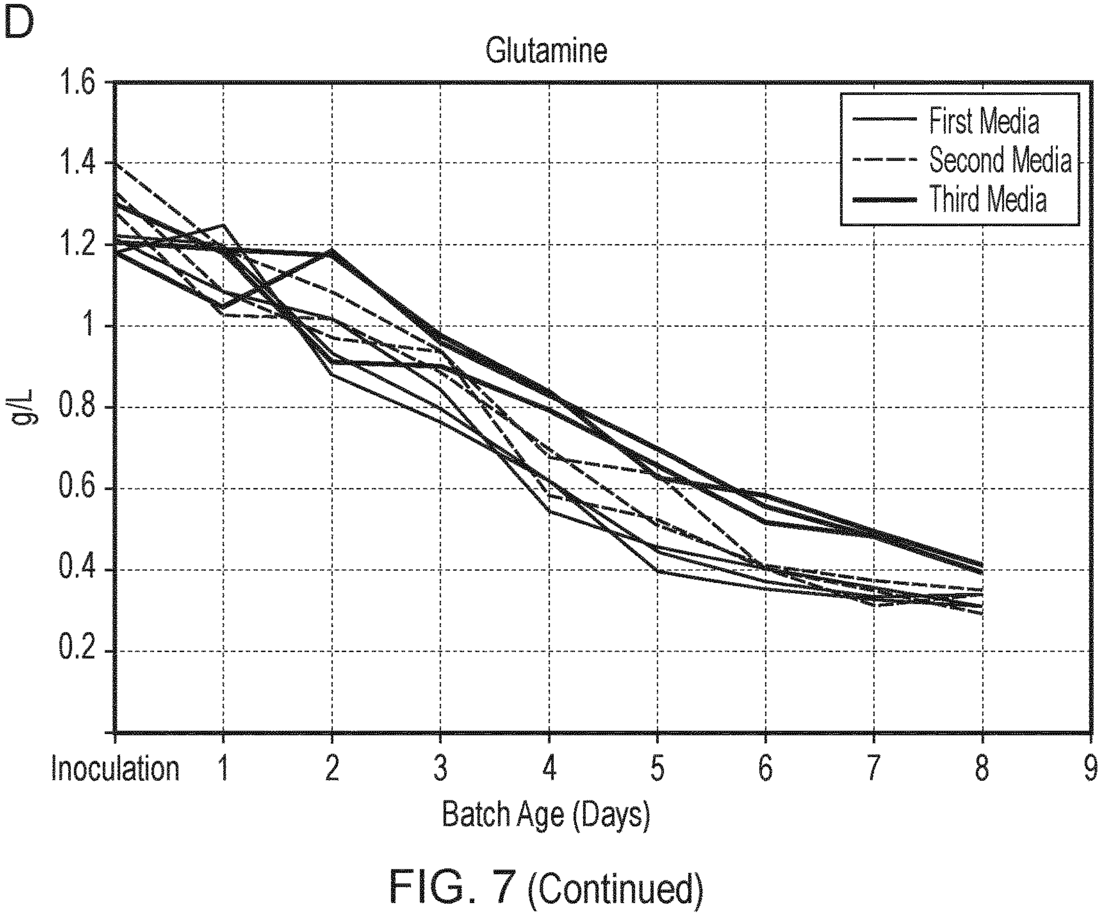

Metabolites (in particular, glucose, glutamine and lactate concentrations) and cell density measurements for an unfed batch culture were simulated using the equations in Karra, Sager and Karim (Computer Aided Chemical Engineering, Vol. 29, 2011, Pages 1311-1315). The initial glucose concentration and model coefficients were adjusted to simulate fed batch behaviour in three different media. White noise was added to the simulated data with a 5% relative standard deviation for the cell density and 7% relative standard deviation for the metabolite concentrations in order to approximate the impact of measurement uncertainty using a Nova Flex Analyzer. The resulting simulated raw cell density measurements are shown in FIG. 7A. The resulting simulated raw metabolite measurements are shown in FIGS. 7B-D.

Fed Batch Culture (Example 2)

Cell line and seed culture: A Cellca DG44 CHO cell line (Sartorius) expressing a monoclonal IgG1 antibody was used in this study. This cell line was selected because the process and the biologic it produces are proven industrially and have been well characterised. The inoculation train started with cryo vial thaw. The cryo vial contained 1 mL CHO suspension at a concentration of 30 million cells/mL. After thawing, CHO suspension was transferred in a 15 mL Falcon™ tube (Sarstedt) with 10 ml pre-warmed (36.8° C.) seed medium. To remove all freezing medium, the suspension was centrifuged at 190 g for 3 minutes at room temperature (Centrifuge 3-30K, Sigma). The supernatant was decanted, and the pellet was re-suspended in 10 mL fresh pre-warmed seed medium. This suspension was transferred in a 500 mL Shake flask (Corning) filled with 150 mL pre-warmed seed medium. Suspension culture was shaken in an incubation shaker (CERTOMAT™ CT plus, Sartorius) at 120 rpm with a shaking amplitude of 50 mm, 36.8° C. and 7.5% $CO_2$ atmosphere. The seed culture was passaged every 3-4 days until inoculation of the production culture (passage 9). Media Preparation: Seed medium (SM) were used for the seed culture and basal medium for production (PM). In addition, two different feeds, Feed Medium A (FMA) and Feed Medium B (FMB) were used. All media were part of the commercially available XtraCHO media platform (Sartorius) and chemically defined. For all components powder were used which was liquefied with water and sterile filtered.

Small-scale Bioreactors: The highly parallel small-scale bioreactor system Ambr™ 250 high throughput with up to 24 disposable cell culture bioreactor vessels were used (Sartorius). The bioreactors have two pitched-blade impellers and an open pipe sparger and the working volume can be in the range of 185 mL and 250 mL. Dissolved oxygen (DO), Temperature (T), pH and gassing are controlled independent for each bioreactor. Air, oxygen ($O_2$) and carbon dioxide ($CO_2$) were used for gassing, whereby $CO_2$ was also used for pH control. Process conditions are described in detail below. The bioreactor system was connected to a computer for performing the calculations needed to operate the bioreactor—which includes, among other things, a value for the liquid volume in the reactors throughout the culture after feed is added to the reactor or samples are drawn from the reactor. The bioreactor system was also connected to a monitor for displaying the current status of the bioreactor's operation.

Process Conditions: Before inoculation, the bioreactors were filled with PM and equilibrated overnight. The DO set point was at 60% and the pH setpoint was maintained using $CO_2$. 20 μl Antifoam C Emulsion (2%, Sigma) was added every 24 hours to prevent foaming. The bioreactors were inoculated from the seed train with a starting concentration of 0.3 million cells/mL allowing for a three-day batch phase followed by a nine-day fed-batch period. The automated discontinuous bolus feed of FMA and FMB respectively was complemented with a glucose feed solution (400 g/L, Merck) to maintain the glucose concentration above 3 g/L. The reactor volume was monitored throughout the bioprocess. Until day 7, all bioreactors were operated with a temperature set point of 36.8° C. and the pH was held at 7.1. After day 7, a full factorial Design of Experiment (DoE) was implemented for Temperature and pH at three levels. The temperature levels were 31.2° C., 34° C. and 36.8° C. The pH levels were 6.9, 7.1 and 7.3. Multiple center-point replicates were run where the temperature was maintained at 36.8° C. and pH was held at 7.1 on days 7 through 12. The remaining batches were each operated at a single Temperature/pH combination for days 7 through 12. The center-point replicates were used for model training of the 'normal' metabolic state, as further explained below. The DoE process was implemented to demonstrate the model prediction capabilities of the present invention, as further explained below.

Figure 8:
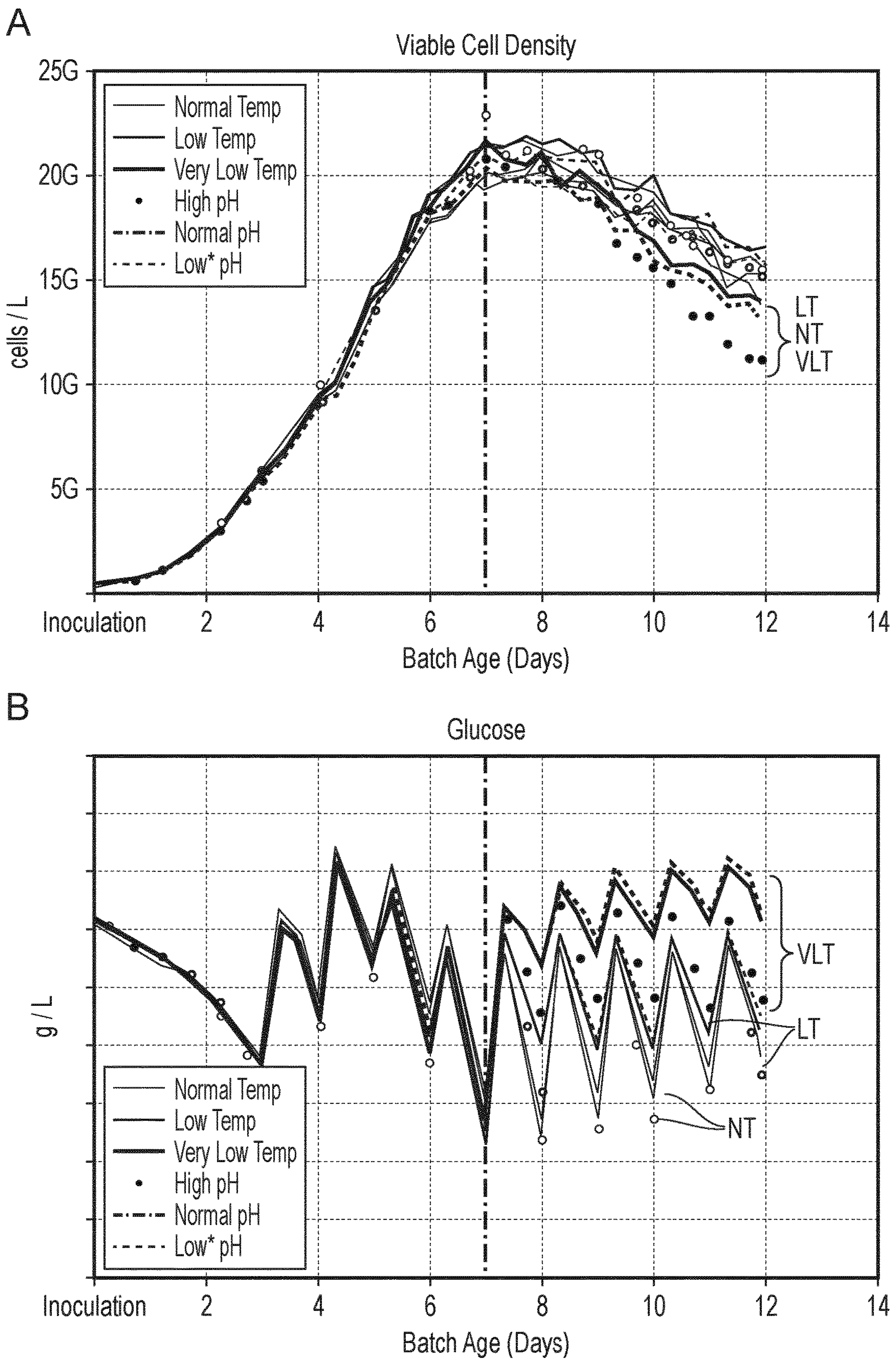
FIG. 8 shows data from multiple sensors as a function of maturity (here shown as batch age in days) in a fed-batch bioprocess run with the same conditions until the vertical line, then using a normal temperature (NT), a low temperature (LT) or a very low temperature (VLT) and different pH (solid lines: normal pH, dashed lines: low pH, dotted lines: high pH). (A) viable cell density data; Glucose concentration (B), Lactate concentration (C) and Ammonia concentration (D) from a FLEX2 sensor; glutamine (E) and glutamate (F) concentration from external NMR.
Figure 8:
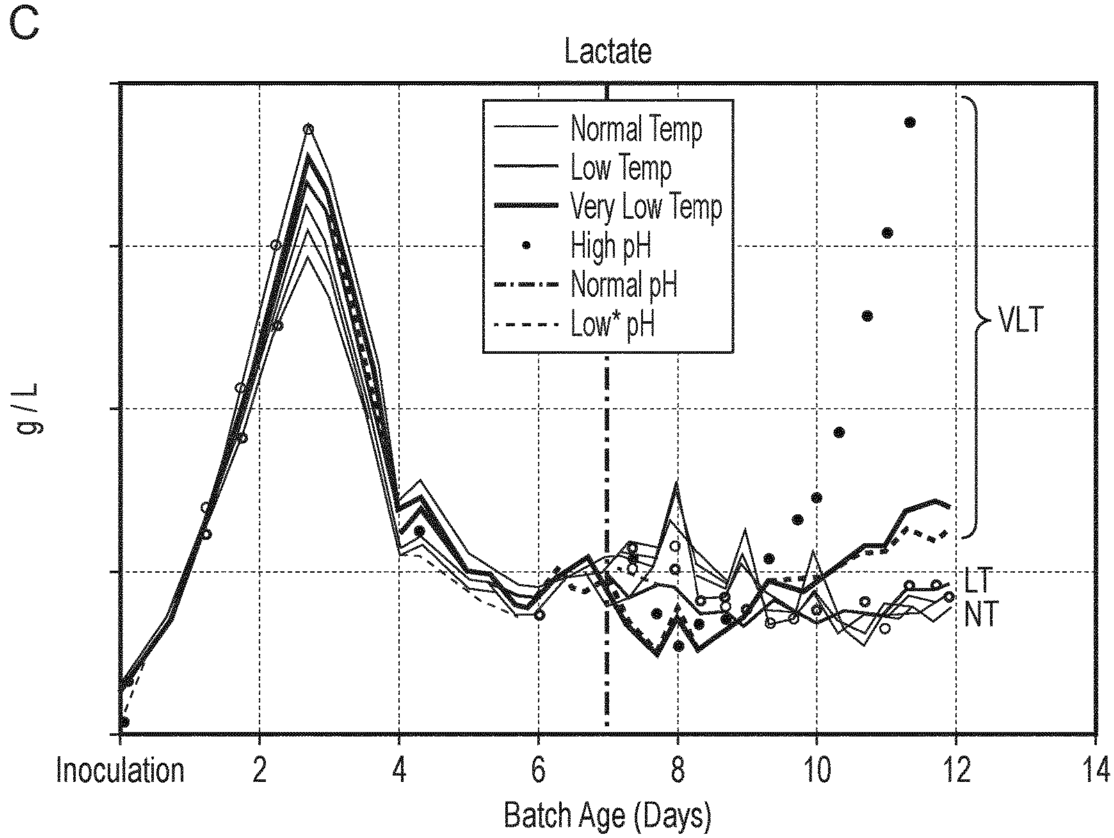
Figure 8:
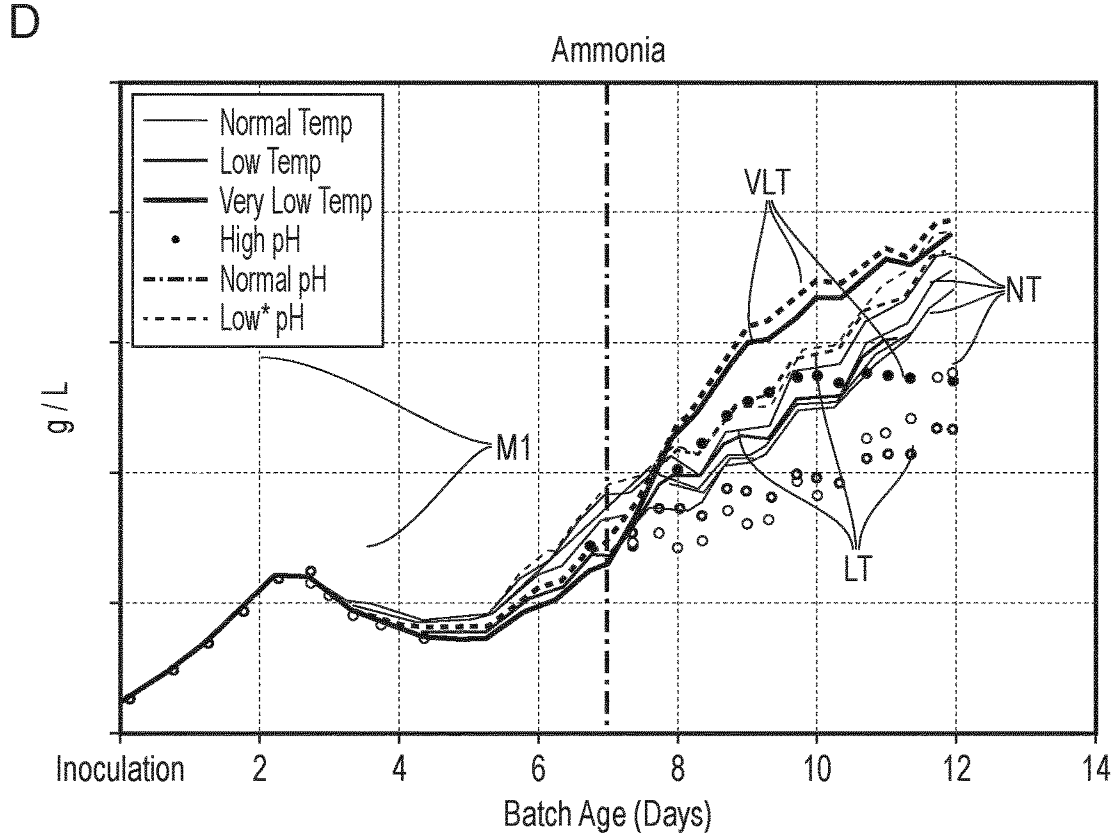
Figure 8:
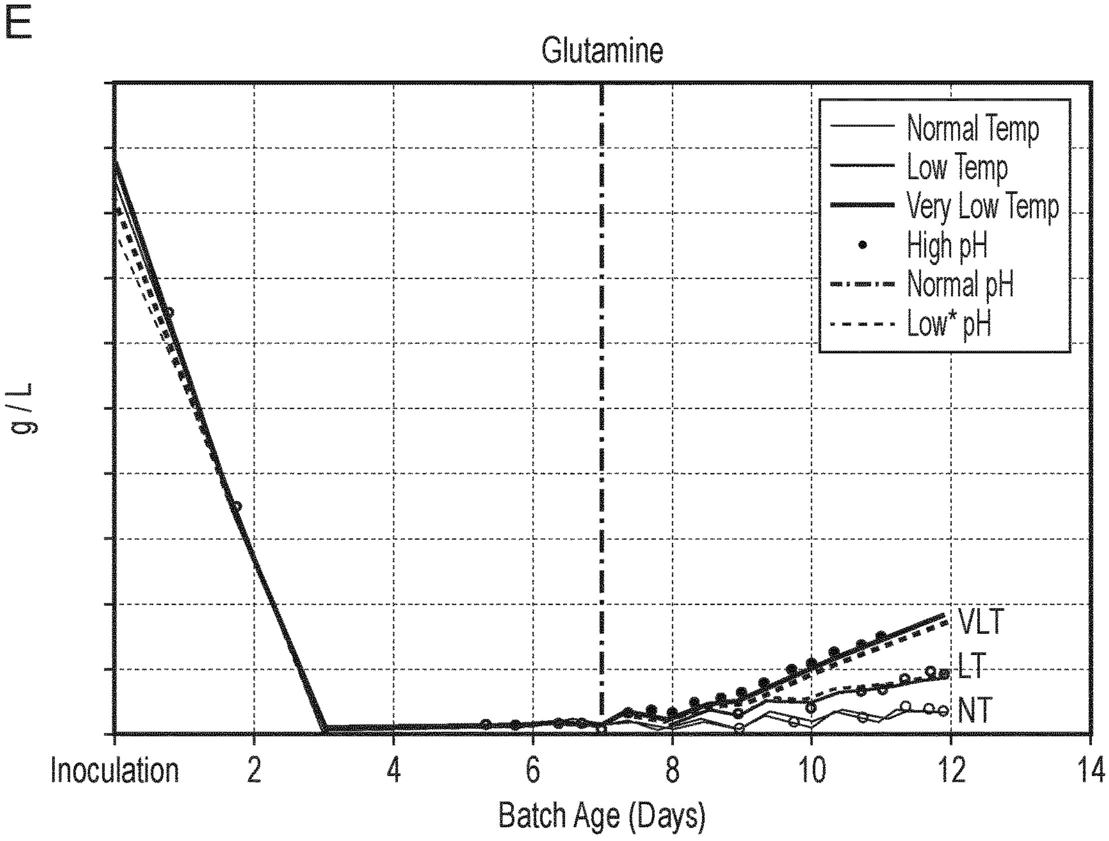
Figure 8:
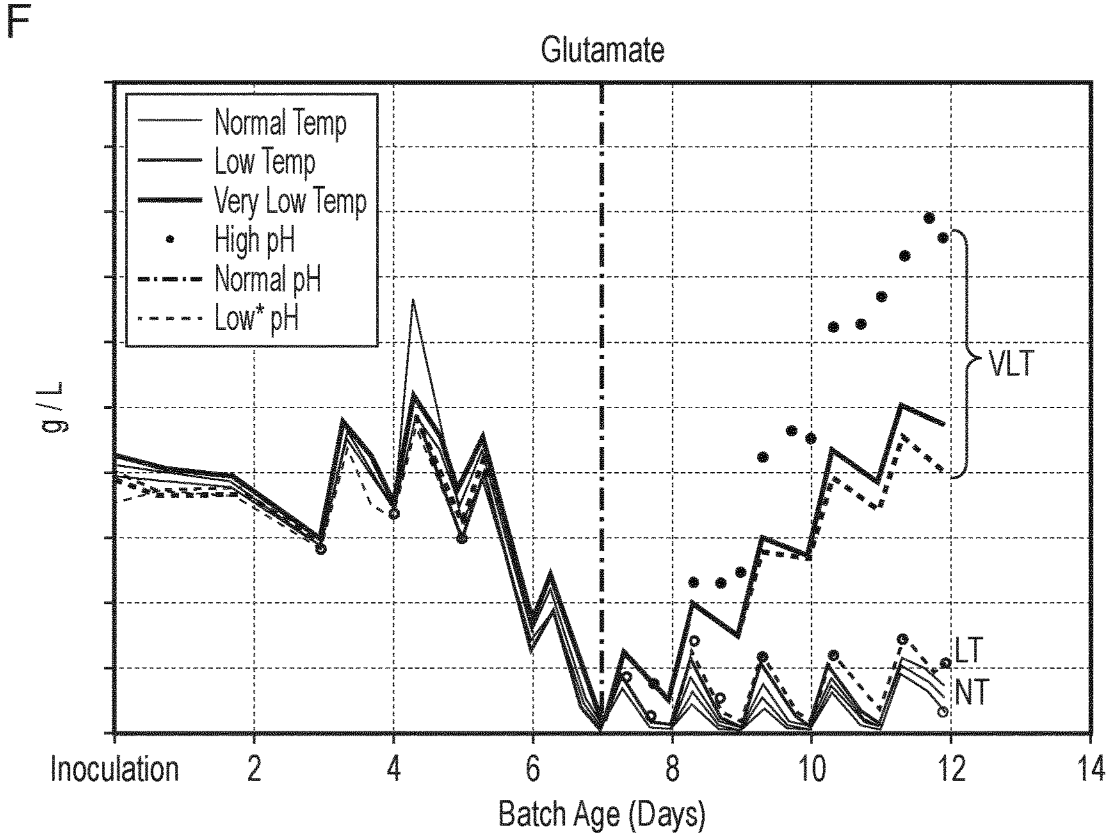

Analytics: In the Ambr™ system up to three samples per day were taken automatically via liquid handler (LH). The LH transferred the cell broth partly to the External Sampling Module (ESM), feeding into the BioProfile™ FLEX2 (Nova Biomedical), and to additional sample tubes for further analysis such as NMR metabolite characterisation. Metabolites such as glucose, lactate, cell parameter such as viable cell density, osmolality, pH and pO2 were analyzed by BioProfile™ FLEX2 (Nova Biomedical). Samples for further analysis were centrifuged at 300 g for 5 minutes at room temperature (Centrisart™ A-14C, Sartorius). The supernatant was filtered through Minisart™ RC4 0.2 μm syringe filters (Sartorius) and stored in the freezer at −80° C. Extracellular metabolites like the amino acids were analyzed via NMR using an external service provider (Eurofins Scientific). The resulting raw cell density measurements from the FLEX2 are shown in FIG. 8A. The resulting raw metabolite measurements are shown in 9B-F from the FLEX2 (glucose, lactate and ammonia) and the external NMR analysis (glutamine and glutamate). Measurements for glucose, lactate, glutamine and glutamate were obtained using both the FLEX2 apparatus and NMR but only one of these is shown on FIGS. 8B-F for each metabolite. In FIGS. 8A-F, the vertical black line indicates the maturity at which the DoE in temperature and pH is implemented. Before the vertical black line, all batches are the same, whereas after the vertical black time different conditions were tested according to the DoE scheme as indicated.

Perfusion Culture (Example 3)

Generic Process Description: Perfusion culture was performed according to a proprietary process. In general, perfusion bioreactors culture cells over long periods, which can extend into months, by continuously feeding the cells with fresh media and removing spent media while keeping cells in culture. The flowrate of fresh medium (feed flow) is typically one of the process conditions that is controlled and/or known (such as e.g. fixed or measured), as is the composition and physical characteristics (e.g. density) of the fresh media. The flowrate of spent medium is also typically controlled and/or known (such as e.g. fixed or measured). In perfusion there are different ways to keep the cells in culture while removing spent media. One way is to keep the cells in the bioreactor by using capillary fibers or membranes, which the cells bind to. Another does not bind the cells, but rather relies on filtration systems that keep the cells in the bioreactor while allowing the media to be removed. Another method is the use of a centrifuge to separate cells and return them to the bioreactor.

Analytics: cell density measurements and metabolite concentration measurements were obtained here using a Nova Flex Analyzer in a similar way as described above in relation to the unfed and fed-batch processes. The reactor volume was also monitored.

Parsing and Preprocessing Module

The primary purpose of the parsing and preprocessing module is to align the different measurements to a common set of maturities (time in all of the present examples). An optional part of the module is to smooth the data so that future calculations will be more accurate. An algorithm was employed here which accomplishes both goals in a single step. This was developed in house using Python 3.6. Any method for aligning the measurements to a common set of maturities could be used. These include, for example, linear interpolation, zero-order hold, etc. Similarly, any smoothing algorithm may be applied, including for example a moving average, Savistsky-Golay, etc. For example, the Savitsky-Golay algorithm uses the linear least squares method to fit successive sub-sets of adjacent data points with a low-degree polynomial. Where one or more functions are fitted to the data, such as e.g. using the Savistsky-Golay algorithm, missing values and smoothed values can be obtained from the fitted functions. This is the type of approach that was used in Examples 2-3 below.

Material Balance Module

A generic upstream cell culture process grows cells to produce a product that results from the cells metabolic processes; a generic diagram of these processes is shown in FIG. 1B. The concentration of the cells, also known as Viable Cell Density, in the reactor 2 is labeled VCD. The cells are grown in a reactor 2 of volume V. The media inside this vessel has density, p, and it is comprised of nutrients that are used by the cells to grow, and also metabolic byproducts that have been secreted into the media by the cells; the concentration of all these metabolites is labeled [Met] where Met can be glucose, lactate, etc. As described thus far, the diagram represents all three process types used in Examples 1-3. However, the fed-batch (Example 2) and perfusion (Example 3) processes have a few additional considerations. If applicable, a feed stream 24 is used to supply additional media to the bioreactor. The mass (or volume) flow rate of material into the reactor is $F_F$. The density of the feed media is labeled $\rho_F$ and the concentration of metabolites in the feed media is labeled $[Met]_F$. If applicable, a bleed stream 26 can be used to control the cell density inside the bioreactor by draining cell rich media from the bioreactor out of the culture while cell free media is being fed into the bioreactor. The bleed stream is characterised by the same three factors as the feed stream, which are subscripted here with a B instead of an F. It is also characterised by one additional factor, the viable cell density in the bleed, $VCD_B$. If applicable, a cell retention device 28, for example an alternating tangential flow filtration (ATF) system can be attached to the bioreactor. Here, the auxiliary harvest stream brings cell rich media from the reactor to the cell retention device, the cell free media can then be removed in a harvest stream 28A that continuously removes product from the system for purification; an auxiliary return stream 28B then returns the leftover media and concentrated cells back to the bioreactor. The harvest stream is characterised by the same parameters as the bleed stream and are subscripted with the letter H. The two auxiliary streams (auxiliary harvest stream and auxiliary return stream) could also be characterised like all other streams, and corresponding terms added to the mass balance equations. In example 3, only a harvest stream 28A was modeled as the material in this flow truly leaves the system (i.e. the harvest flow contains the part of the auxiliary harvest stream that leaves the system), whereas the material in the auxiliary return flow does not.

Generically, the material balance described by Equation (7) is used to determine the amount of metabolite consumed or secreted by each cell. Equation (7) can equivalently be written as:

$$\begin{bmatrix}\text{Total change of}\\ \text{metabolite mass}\\ \text{in reactor}\end{bmatrix} = \begin{bmatrix}\text{Total mass flow}\\ \text{of metabolite}\\ \text{into reactor}\end{bmatrix} + \begin{bmatrix}\text{Total mass flow}\\ \text{of metabolite}\\ \text{out of reactor}\end{bmatrix} + \begin{bmatrix}\text{Total mass of metabolite}\\ \text{consumed or secreted by}\\ \text{all cells in reactor}\end{bmatrix} \tag{7a}$$

Based on the system shown in FIG. 1B, this takes the form of Equation (8) were qMet is the specific metabolite transport rate, assuming that the auxiliary streams can be ignored and that the harvest stream does not contain cells (i.e. that the retention device 28 is perfect). In this formulation, if qMet is negative, the metabolite is being consumed and if it is positive then it is being produced. Equation (8) can be expressed and solved for each of the types of cultures used in these examples, as explained below in relation to Examples 1-3.

Systems Biology Module

Constraint Based Methods: We can consider cells to be small biological factories where the cells' internal metabolism represents the factories operational state. As an example, a cell factory defined by the central carbon metabolic pathways shown in FIG. 14 (available at https://escher.github.io/#/app?map=e_coli_core.Coremetabolism&tool=Builder&model=e_col i_core) uses glucose as a raw material to feed into the assembly lines defined by glycolysis and the pentose phosphate pathway in order to create potential energy and intermediate building blocks needed for the cell factory's operation. The metabolic enzymes that are encoded in the cells' genome, and their associated specificities, define the chemical reactions responsible for the interconversion of metabolites. Generating a genome scale map of these reactions, or a subset thereof, provides a description of all the assembly lines that could possibly be operating inside the cell factory, or at least a subset of assembly lines necessary to model specific characteristics of the cell factories operation.

The chemical reaction stoichiometries, S, define a system of equations that relate the internal metabolite concentrations, m, to the reaction rates (also known as fluxes), v, as shown in Equation (4). In order to model a phenotypic behavior of interest, a mathematical description of the cell's objective, Z, is used. For example, the cell factory may strive to produce new DNA, maximize ATP generation, maximize biomass produced per unit of ATP, maximize protein production rate, etc. The macromolecular structure of DNA is comprised of intermediate building blocks that are created by the cell factory's assembly lines. Specifically, a certain amount of the nucleotide precursor ribose 5-phosphate needs to be created by the pentose phosphate pathway in order to construct the DNAs nucleotide structure. This provides the mathematical link between the phenotypic behavior of interest, such as DNA replication rate, and the internal metabolic condition of the cell that is being modeled, x, such as the ribose 5-phosphate production rate. This takes the form of an optimization problem like the one shown in Equation (3) where the coefficients $\alpha$ and $\beta$ describe the linear and nonlinear impact of x on the cells objective, Z.

In order to avoid making spurious predictions about cellular behavior, additional constraints can be added to the model that describe the metabolic state of the cells under real conditions. To this end, metabolite uptake rate data is included in the models to define the quantity of raw materials available to the cell factory. For example, the rate of bringing glucose into the cell factory places an upper limit on the rate of creating ribose-5-phosphate, which in turn places an upper limit on the rate of creating new DNA. Similarly, byproduct (or product) secretion rates data can be included in the models to define the quantity of raw materials that is lost and unable to be used for accomplishing the cells objective. In other words, the specific transport rates that have been determined by the materials balance module can be used to set constraints on the metabolic model. Constraints can be set on any internal reaction rates (e.g. based on heuristics or prior knowledge about the reactions), as well as any uptake/secretion rate. These constraints can be used to apply upper and lower boundaries to the fluxes as shown in Equation (5), i.e. for each of the i and j reactions where these boundaries are known, we can set:

$$\forall i,\text{lower bound}_i \le v_i \tag{5a}$$

$$\forall j, v_j \le \text{upper bound}_j \tag{5b}$$

In general, equation (3) may be solved, subject to the constraints in Equations (4) and (5) (or (5a), (5b)) to estimate the internal metabolic state of the cells.

Figure 14A:
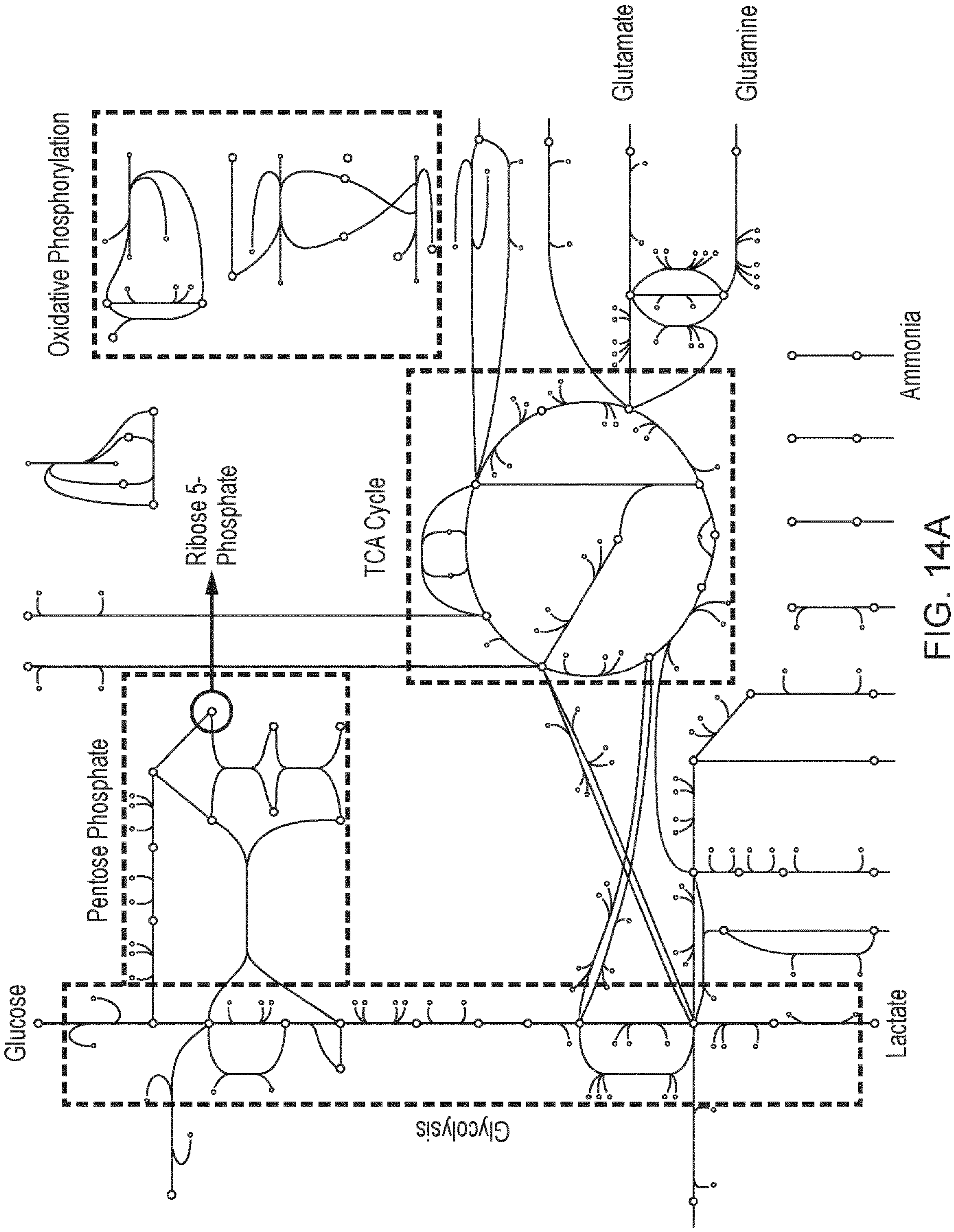
FIG. 14 shows an exemplary metabolic pathway map (also referred to herein as metabolic network) for a central-carbon model with selected pathways and metabolites highlighted; (A) overview of the metabolic pathway map; (B)-(C) close up views of sections of the map in (A)
Figure 14B:
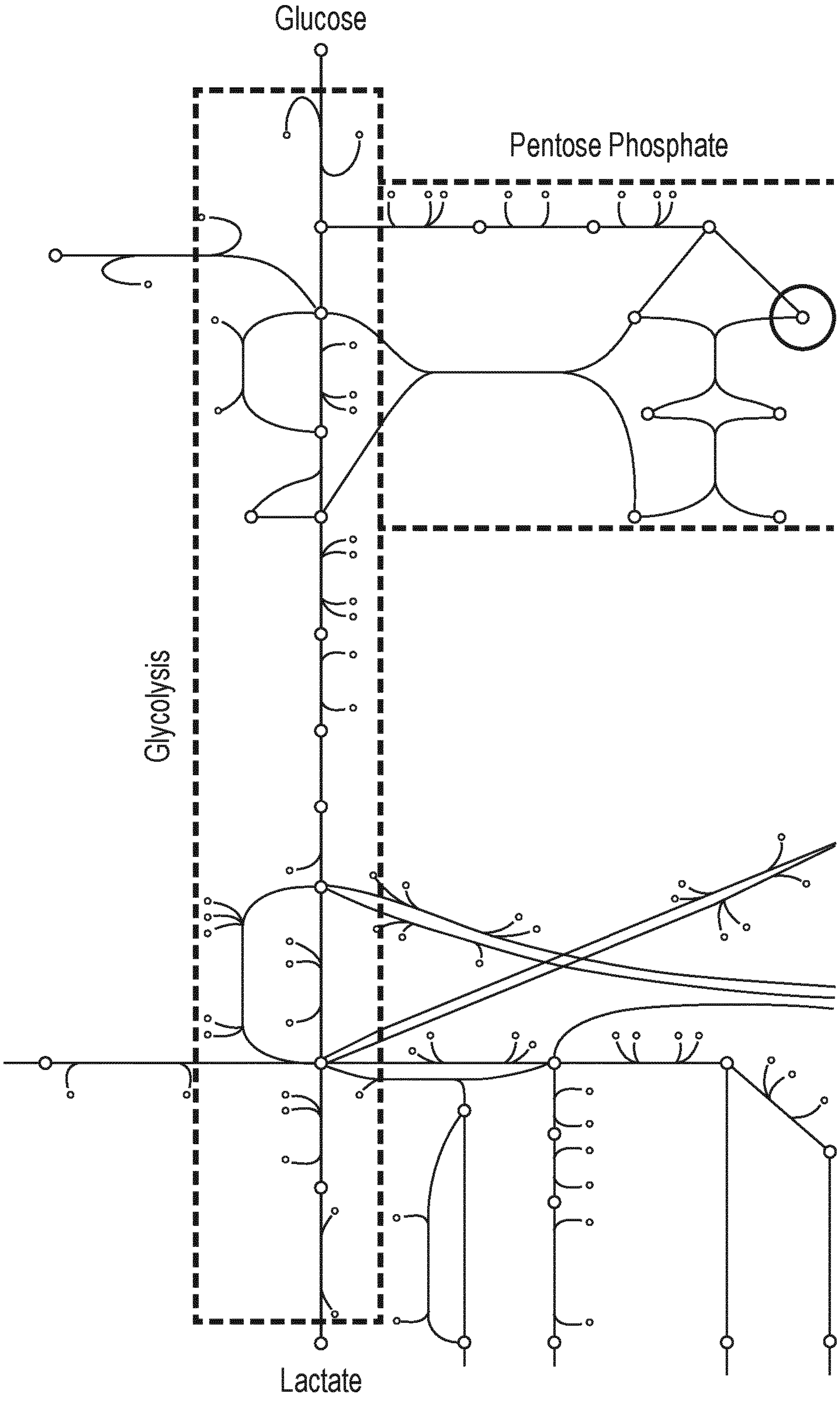
Figure 14C:
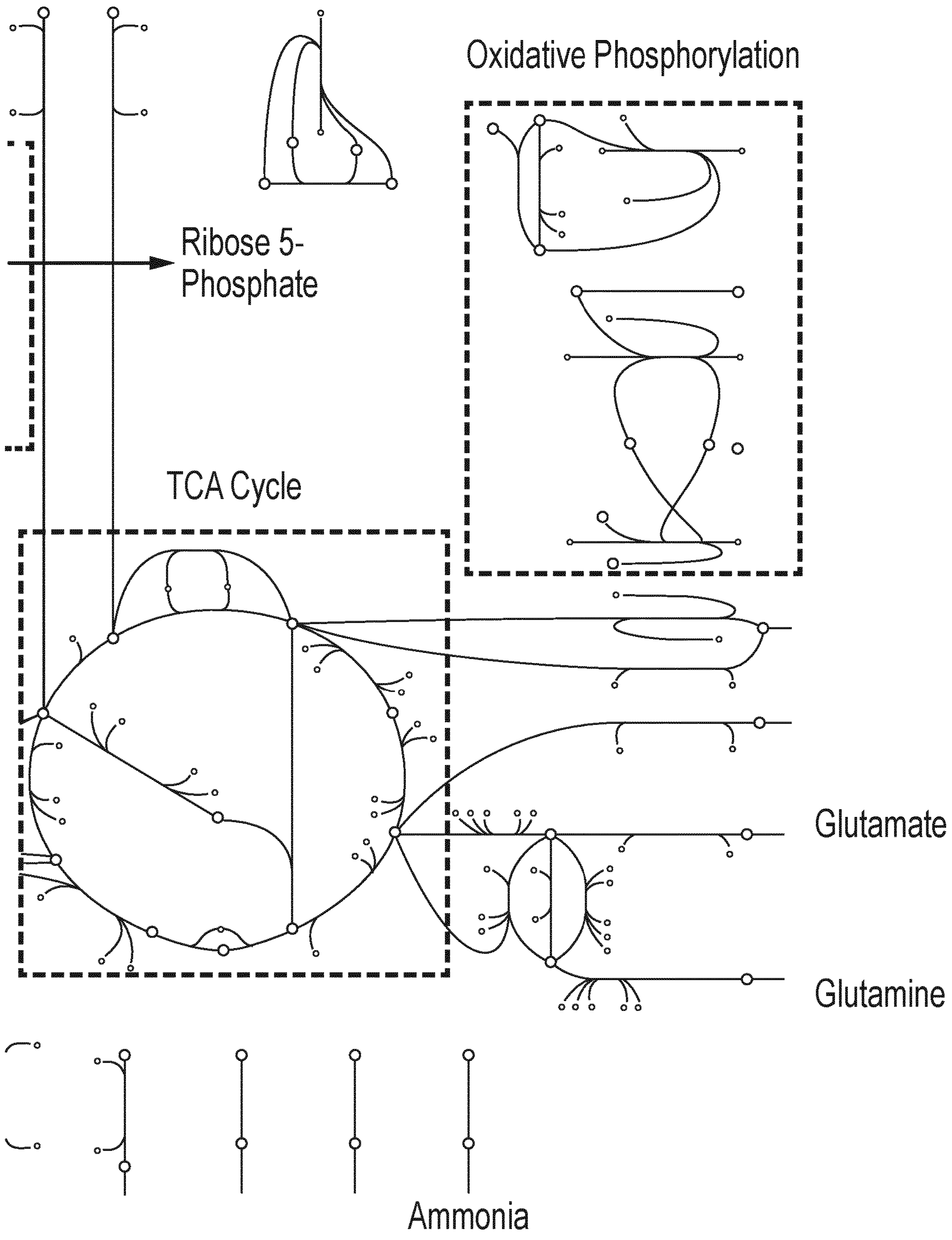

In the examples below, S was defined using the 94 reactions in the central carbon metabolism pathway map shown in FIG. 14, and a pseudo reaction for biomass (leading to a total of 95 reactions represented in S).

Flux balance analysis: In order to simplify the process of solving the optimization problem outlined above, a few assumptions can be introduced. First, a Pseudo Steady State Hypothesis can be applied, under which the metabolite transport rates change an order of magnitude slower than the internal reaction rates. Therefore, the change in metabolite concentrations do not change (equation (4a)), i.e. S*v=0.

From an evolutionary perspective, it can be argued that a good 'objective' for the cells is to divide. The corresponding objective of the cell factory is to build a second cell factory from scratch. This requires the original cell factory to build, among other things, new membranes for the second factories walls, new enzymes for the second factories assembly lines and new DNA so that the second factory has a set of standard operating procedures to follow as well. Just as the DNA requires the precursor Ribose 5-Phosphate to be produced, each of these macromolecules are comprised of intermediate building blocks that are created by the original cell factory's assembly lines. Therefore, we can use the objective function defined in Equation (3) as $$\max_{v} Z = v_{biomass} \quad (3a)$$

where $v_{biomass}$ is the rate of production of biomass according to a pseudo reaction that expresses the relationship between the metabolites assumed to be necessary for the production of biomass (e.g. metabolic precursors for DNA, proteins, etc., energy, water, etc.), the biomass produced and any by-products of the biomass production (e.g. in terms of mass fractions, $\gamma_i$, defining the relative amounts of metabolites involved in biomass production). Therefore, the optimization problem is that of finding the vector of fluxes $v_i$, that result in the maximum value for the singular flux represented by the biomass pseudo reaction. Finally, we take the metabolite transport rates determined by the material balance module, and use them to constrain the solution space to only include flux distributions where these transport rates are within 30% of their measured values as shown in Equation (5c):

$$0.7 * q\text{Met}_j \leq v_j \leq 1.3 * q\text{Met}_j \quad (5c).$$

Figure 13:
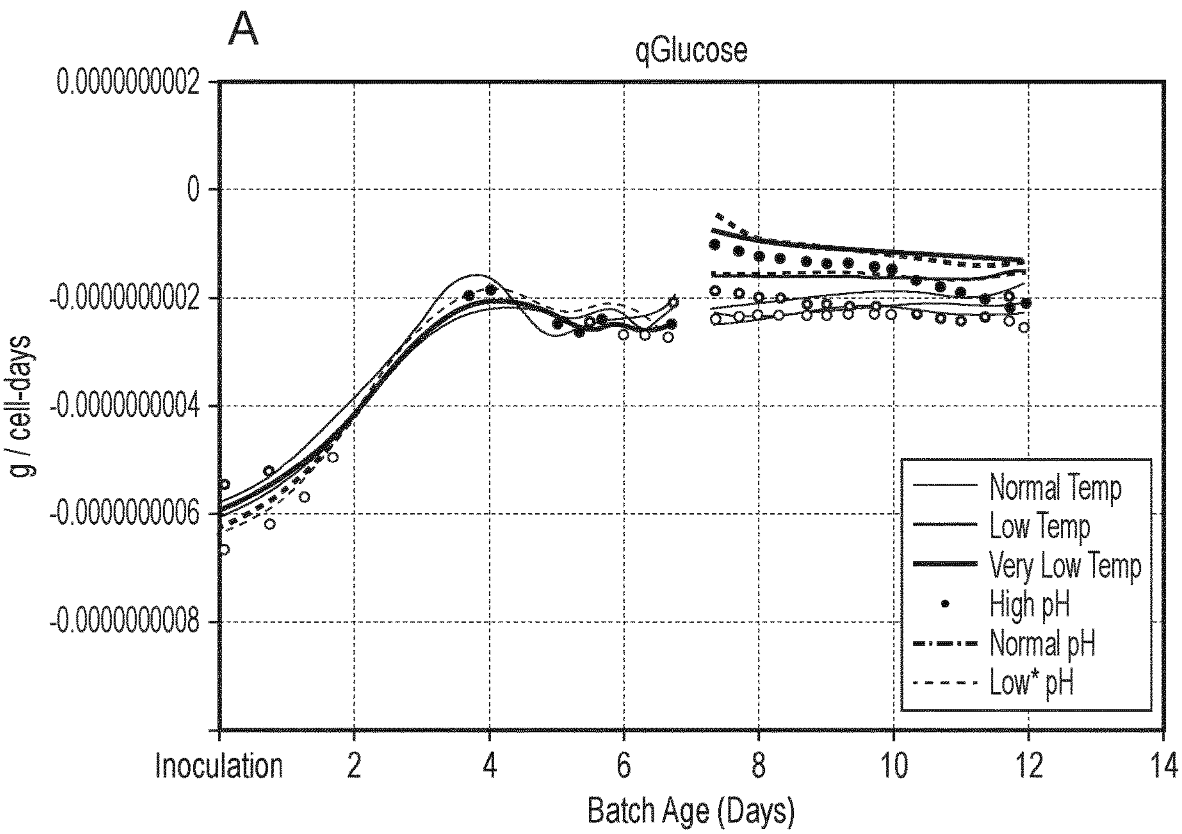
FIG. 13 shows calculated specific transport rates for the fed batch data shown on FIGS. 8 and 11; (A) calculated specific transport rates for Glucose, (B) calculated specific transport rates for Lactate, (C) calculated specific transport rates for Ammonia, (D) calculated specific transport rates for Glutamine, (E) calculated specific transport rates for Glutamate.
Figure 13:
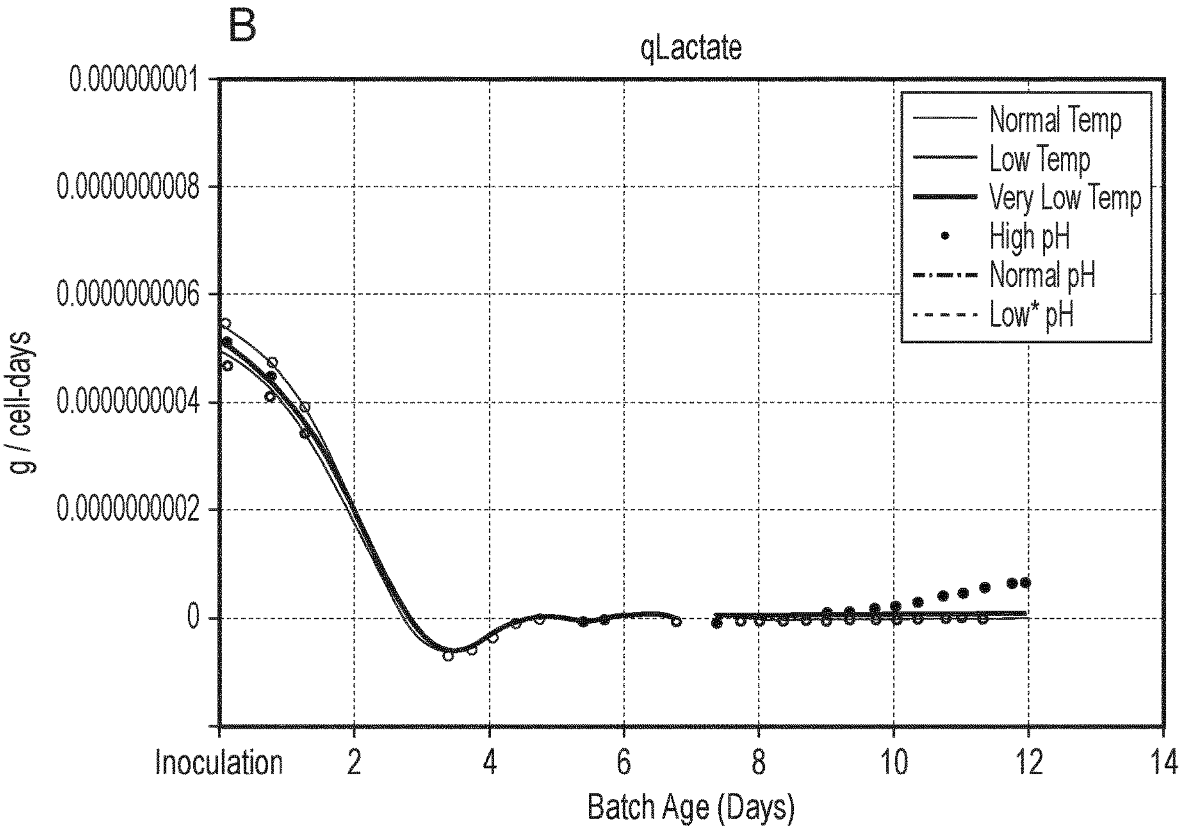
Figure 13:
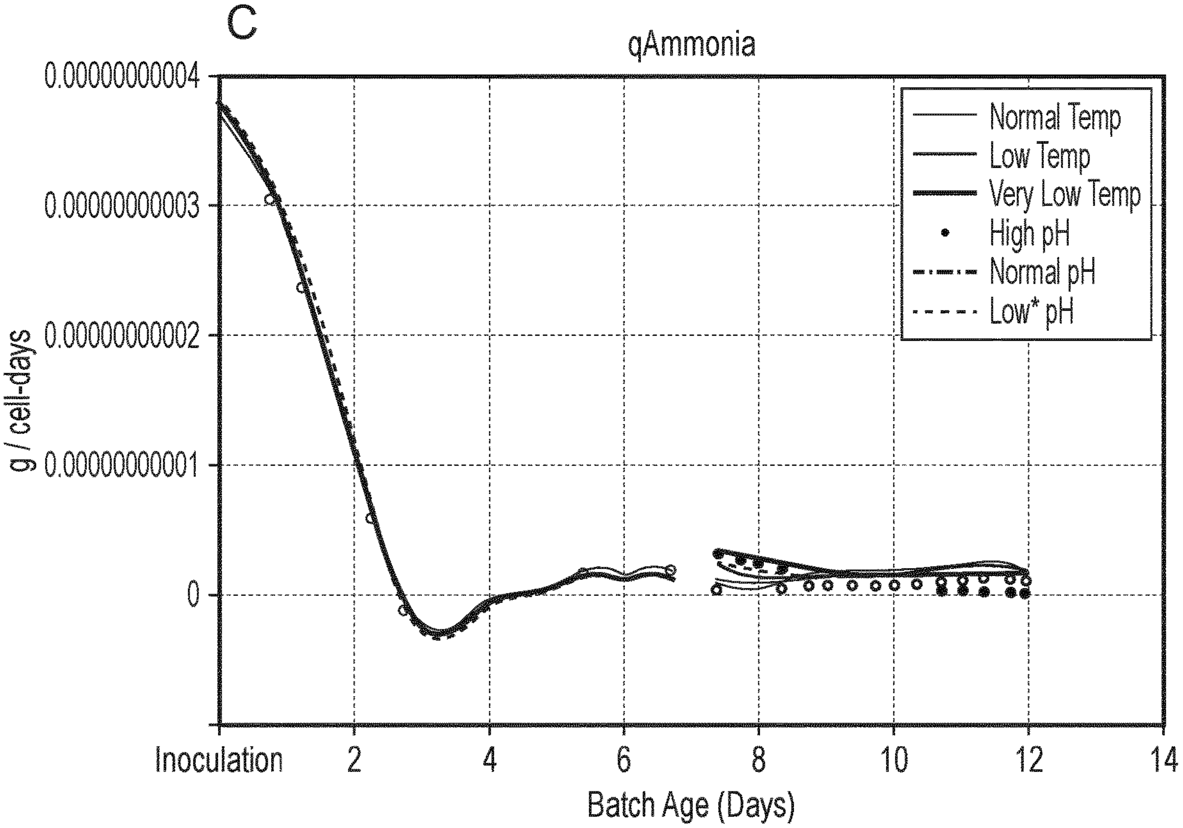
Figure 13:
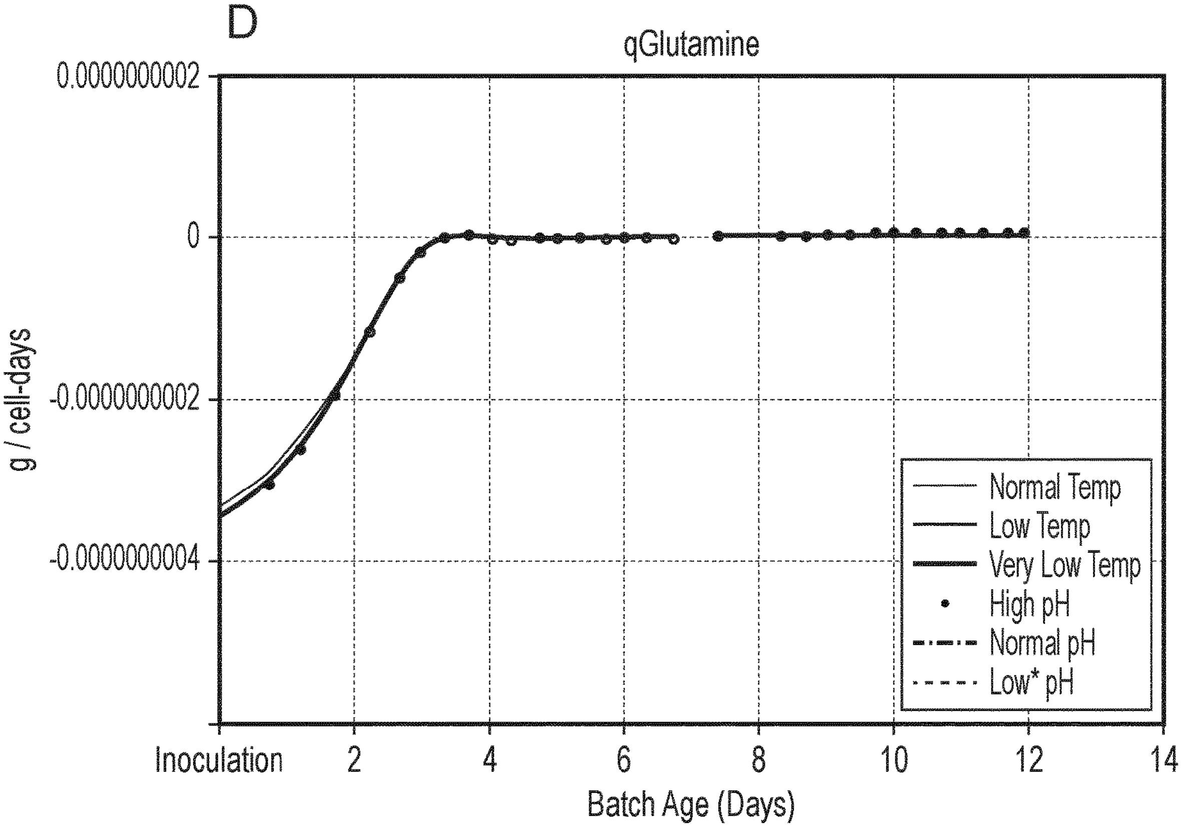
Figure 13:
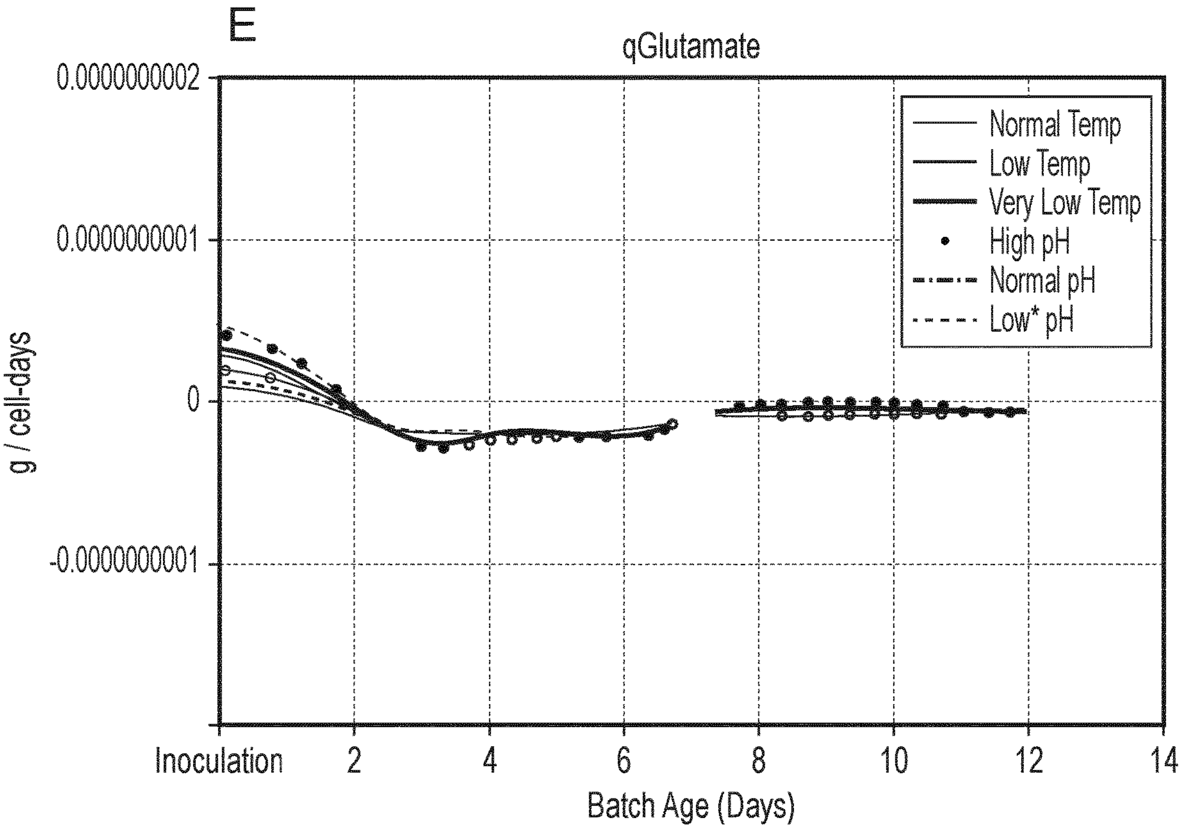
Figure 15:
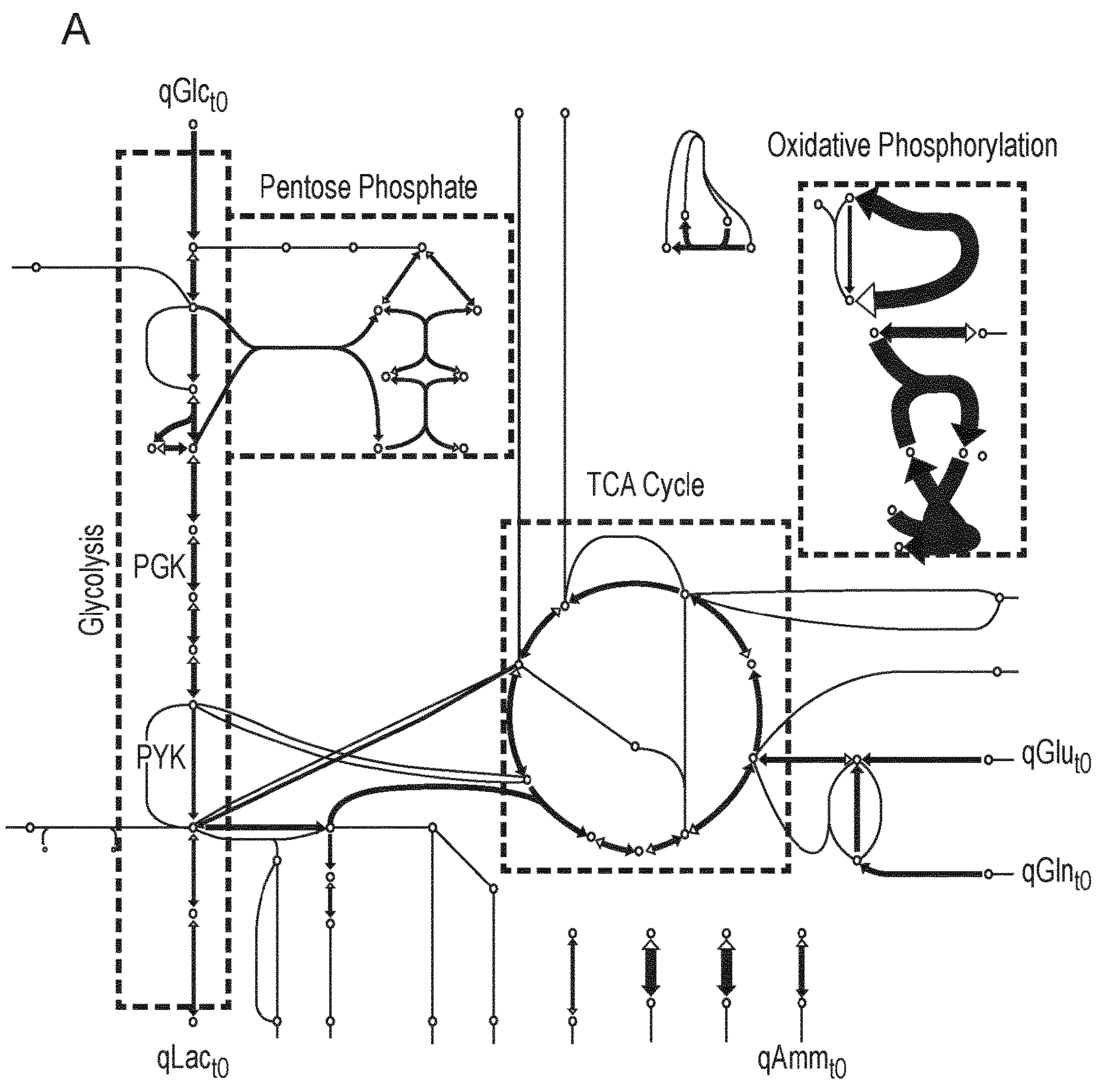
FIG. 15 shows the results of a single flux balance analysis using the data from FIG. 13 (fed batch) at time point t(0) (A) and the corresponding data (B) that was used to constrain the flux balance analysis model; on figure A, the highlighted lines show reactions where there is a non-zero flux, and the thickness of the lines is proportional to the value of the reaction rates.
Figure 15:
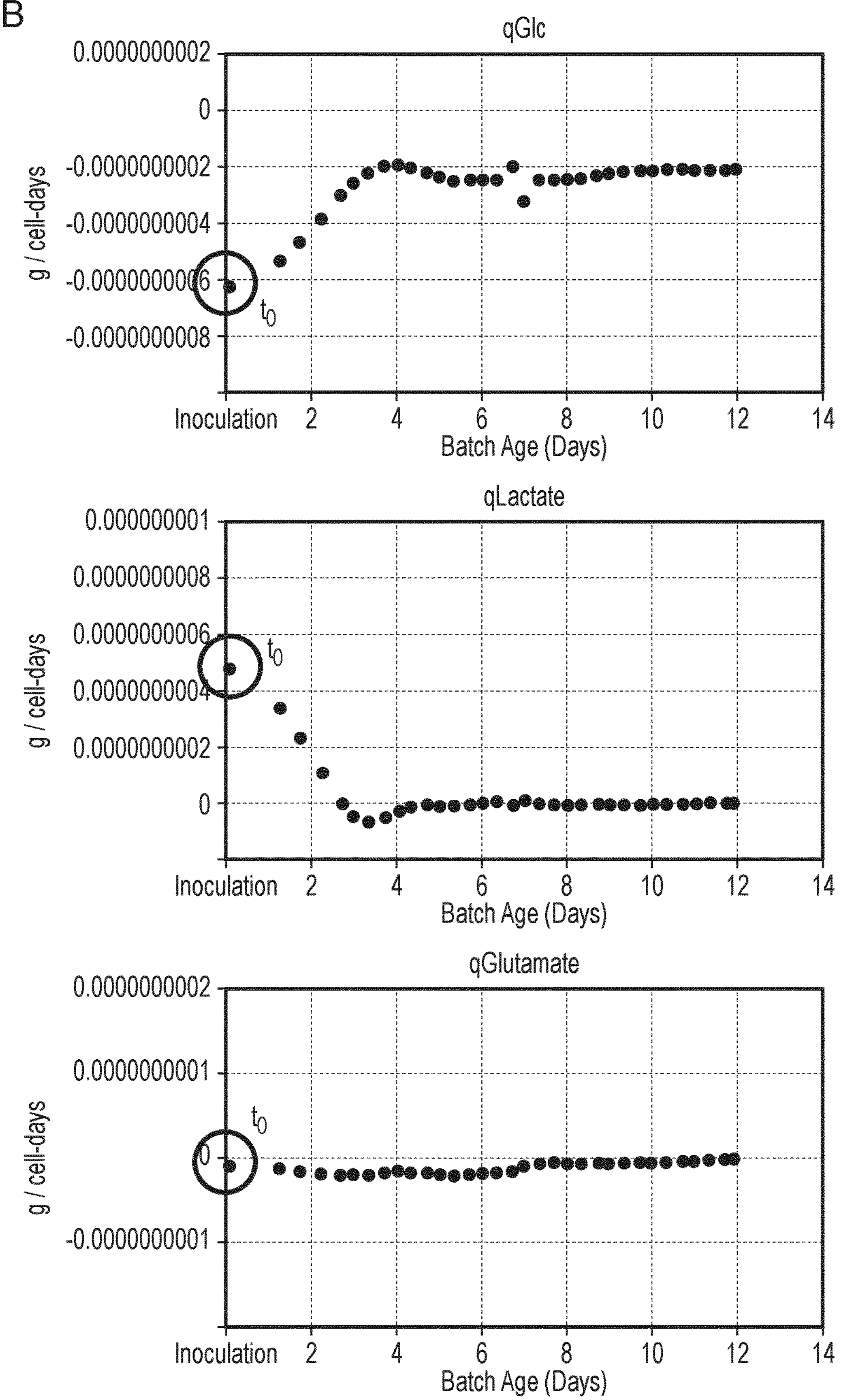
Figure 15:
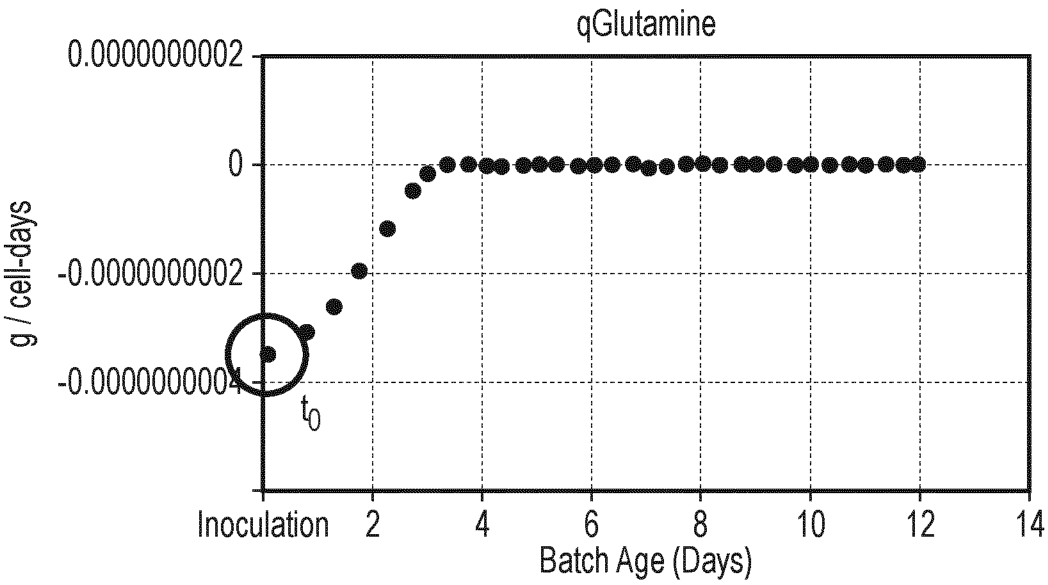
Figure 15:
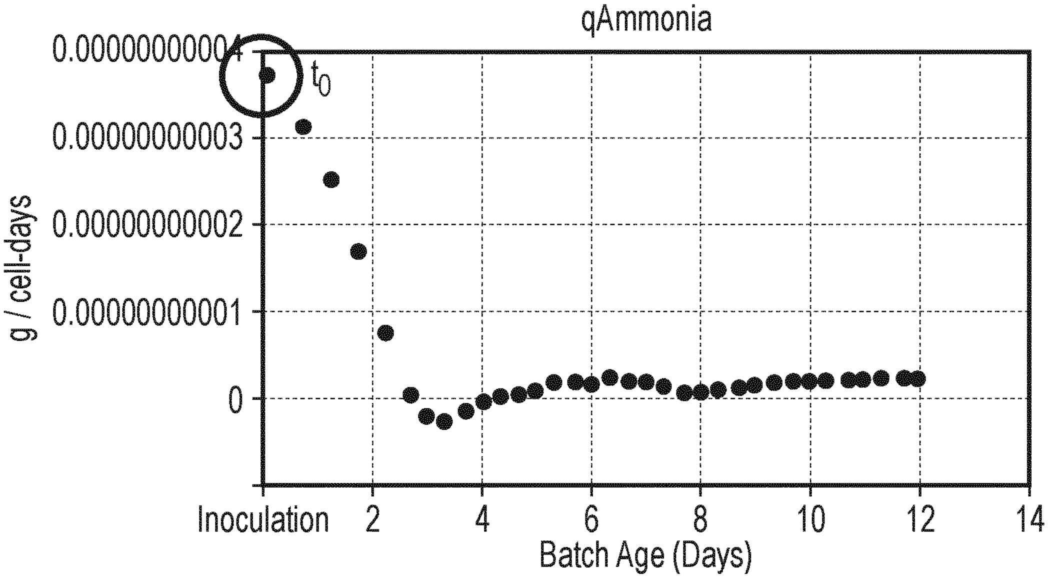

At every single time-point, we then solve Equation (3a), subject to the constraints in Equations (4) and (5c), in order to find all reaction rates, v, for the respective point in time. For the first time point from one of the normal batches metabolite transport rates shown in FIG. 13, the resulting flux distribution is shown in FIG. 15A. The 5 individual reaction rate used to constrain Equation (5c) are also labeled on the boundary of FIG. 15A and their values are highlighted in FIG. 15B. The optimization problem was implemented using the COBRA toolbox in MATLAB (Mathworks).

After obtaining the flux distribution, it is possible to calculate additional information about the cell state. For example, the total amount of ATP generated by the cells can be calculated by summing up the reaction rates of all reactions that are producing ATP, such as the PGK and PYK reaction labeled on FIG. 15A.

Dynamic monitoring of cell metabolism: In the same way that a single flux distribution was obtained for to in FIG. 15, the flux distribution is found for additional time points in a bioprocess by applying Equation (3a) subject to the constraints in equations (4) and (5c) with the j metabolite transport rates in Equation (5c) being altered to reflect the current time point where a flux distribution is being obtained. In the examples below, the stoichiometric matrix S and the optimization function (Equation (3a)) used for every time point was the same. However, in other embodiments, the stoichiometric matrix S and/or the optimization function (Equation (3)) may be chosen independently (and hence may differ) at every time point. For example, different stoichiometric matrices S may be used at different time points when a metabolic network is constructed from different data (e.g. transcripts) at different time points. As another example, the optimization problem may be modified to reflect different objectives Z depending on the culture phase, such as e.g. maximizing biomass during growth phase and maximizing protein production during stationary phase.

Multivariate Analysis Module

Figure 16:
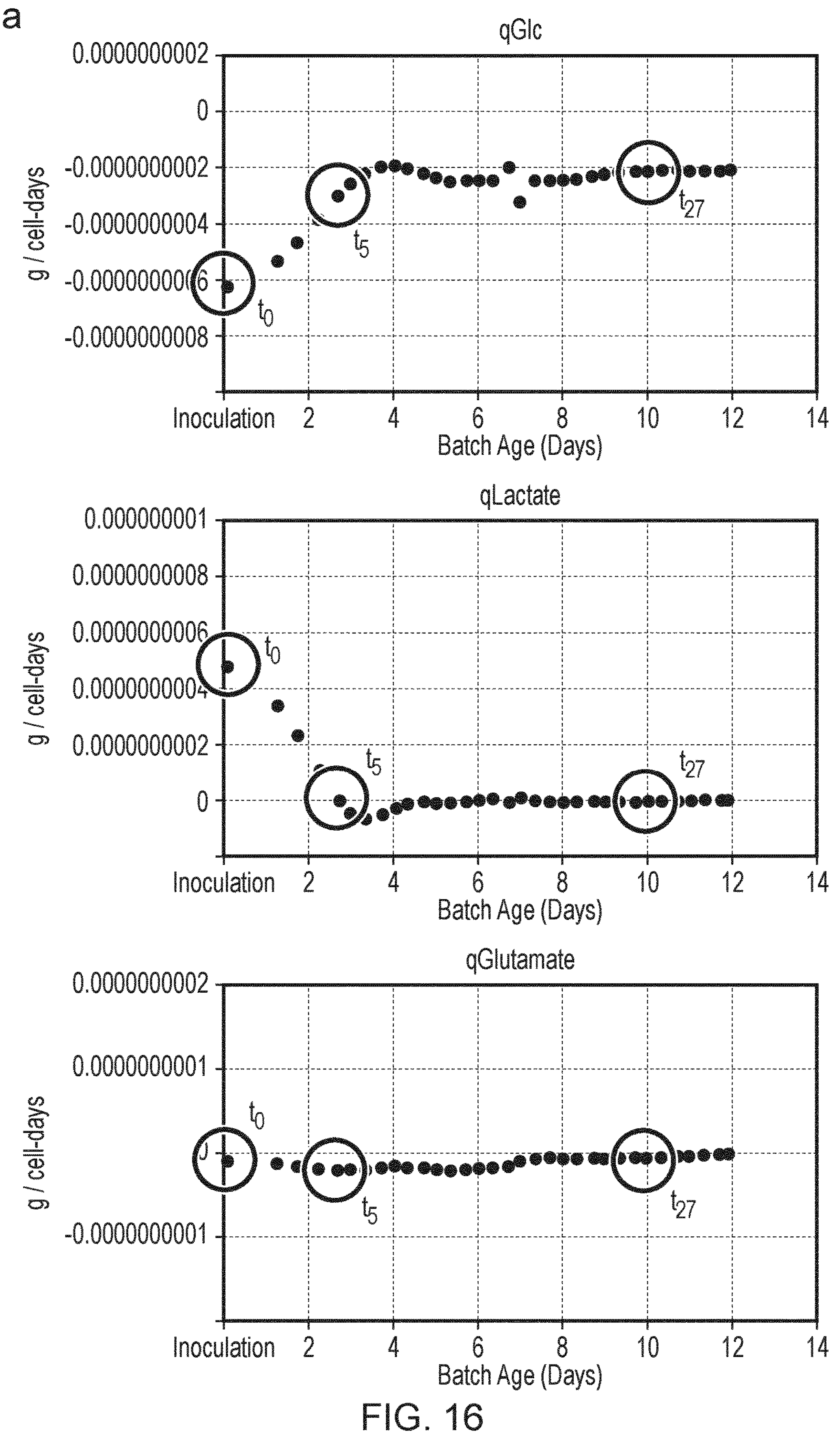
FIG. 16 shows the results of repeated flux balance analyses using the data from FIG. 13 (fed batch) at time points t0 (day 0, as in FIG. 15), t5 (day 3), and t27 (day 10) (B, C and D, respectively), the corresponding data (A—specific transport rates as on FIG. 13) that was used to constrain the flux balance analysis model at each of the indicated time points, and the total rate of generation of ATP (E—for one batch, and F—for all batches) derived from the rates obtained in the flux balance analyses; on figures B-D, the highlighted lines show reactions where there is a non-zero flux, and the thickness of the lines is proportional to the value of the reaction rates.
Figure 16:
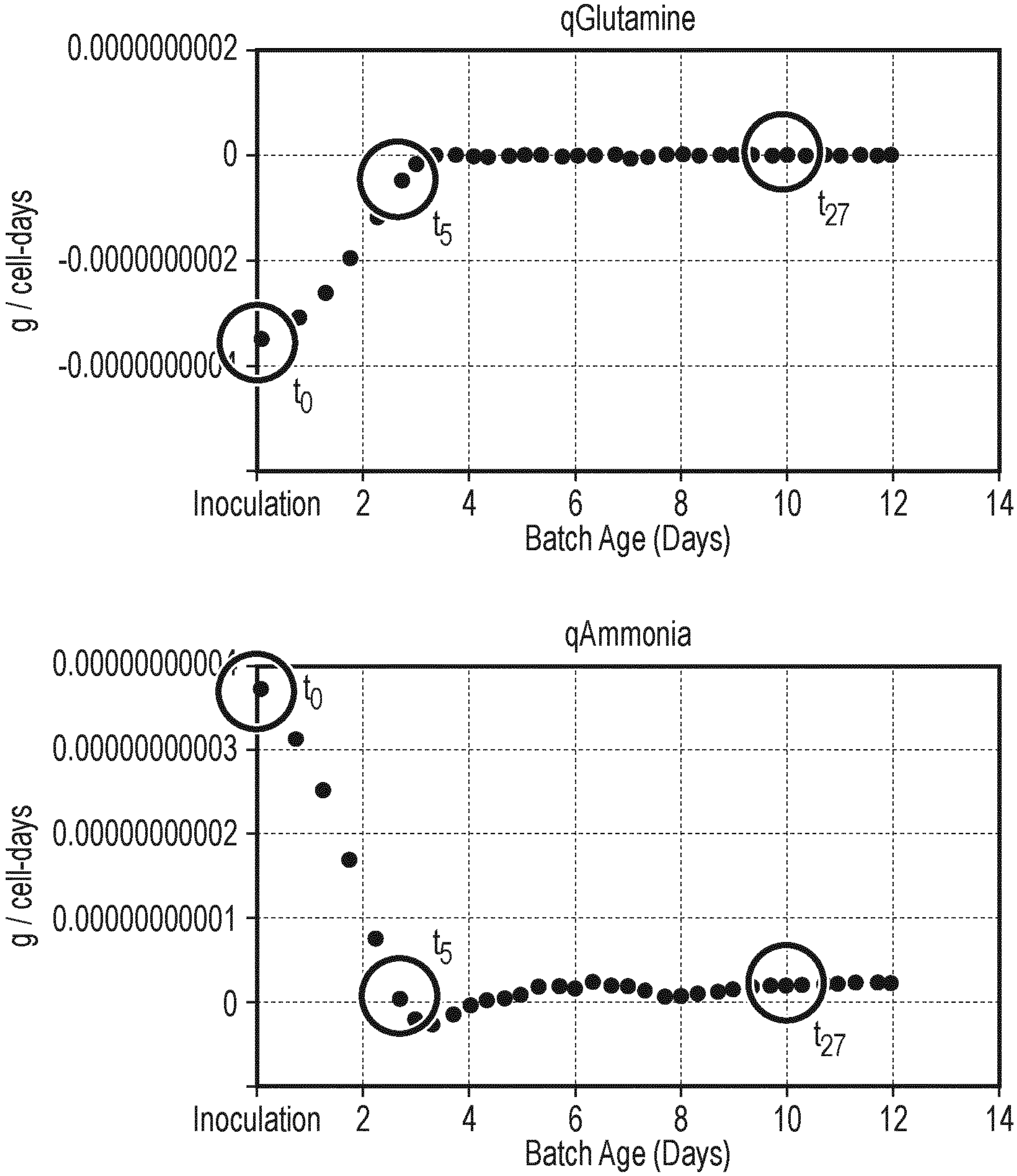
Figure 16:
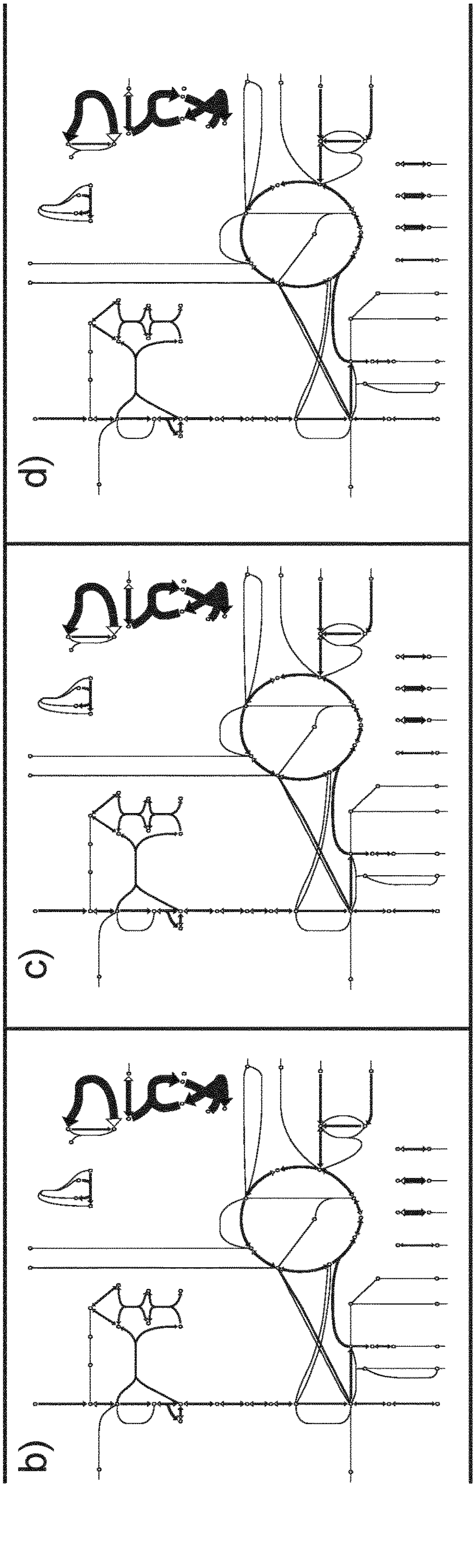
Figure 16:
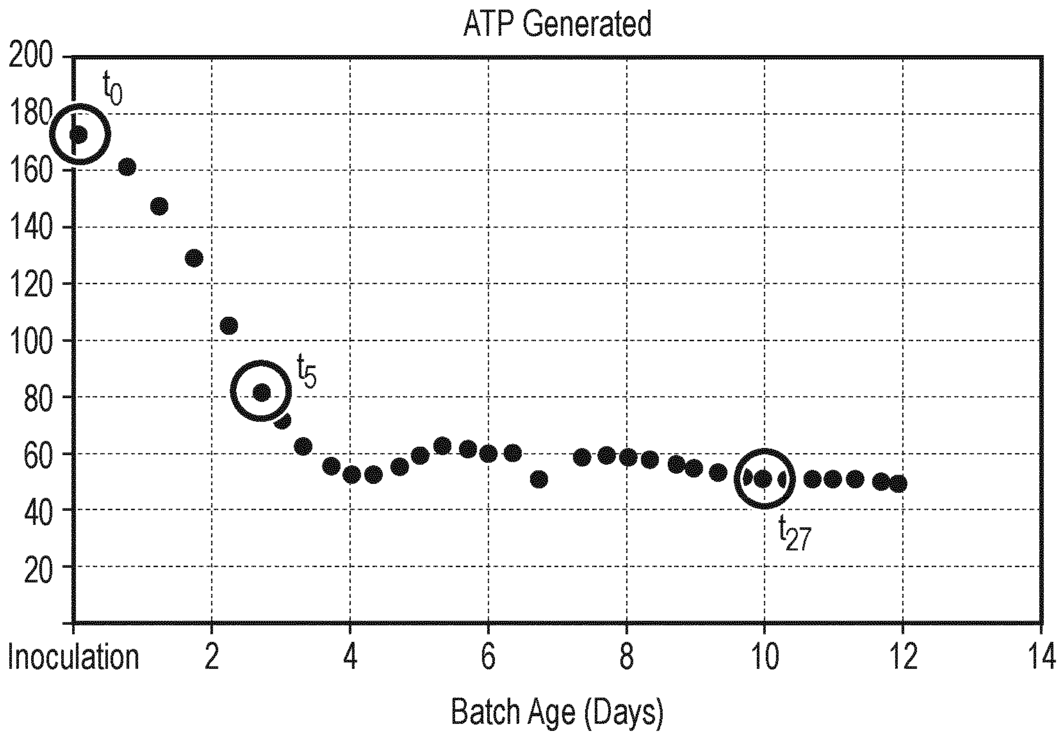

Training (calibration): The process applied in the multivariate analysis module will be explained below by reference to the fed batch process (Example 2). An analogous process can be applied for other configurations, such as the unfed batch process of Example 1, and the perfusion process of Example 3. Three of the four batches operated according to the standard operating procedure described in the fed-batch section above, with the temperature and pH at normal levels, were used for training (batches indicated as "NT" in FIG. 8). Each of these batches were considered to represent batches that result in a product with CQAs within specification. Further, these three batches together were considered to represent sufficient observations to build a representative set of data capturing common cause variation in metabolism. This was assessed by verifying the standard deviation in the control plot converged (see below). In general, heuristics and/or data-based criteria to verify this can be used, and the criteria used can vary between processes. The internal reaction rates, v, were then obtained as described above; the resulting evolution is shown for one of these four batches in FIG. 16. The batch maturities (from the parsing and preprocessing module), which are the x-axis value for each point in FIG. 16A, were stacked on top of one another to create the Y matrix using observation-wise unfolding. There were 34 measurements taken during each of the four batches, such that a matrix of size 136×1 (34*4=136) was obtained. Three flux distributions for the 94 reactions in the metabolic model used (not including the biomass pseudo reaction which was added to this model) are shown on FIGS. 16B-D. Further, through the systems biology module, these flux distributions are available for every point in time for all four batches. Observation-wise unfolding was applied to the flux distributions to stack them on top of one another to obtain the X matrix in the same way as was done for the maturities. This resulted in an X matrix of size 136×95. The calculated amount of total ATP generated was appended to the X matrix as an additional column, resulting in a matrix X with final size of 136×96. A similar process can be used to add process conditions to matrix X, i.e. as an additional column.

Partial Least Squares (PLS) regression was used to characterise the way that the reaction rates and ATP generated, collectively referred to as X, are varying with maturity (i.e. the batch age in this example), referred to as Y. Together, X and Y are referred to as the feature space. However, the variables in X are not independent of one another. For example, the four reactions in the middle of the glycolysis pathway where there is no branching must vary collinearly—increasing the reaction rate of one reaction necessarily increases the reaction rate of the remaining three due to the steady-state assumption in Equation (4a). Therefore, a set of linearly independent variables, called principal components are found, where the regression can be performed on these variables instead of the original variables. The loading weights, $p_i$ and $q_i$, define the relationship between the original feature space and the new score space for the X and Y data, respectively. It is referred to as the score space, because the value of each observation on the principal components is referred to as the scores. The X block scores are denoted by $t_i$, and the Y block scores are denoted by $u_i$. The loading weights, $p_i$ and $q_i$, are selected to maximize the covariance between the scores $t_i$ and $u_i$ so that the predictive power between X and Y is optimized in the linearly independent score space. The relationship between feature space, scores and loadings are described by Equations (1) and (2), which can also be expressed as:

$$X = \sum_{i=1}^{n} t_i * p_i + E \tag{1a}$$

$$Y = \sum_{i=1}^{n} u_i * q_i + F \tag{1b}$$

where n is the number of principal components to be extracted. In the examples below, the value of n was determined by cross-validation where more components are extracted if it increases the cross-validated predictions of Y from X. The variability in X and Y not described by the n extracted principal components remain in the residual matrices E and F; if n is selected as described above (where all components that increase the cross-validated predictions of Y from X are extracted) these are the aspects of metabolism that are independent of the bioprocess evolution. These aspects may for example be constant throughout the bioprocess, or may capture noise carried through the calculations from the raw measurements.

Monitoring/Prediction: The score values, T, for each principal component extracted can be used to define the normal evolution of internal metabolic states by defining an envelope of ±n standard deviation (where n can take any chosen value such as e.g. 3) around the average score value for each point in time. Bioprocesses whose scores remain within these boundaries can be said to maintain the internal metabolic state similar enough to the historical bioprocesses that were known to produce valid product, and as such the new bioprocess can be assumed to produce a valid product (i.e. a product according to specification).

Since all the DoE batches in the fed-batch process were run simultaneously, the prediction step is already partly completed. There are five new batches to consider: the one of four batches operated at the normal pH and temperature levels that was left out of the training step, two batches that had the temperature reduced slightly after day 7 and two batches that had the temperature reduced significantly after day 7. The ATP generated during all these batches as well as the 95 flux values corresponding to the metabolic model used were also generated for all these batches.

The loadings, $\rho_i$, that were generated by the PLS model in the training step, Equation (1a) were used to calculate the scores, $t_i$, for each observation from the new batches. These values were and overlaid on the control chart generated by the training step. Any deviations from the control limits can be notified to an engineer/plant operator. As such, from a single control chart, the operator is able to identify that the process is out of specification even if they have no understanding of the biological systems that are captured in those charts.

Further, the information from the model can be used to investigate the underlying causes of the deviations in the control charts. Indeed, the loadings capture the effect of multiple original variables, each of which may be small, and hence enable to detect small deviations in many variables instead of needing to find a large deviation in just one variable. In particular, the loading weights can be used to determine the multivariate contribution of each variable (which in this example are the fluxes in the metabolic model, and the total ATP generated) to the difference in projections between the average observations of two batches (such as e.g. the normal batches—within specification- and the batches at very low temperature—outside of specification).

Example 1—Unfed Batch Culture

Figure 9:
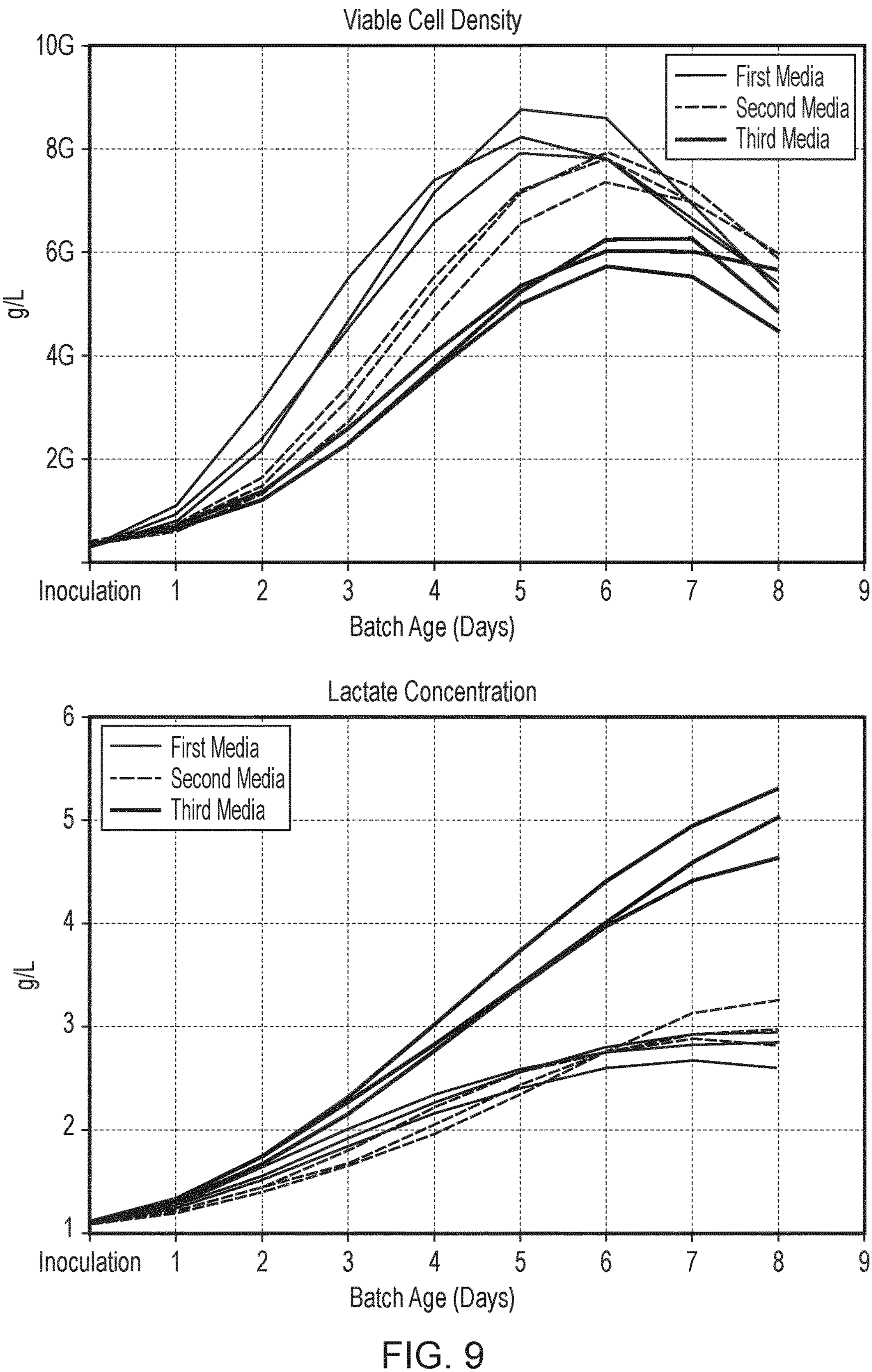
FIG. 9 shows smoothed data corresponding to the data in FIG. 7 (unfed batch)
Figure 9:
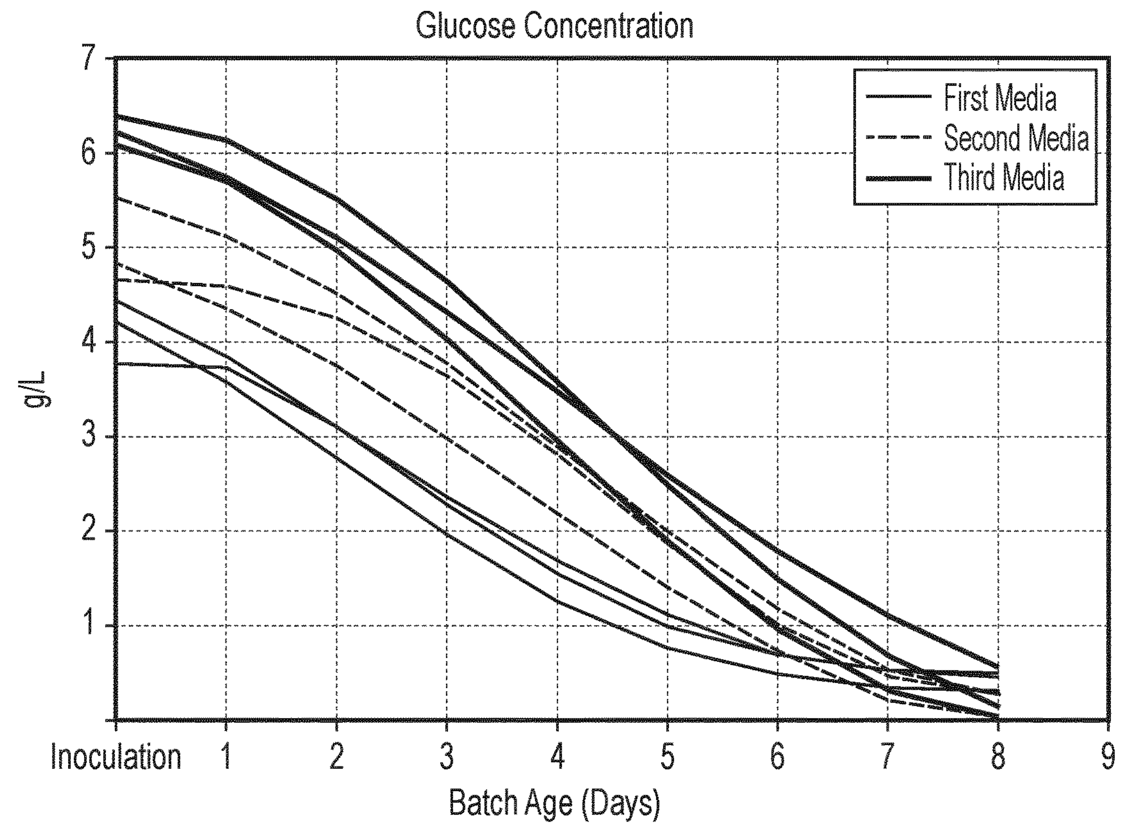
Figure 9:
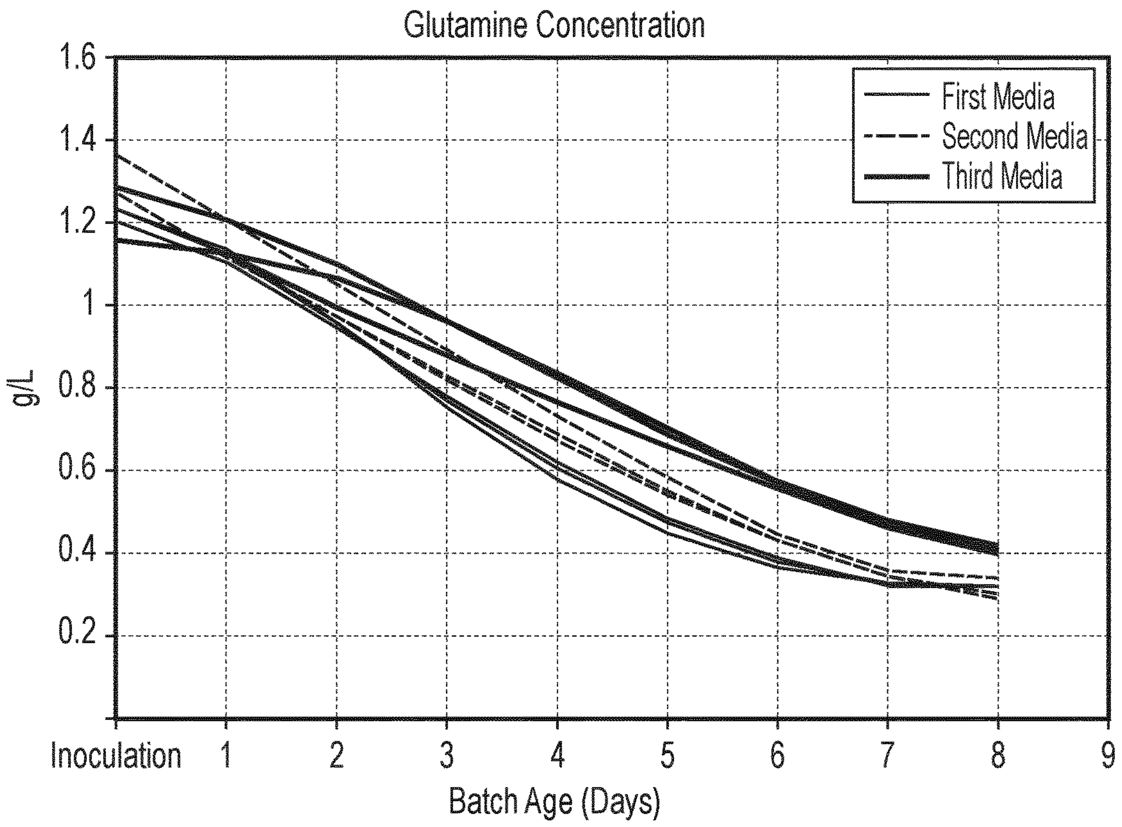

Parsing and Preprocessing Module: Simulated viable cell density, glucose concentration, lactate concentration and glutamine concentration data were obtained as explained above. This data is shown on FIG. 7. The data was generated for a common set of batch ages, and as such they can be merged immediately. Each simulated batch was given a unique ID (which in practice could be used e.g. to indicate which vessel it came from (1-1, 1-2, etc.). While not necessary, the media type for each batch was also appended to the data to allow for plotting the data in a meaningful way. The vessel/batch ID and media type are examples of metadata that can be appended to the data by the parsing and preprocessing module. The simulated raw viable cell densities shown on FIG. 7A and simulated raw metabolite data shown on FIGS. 7B-D were each smoothed independently, producing the smoothed data shown on FIG. 9.

Material Balance Module: In an unfed batch culture, there is no cell retention device, and therefore no auxiliary streams. In addition, there is no flow of material in/or out of the reactor (provided that the amount of material that is removed from the reactor for sampling can be ignored). Therefore, $F_F=F_H=F_B=0$ and Equation (8) is reduced to Equation (8c). We assume that the amount of material removed from the bioreactors is negligible compared to the overall reactor volume. Therefore, the reactor volume is roughly constant and Equation (8c) can be solved for qMet as shown in Equation (9c) (first step). Equation (8c) can be solved for qMet as shown in Equation (9c), second step, by making a first order finite difference approximation. Alternatively, where the metabolite data has been smoothed using a method that fits a function to the metabolite data (i.e. a function that expresses the metabolite concentration as a function of time/maturity), this function can be used to obtain the term $$\frac{d([Met])}{dt}$$

at maturity m, by obtaining the derivative of the function at maturity m (e.g. analytically). For example, where the function expressing the concentration of a metabolite ($y_j$) is a polynomial (e.g. using a method such as the Savitsky-Golay method) of the form $$y_j \cong \sum_{i=0}^{i=n} c_i x_j^i$$

where n is the degree of the polynomial, and x is maturity (e.g. time), then a derivative of this can be determined analytically as $$\frac{d([Met])}{dt}_j = \sum_{i=0}^{n} c_i * i * x_j^{i-1}.$$

Figure 12:
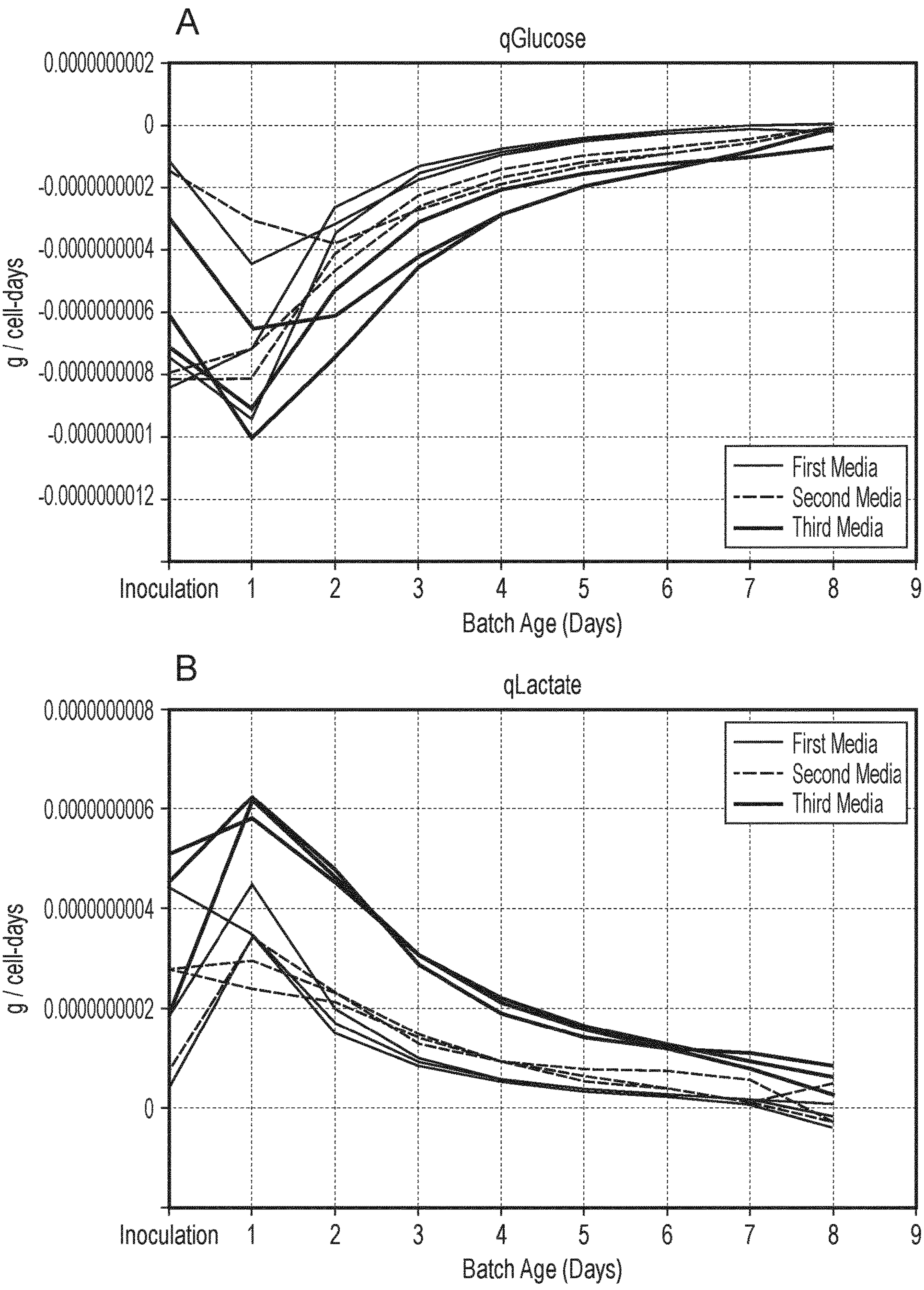
FIG. 12 shows calculated specific transport rates for the unfed batch data shown on FIGS. 7 and 9; (A) calculated specific transport rates for Glucose, (B) calculated specific transport rates for Lactate, (C) calculated specific transport rates for Glutamine.
Figure 12:
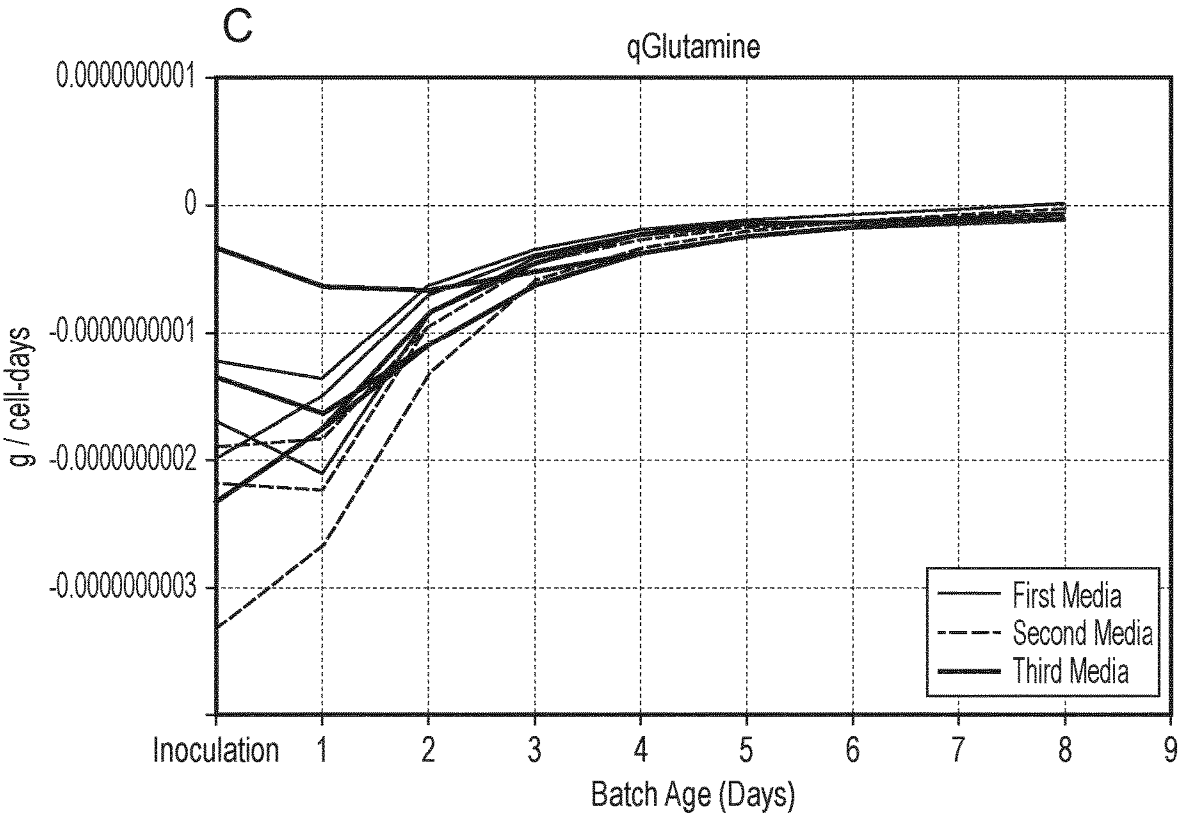

Regardless of the particular manner in which equation (9c) (first step) is solved, resulting metabolite transport rates are obtained. The results for glucose, lactate and glutamine in the present experiments are shown on FIG. 12.

Figure 17:
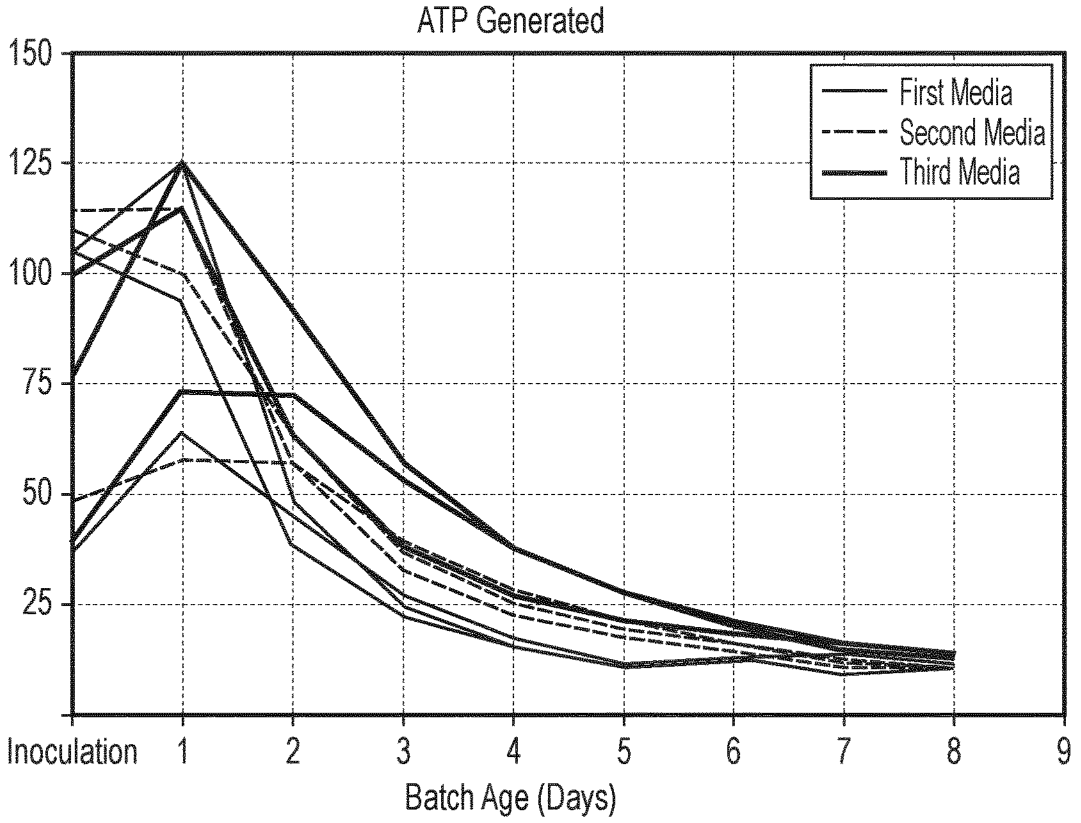
FIG. 17 shows the total rate of generation of ATP derived from the rates obtained in the flux balance analyses at respective maturities, in the unfed batch process of FIGS. 7, 9 and 12.

Systems Biology Module: The methodology described above was applied to the transport rates for the unfed batch shown in FIG. 9. The resulting total amount of ATP generated for all batches are shown on FIG. 17. While only the univariate calculated ATP generated is displayed here, there is an associated multivariate flux distribution (95 reaction rates) for every point where the ATP generated has been calculated.

Figure 20:
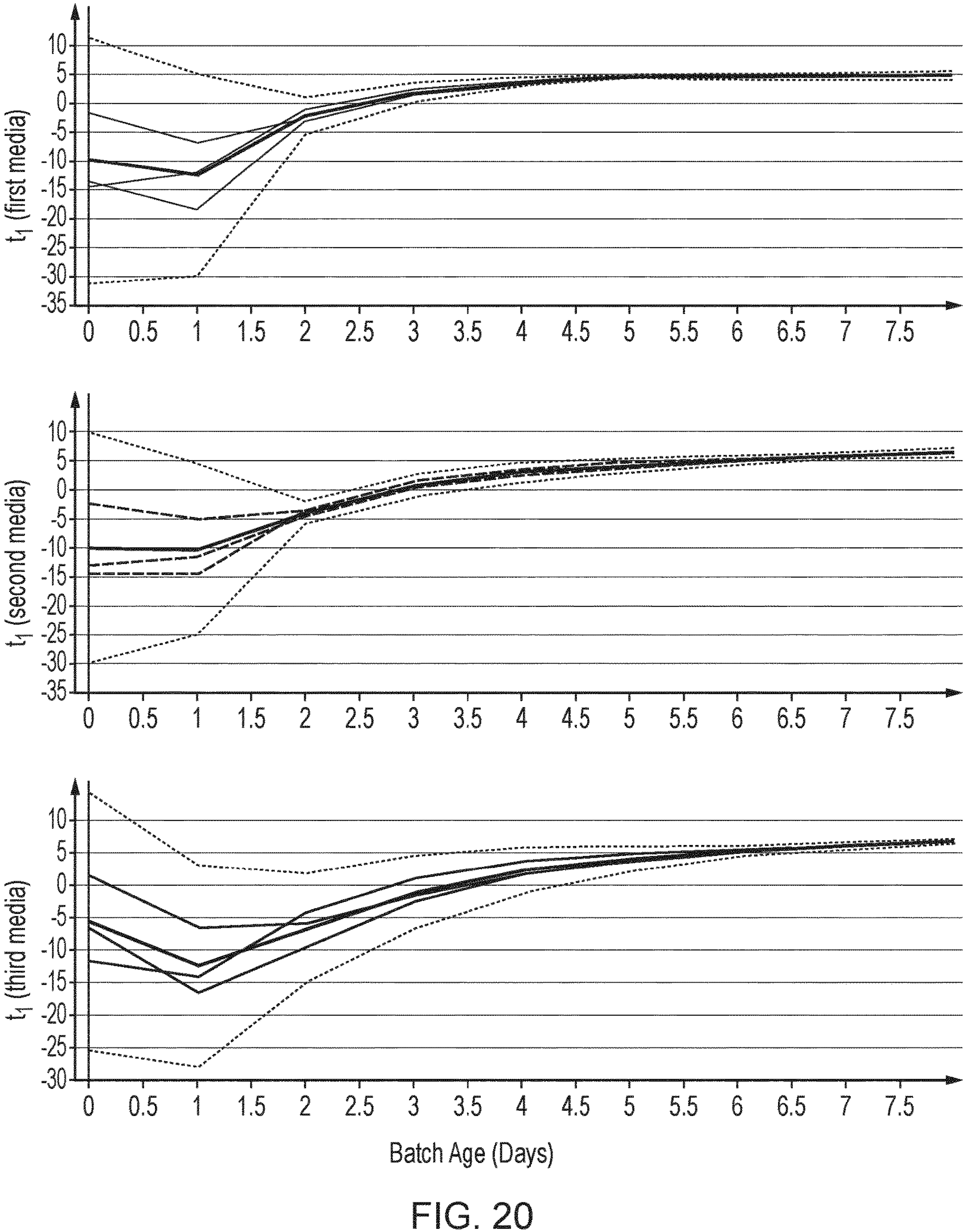
FIG. 20 shows control charts showing the scores for the first principal component for BEMs trained using the data from each of the sets of unfed batch experiments using a respective culture medium (FIGS. 7, 9 and 12); in all charts, the central solid line is the average of the other solid lines, and the dashed lines represent the ±3 standard deviations envelope around the average line.

Multivariate Analysis Module: the total ATP generated for the unfed batch processes (shown on FIG. 17) and the 95 flux values from the metabolic model (from which the values in FIG. 17 were derived) were obtained for each point in time through the systems biology module. These were used to construct the X and Y block of the PLS model as explained above in the same way as for the fed-batch process. The resulting multivariate control charts are shown in FIG. 20. In this experiment, there were no batches with deliberate deviations to detect changes in metabolic state, and as such no prediction step was implemented. Such a step would be accomplished in an analogous way as explained above for the fed-batch process.

Example 2—Fed Batch Culture

Figure 10:
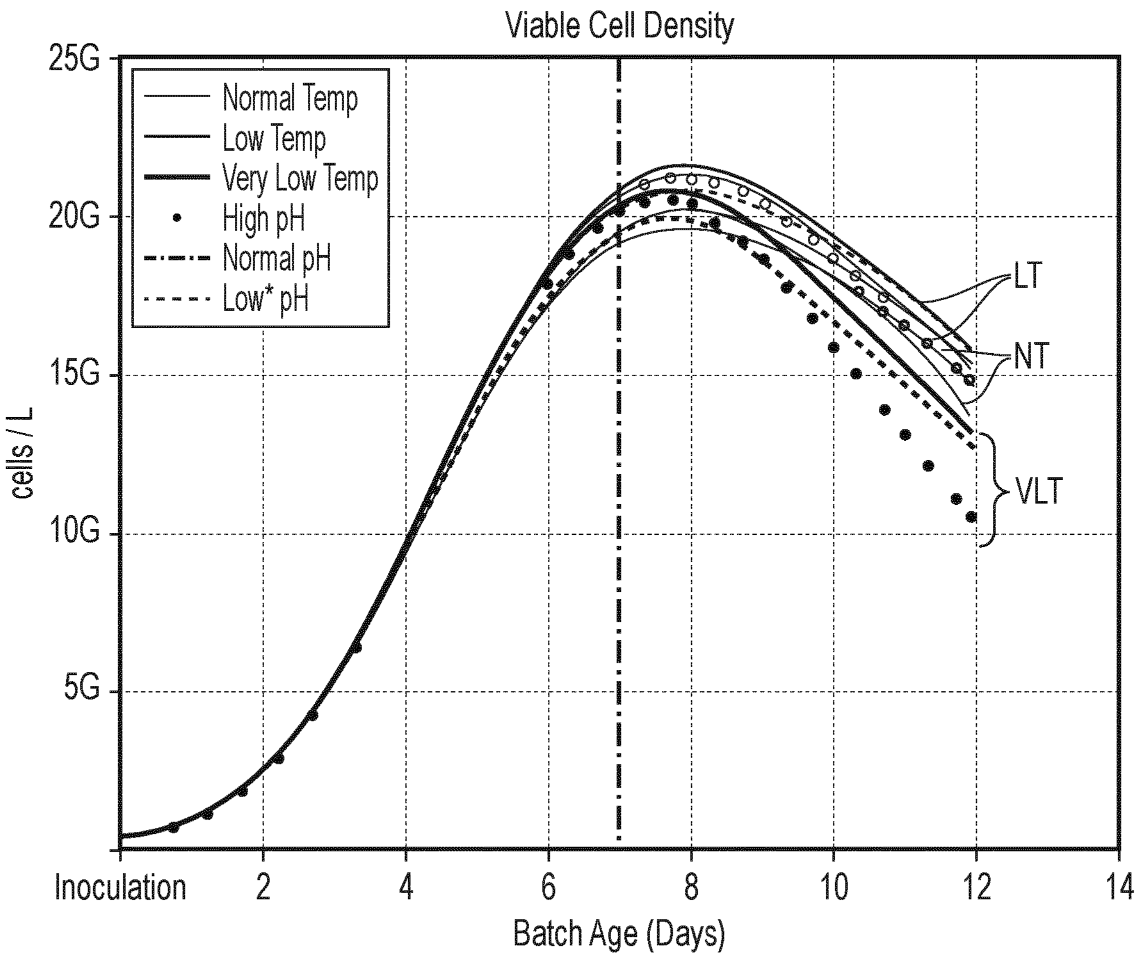
FIG. 10 shows smoothed viable cell density data corresponding to the data on FIG. 8A (fed batch)

Parsing and Preprocessing Module: The raw viable cell density, glucose concentration, lactate concentration, glutamine concentration, glutamate concentration and ammonia concentrations were saved in an excel file. Despite some of the metabolites being measured on the Flex2 and some being measured on an NMR, they were generated from the same sample so they could be merged into a single file immediately with the common batch age shown in FIG. 8. Each batch was given a unique ID to indicate which batch it came from (BR01, BR02, etc.). While not necessary, the DoE condition for each batch was also appended to the data to allow for plotting the data in a meaningful way. The batch ID and DOE conditions are examples of metadata that can be appended to the data by the parsing and preprocessing module. The raw viable cell densities shown on FIG. 8A were smoothed as described above. The smoothed data for the viable cell density is shown on FIG. 10.

Figure 11:
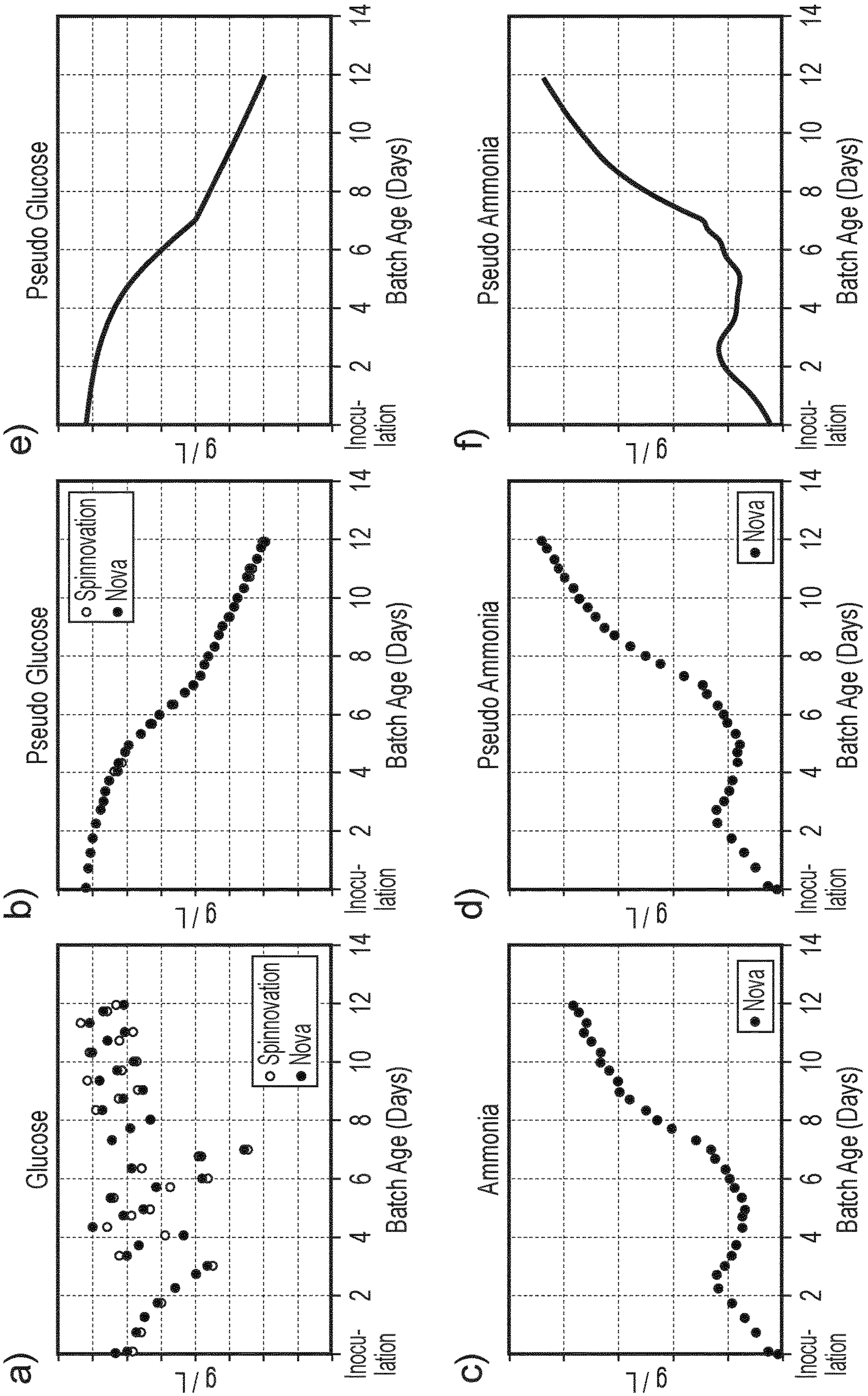
FIG. 11 shows raw metabolite data (A, C), pseudo metabolite data (B, D) and smoothed pseudo metabolite data (E, F) for two metabolites measured in the fed batch processes of FIG. 8.

The metabolites data was smoothed using an approach that takes into account the spike changes in concentration caused by feeds which are provided according to a bolus feed scheme (ex: the daily spikes after day 3 in the glucose concentration shown on FIG. 8B), where a large instantaneous addition of medium is used. In particular, the terms of the differential equation expressing the material balance (see Material Balance Module below) were expressed using a pseudo metabolite concentration, [pMet], that allows the feed stream term to be eliminated. For nutrients (which in this case refers to metabolites that are added to the feed stream to serve as a nutrient for the cells), such as glucose shown in FIG. 11(*a*), this is accomplished by taking the measured reactor volumes and known feed concentrations to determine how much of the nutrient is added to the reactor by each feed. This value is then subtracted from all measurements of the nutrient's concentration that come after that feed. This gives us the pseudo metabolite concentration, denoted [pMet], which is shown for Glucose in FIG. 11(*b*). For metabolites that are not present in the media (i.e. not added to the reactor in the feed), such as Ammonia shown in FIG. 11(*c*), the measured reactor volumes are used to determine the change in concentration due to dilution that is caused by each feed. This value is then added to all measurements of the metabolite's concentration that come after that feed. This gives us the pseudo metabolite concentration, which is shown for Ammonia in FIG. 11(*d*). A smoothing algorithm as known in the art (e.g. as used for the VCD) can then be applied to those pseudo-metabolite measurements instead of the raw metabolite concentration measurements. Further, in this case the smoothing was applied in two steps, one for the data before the DOE conditions were implemented, and one for the data following the implementation of the DoE conditions. In embodiments using a drip feed strategy (i.e. where no step changes in concentrations are expected), smoothing may be performed for the metabolites in a similar way as for the unfed batch and perfusion cultures.

Material Balance Module: In a fed batch culture, there is no cell retention device, and therefore no auxiliary streams as well. In addition, there is no flow of material out of the reactor (assuming that the amount of material removed from the reactor by sampling is negligible). Therefore, $F_H = F_B = 0$ and Equation (8) is reduced to Equation (8b). Due to the bolus feed strategy implemented in this example we can redefine the differential equation in terms of a pseudo metabolite concentration, [pMet], that allows the feed stream term to be eliminated (as explained above). This results in Equation (8d). We assumed that the amount of volume removed from the reactor, and the amount of volume fed into the reactor, is negligible compared the reactor volume. As such, we could also assume that volume in the reactor is roughly constant and Equation (8d) is reduced to Equation (9d) (first step). Equation (8d) can be solved for qMet as shown in Equation (9d), second step, by making a first order finite difference approximation. Alternatively, where the pseudo metabolite concentration data has been smoothed using a method that fits a function to the pseudo metabolite concentration data (i.e. a function that expresses the pseudo metabolite concentration as a function of time/maturity), this function can be used to obtain the term $$\frac{d([pMet])}{dt}$$

at maturity m, by obtaining the derivative of the function at maturity m (e.g. analytically). For example, where the function expressing the pseudo concentration of a metabolite ($y_j$) is a polynomial (e.g. using a method such as the Savitsky-Golay method) of the form $$y_j \cong \sum_{i=0}^{i=n} c_i x_j^i$$

where n is the degree of the polynomial, and x is maturity (e.g. time), then a derivative of this can be determined analytically as $$\frac{d([pMet])}{dt}_j = \Sigma_{i=0}^{n} c_i * i * x_j^{i-1}.$$

Regardless of the particular manner in which equation (9d) (first step) is solved, resulting metabolite transport rates are obtained. The results for glucose, lactate, ammonia, glutamate and glutamine in the present experiments are shown on FIG. 13.

Figure 16F:
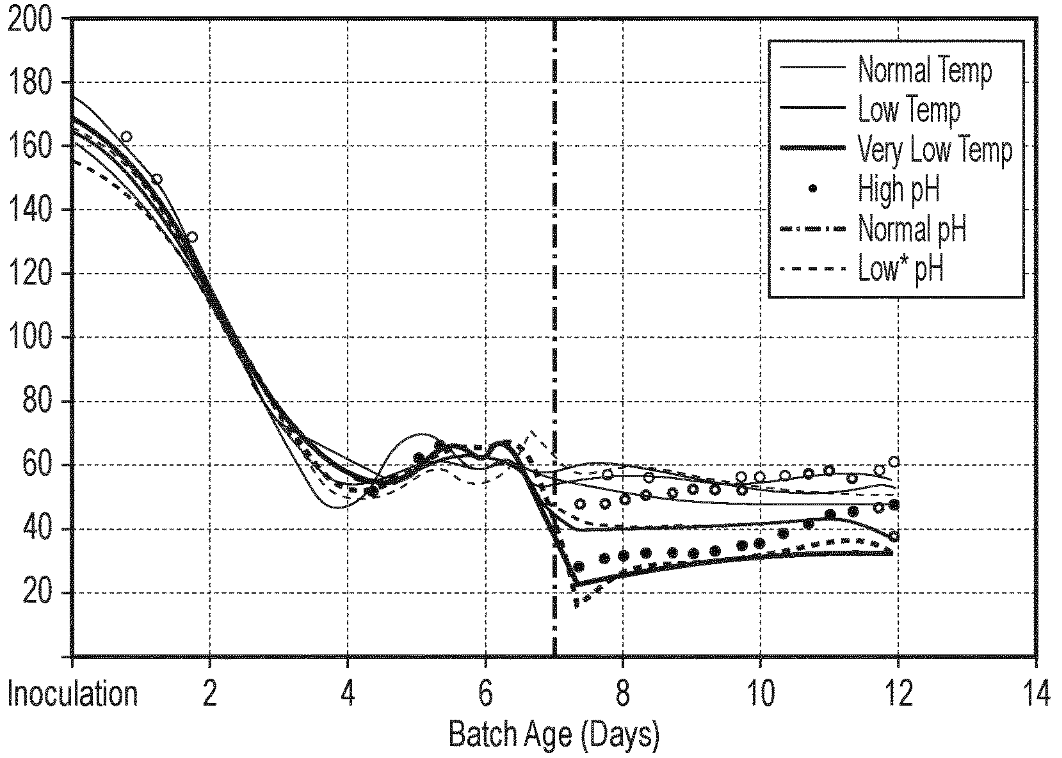

Systems Biology Module: the systems biology module was used to calculate metabolic fluxes as explained above. FIG. 16A shows the evolution of metabolite transport rates for one of the normal batches in FIG. 13. The evolution of the internal flux distribution is shown as an example for three time points: to in the lag phase in FIG. 16B, $t_5$ in the exponential growth phase in FIG. 16C and $t_{27}$ in the stationary phase in FIG. 16D. The evolution of the total amount of energy generated by the cells, represented by the total amount of ATP generated, throughout the batch is calculated from the evolution of flux distributions and is shown in FIG. 16E. FIG. 16F shows the total amount of ATP generated, calculated for all batches.

Multivariate Analysis Module: For the training step, a PLS model was fitted to the data as explained above, using the three fed batch processes operated at normal pH and temperature levels. This resulted in three principal components being extracted. These three new independent variables described 95.8% of the variability contained in the original 96 collinear variables in X and 91.4% of the variability in Y and 90% of the cross-validated variability in Y when predicting it from X. In other words, the principal components did a very good job of describing the flux data and the predictive power is high. Therefore, the score values on these three principal components could be used to define the normal evolution of the 95 reaction rates and total ATP generated during the normal operation of our fed-batch process. The evolution for each of the three batches are shown in red for the first two principal components in FIG. 18. Their average value is shown with a solid black line and the three standard deviation window around the average is shown with dashed black lines. These black dashed lines can then be used as control limits for future batches—those batches whose scores remain within these boundaries can be said to maintain the internal metabolic condition similar enough to the historical batches that were known to produce valid product for the new batch to be assumed to produce valid product as well. This can be used for monitoring purposed.

In the prediction step, five new batches were considered: the one of four batches operated at the normal pH and temperature levels that was left out of the training step, two batches that had the temperature reduced slightly after day 7 and two batches that had the temperature reduced significantly after day 7. The ATP generated during all these batches are shown in FIG. 16F. While not shown, the 95 flux values were also generated for all these batches as well.

The loadings, $\rho_i$, that were generated by the PLS model in the training step, Equation (1a) were used to calculate the scores, $t_i$, for each observation from the new batches. These values were and overlaid on the control chart generated by the training step, as shown on FIG. 19A. Here, up until day 7, all batches were operated normally—and all batches stay within the control limits that define the normal evolution of cellular metabolism. For the one batch operated normally, we can see on FIG. 19A that the metabolic state stays within the control limits as it should. However, for the two batches that were operated at a slightly lower temperature, we can see on FIG. 19A that after the process deviation was induced on day 7 the score values representing the internal metabolic condition move outside of the ±36 control limits and then stay outside of, or sit right on top of, this limit for the remainder of the batch. Furthermore, for the two batches that were operated at a significantly lower temperature (very low temperature), we can see on FIG. 19A that after the process deviation was induced on day 7 that the score values move far outside of the control limits and stay there. Therefore, the batches operated at low or very low temperature are predicted to result in out-of-specification product, due to a process deviation. Further, these are projecting outside of the control limit despite the model being based only on the metabolic condition and not on the process conditions.

Figure 19:
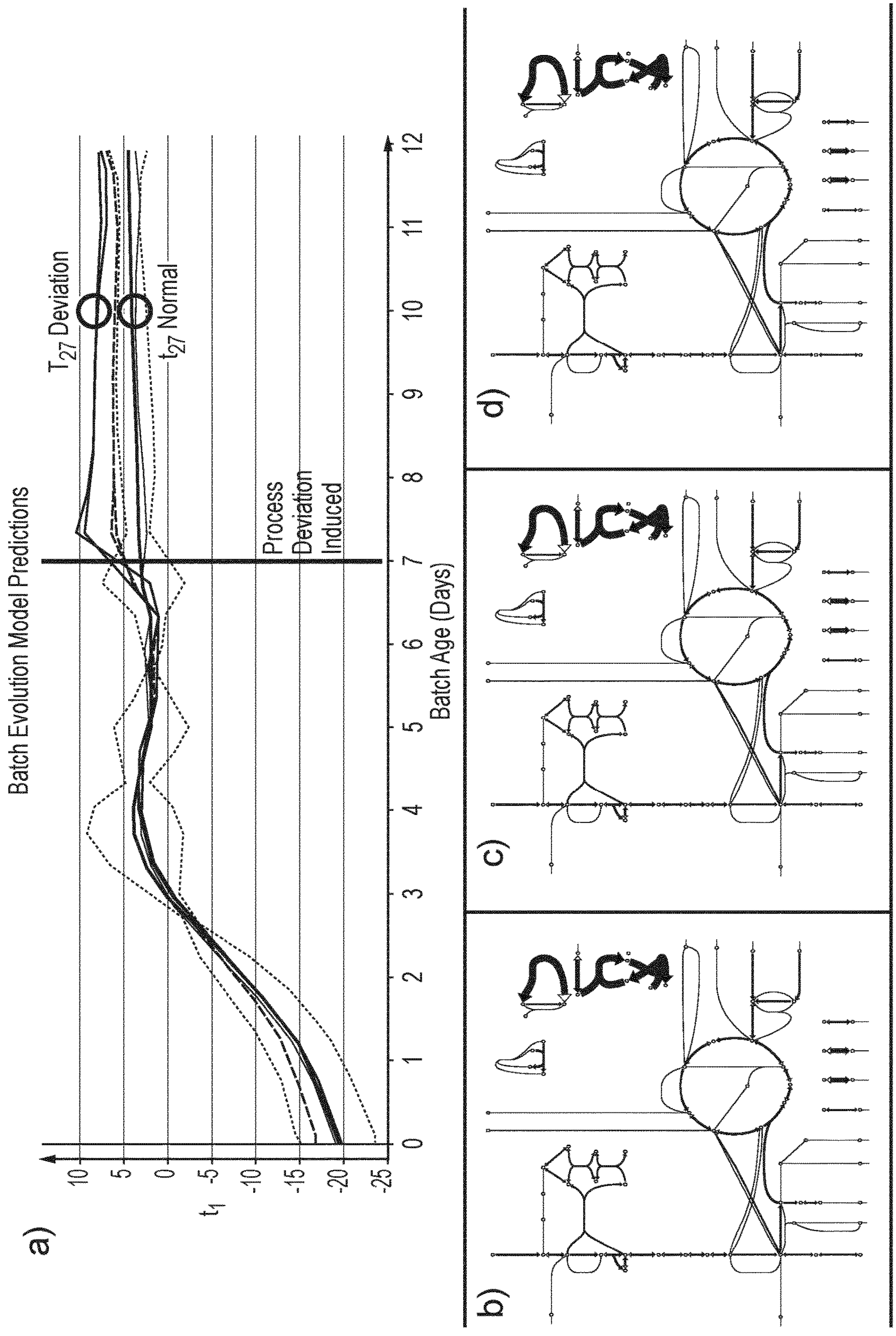
FIG. 19 shows a batch evolution model prediction step based on the scores illustrated on FIG. 18; (A and E) control chart showing the scores for the first principal component (A) and the second principal component (E) for a normal batch staying within specification, two low temperature batches, and two very low temperature batches, going outside of specification, where the specification is indicated by the dashed lines showing the envelope determined as indicated on FIG. 18; (B) Metabolic flux distribution for t27 of the normal batch; (C) Metabolic flux distribution for t27 of one of the very low temperature batches; and (D) the difference in multivariate group contributions between the average very low temperature batch and average normal batch.
Figure 19:
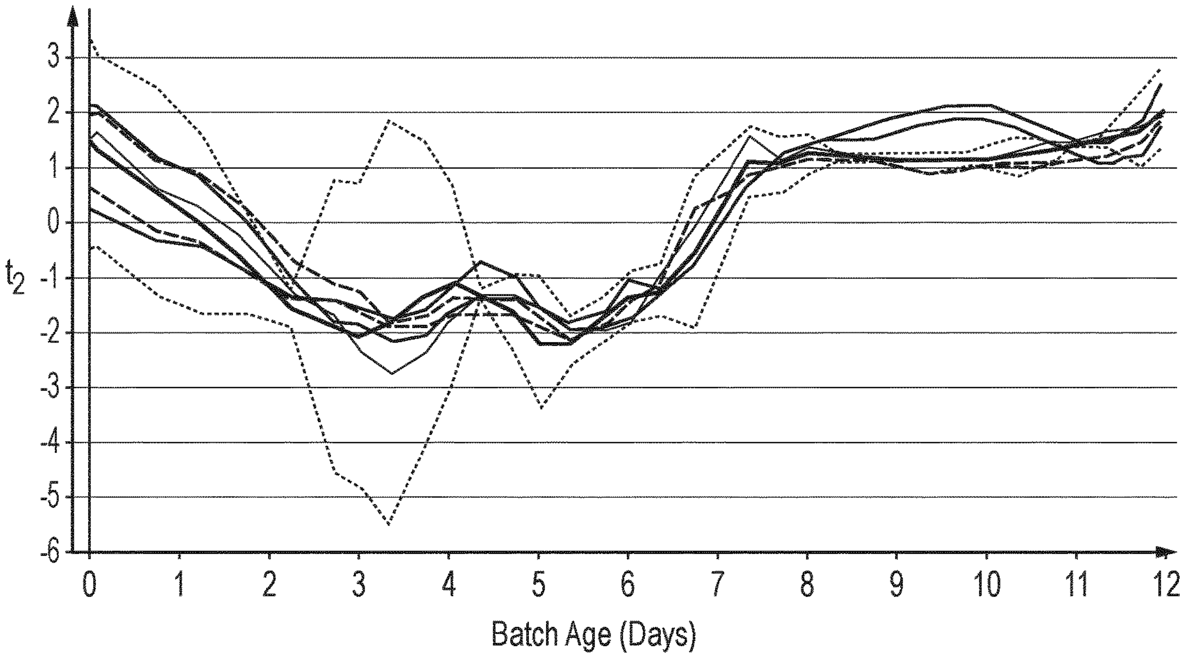

The advantage of this approach can be seen from the flux distributions in FIG. 19B and FIG. 19C, which show the flux distribution at $t_{27}$=10 days for the in-specification batch (FIG. 19B) and one of the two far out of specification batches (FIG. 19C), respectively. The metabolic flux charts on FIGS. 19B and C show small differences in the oxidative phosphorylation pathway thickness. However, by using the loading weights to determine the multivariate contribution of each variable to the difference in projections between the average observations of these two batches after day 7 we can see that there are in fact small, but systemic, differences between the two states, as shown in FIG. 19D. This illustrates one of the advantage of using multivariate methods: it is possible to detect small deviations in many variables instead of needing to find a large deviation in just one variable. On FIG. 19D, the red highlighted lines indicate fluxes where the flux values for the low temperature shifted batch were less than the flux values for the normal batch; the green highlighted lines indicate fluxes where the flux values for the low temperature shifted batch were greater than the flux values for the normal batch; and the line thickness indicates the normalized magnitude of this difference.

Example 3—Perfusion Culture

Parsing and Preprocessing Module: The raw viable cell density, glucose concentration, lactate concentration, glutamine concentration, glutamate concentration and ammonia concentrations are saved in an excel file. As all of the measurements were generated on the Flex analyzer from the same sample so they can be merged into a single file immediately using the common batch age. Each batch was given a unique ID to indicate which batch it came from (7-18, 7-22, etc.). Due to the way that a perfusion process is operated, discontinuities in concentration data may result from step changes in the control strategy used to manipulate the flow of material in and out of the reactor. In order to deal with this, in this example the smoothing process was applied to the calculated metabolite transport rates themselves (calculated by the Material Balance Module) instead of the raw data that is used to calculate the transport rates.

Material Balance Module: In a perfusion culture, all the streams in the diagram shown in FIG. 1*b* are present. The process was operated in such a way that reactor volume was held constant; therefore, $F_F=F_H+F_B$. We make several assumptions; first, concentration gradients within the reactor are negligible; therefore, $[Met]_B=[Met]_H=[Met]$. Second, the cell retention device operates perfectly; $VCD_H=0$. Third, the number of cells removed from the reactor is negligible; therefore, $VCD_B=0$. Even though this is a poor assumption from a theoretical perspective, the mathematical impact on the calculation is negligible because $F_B$ is an order of magnitude smaller than $F_H$. Fourth, the change in feed media density due to cell expansion and metabolite secretion is negligible; therefore, $\rho=\rho_F=\rho_B=\rho_H$. After applying all of these assumptions, the material balance in Equation (8) is reduced to Equation (8a), which can itself be reduced to $$V*\frac{d([Met])}{dt}=\frac{F_F}{\rho}*[Met]_F-\frac{(F_H+F_B)}{\rho}*[Met]+qMet*(VCD*V). \tag{8a'}$$

Finally, we can create a first-order finite difference representation of the differential equation in Equation (8a') and solve the resulting algebraic equation for qMet at the $m^{th}$ timepoint as shown in Equation (9a). The numerical integral of the viable cell density used in equation (9a) was evaluated by applying the trapezoidal approximation to the raw cell densities. The metabolite concentrations and IVCDs, as well as their respective time points, have been measured or calculated. In addition, the feed flow rates were measured, and the reactor volume, media density and feed media composition were known. Therefore, the metabolite transport rates can be found directly from Equation (9a) for each time point. Then the procedure is repeated for all metabolites. The resulting metabolite transport rates were smoothed as explained above.

Systems Biology Module: The methodology described above was applied to the transport rates for the perfusion processes as explained above.

Multivariate Analysis Module: the total ATP generated for the perfusion processes and the 95 flux values from the metabolic model were obtained for each point in time through the systems biology module. These were used to construct the X and Y block of the PLS model as explained above in the same way as for the fed-batch process. In this experiment, there were no batches with deliberate deviations to detect changes in metabolic state, and as such no prediction step was implemented. Such a step would be accomplished in an analogous way as explained above for the fed-batch process.

Example 4—Fed Batch Process Comparison of Models with/without Metabolic Condition Variables In this example, the data from the Fed Batch Process (Example 2 above) was used to compare a solution according to the invention (as in Example 2) with an approach in which the metabolic condition is not used to monitor bioprocess evolution. In all models described below, the Y block data is the exact same maturity values used in the model in Example 2.

Available Data: The following data was available (with the number of variables indicated between brackets):

- Measurements during process operation (21 variables):
- Nova measurements (13):
  - Metabolite concentrations (4): Glucose, lactate, glutamine, glutamate
  - Electrolyte concentrations (4): Ammonium, sodium, potassium, calcium
  - Cell counter (4): Total cell density, viable cell density, viability, cell diameter
  - Other (1): Osmolality
- Control system measurements (7):
  - Controlled variables (4): Oxygen concentration, pH, temperature, agitation rate
  - Levers (3): Air flowrate in, $CO_2$ flowrate in, $O_2$ flowrate in
- HPLC off-line analysis (1):
  - Product (1): Titer
- Metabolic condition variables:
- Transport Rate Data from Material Balance Module (5 variables)
  - Transport rates: qGlc, qLac, qGln, qGlu, qAmm
- Internal Flux Rate Data from Systems Biology Module (96 variables)
  - Flux values (95): For example, PGK and PYK in FIG. 15A
  - ATP generated (1)

Figure 21:
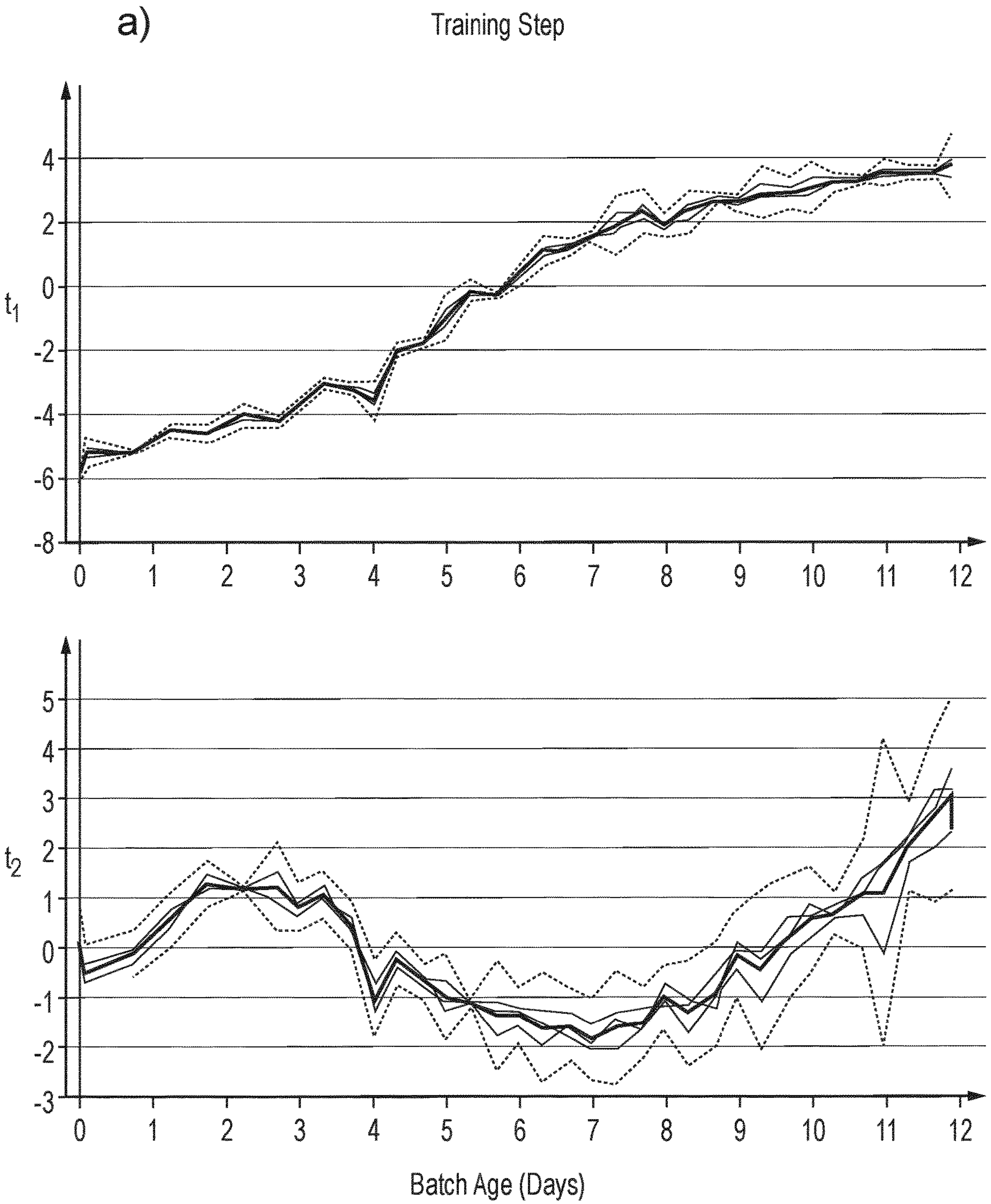
FIG. 21 shows Batch Evolution Model control charts generated from process data alone for the fed batch experiments of FIGS. 8 and 11; (A) illustrates the training step in which a BEM is fitted using only normal batch data—the dashed lines represent the ±3 standard deviations envelope around the average of the solid lines shown (each of which represent a separate run of the fed batch process run in normal conditions); and (B) illustrates the results of the prediction step in which the model that generated the scores in (A) is used to predict scores for runs with non-normal temperatures—the dashed lines are the same as on Figure A, the solid lines out of the envelope show the low and very low temperature runs.
Figure 21:
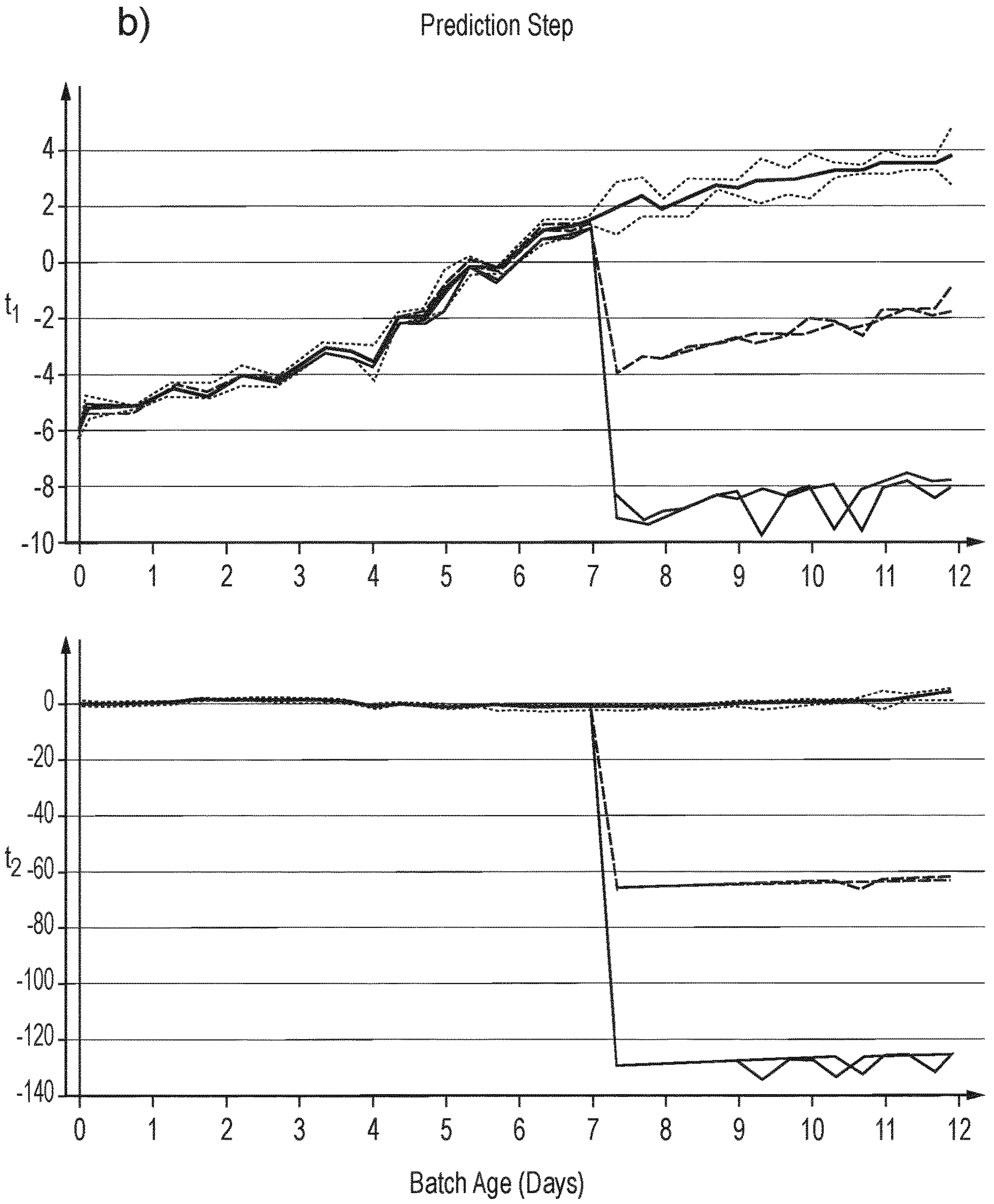

Process Data Model (no metabolic condition variables): The process data model used the 21 variables representing measurements during process operation as X block features (see multivariate analysis module explanation above). The first two principal components were found to characterise 56.3% of the variability in the process data and 98% of the variability in maturity with a $Q^2$ of 0.977. The Batch Evolution Model (BEM) control charts generated by the training step are shown in FIG. 21A and the results of the prediction step are shown in FIG. 21B for the first two principal components. FIG. 21 shows that there is very good detection of the process deviations in this case. However, this is primarily because the temperature and pH levels have been included in the model, where these parameters are the primary reason for process deviation as explained above. Accordingly, the primary source of detecting these differences in the BEM stems directly from the temperature and pH measurements.

Figure 22:
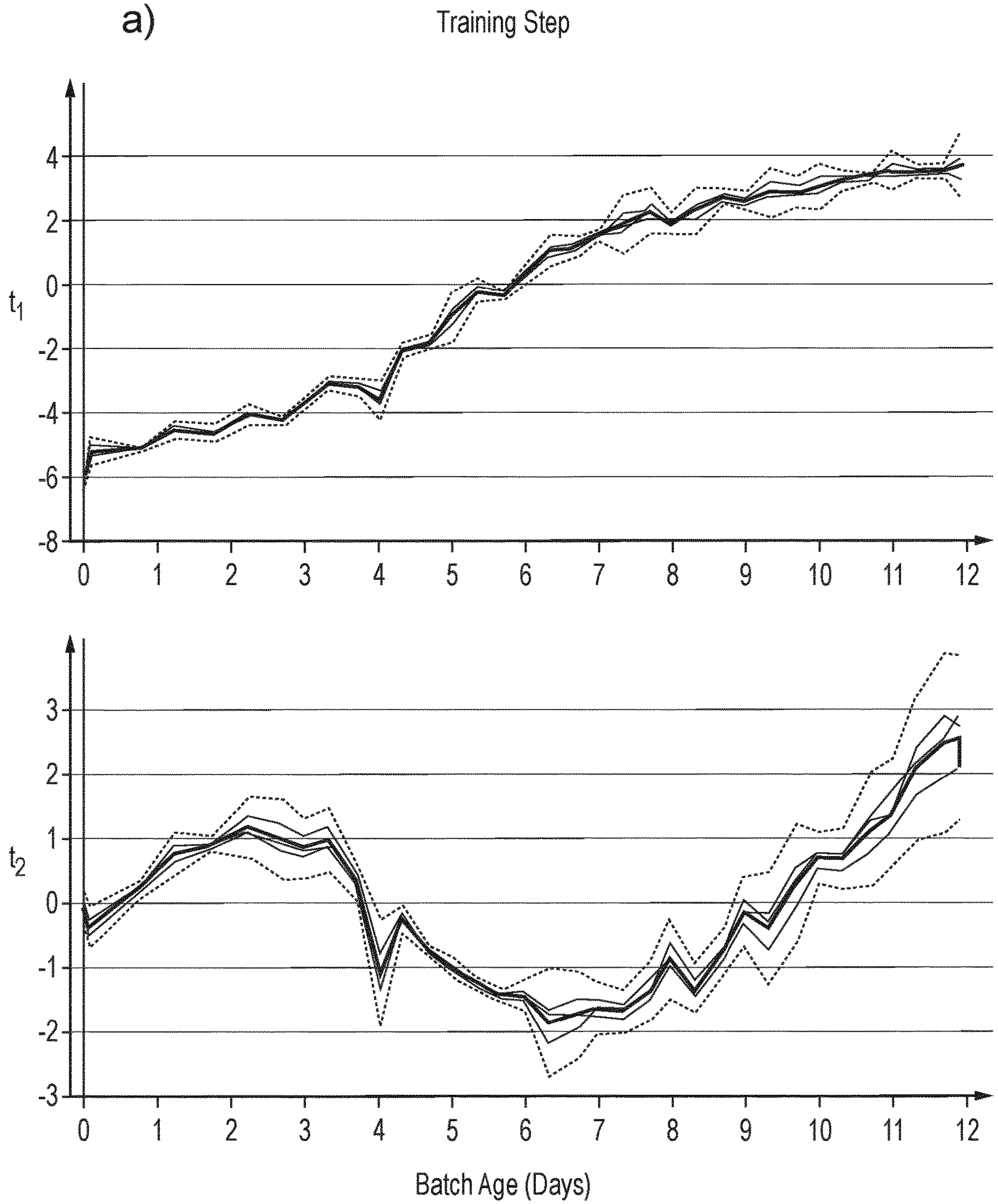
FIG. 22 shows Batch Evolution Model control charts generated from process data alone for the fed batch experiments of FIGS. 8 and 11, without including the pH and temperature as variables in the model; (A) illustrates the training step in which a BEM is fitted using only normal batch data—the dashed lines represent the ±3 standard deviations envelope around the average of the solid lines shown (each of which represent a separate run of the fed batch process run in normal conditions); and (B) illustrates the results of the prediction step in which the model that generated the scores in (A) is used to predict scores for runs with non-normal temperatures—the dashed lines are the same as on Figure A.
Figure 22:
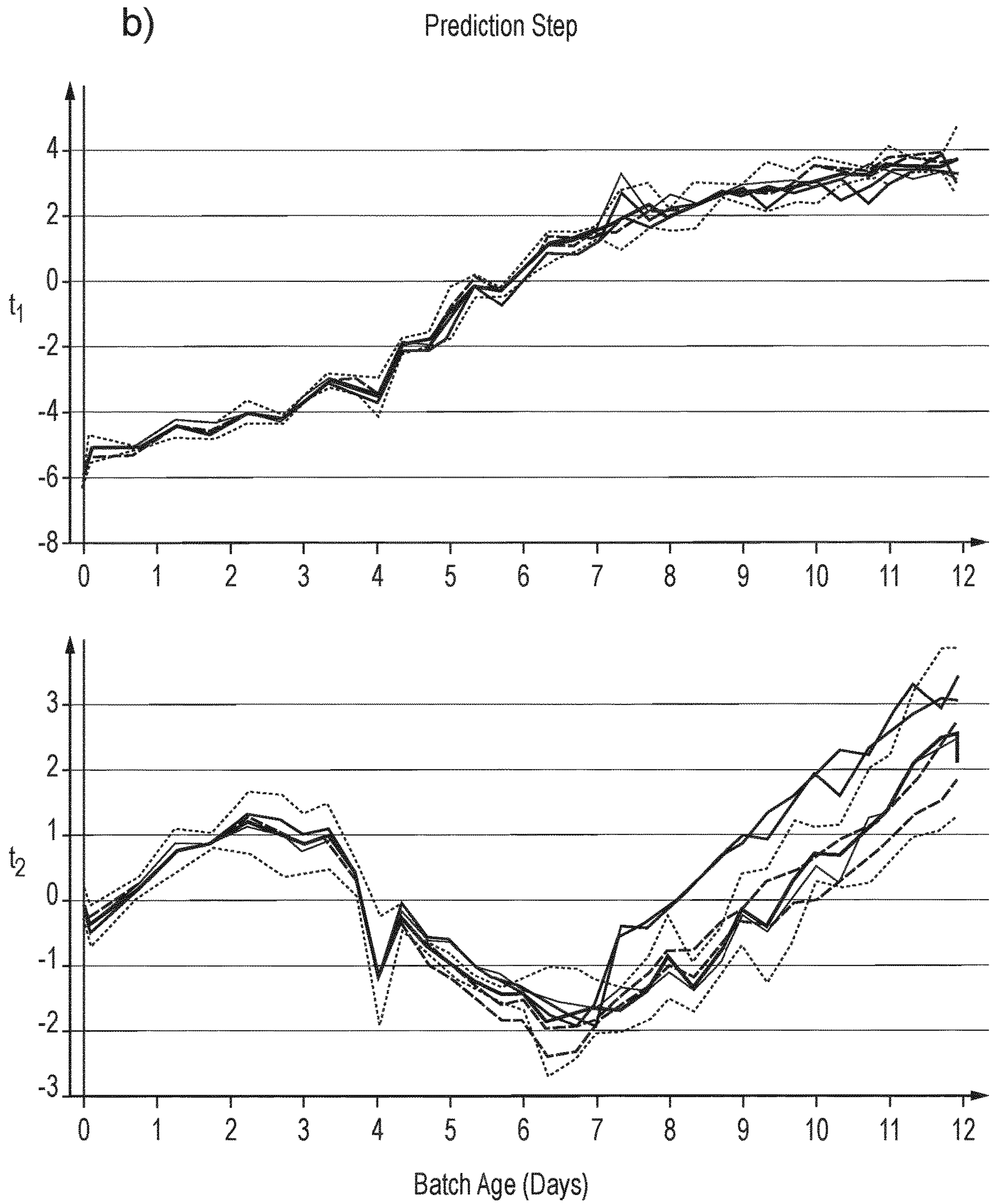

A second model was built using 19 of the process data variables as X block features. In this case, the Temperature and pH levels are excluded. The first two principal components were found to characterise 61.7% of the variability in the process data and 97.9% of the variability in maturity with a $Q^2$ of 0.978. The BEM control charts generated by the training step are shown in FIG. 22A and the results of the prediction step are shown in FIG. 22B for the first two principal components. Detecting the process deviations is clearly worse here. On both principal components, more so the second, there are sustained deviations outside of the control limits between days 4-6 despite no process deviation occurring before day 7. In addition, only the extreme temperature shift, marked in blue, shows a consistent departure outside the control limits and only for the second principal component. Furthermore, the low temperature shift is largely indistinguishable from the normal batch on both principal components. Finally, the normal, low temperature and extreme low temperature batches all go in and out of the control limits on the first principal component.

Figure 23:
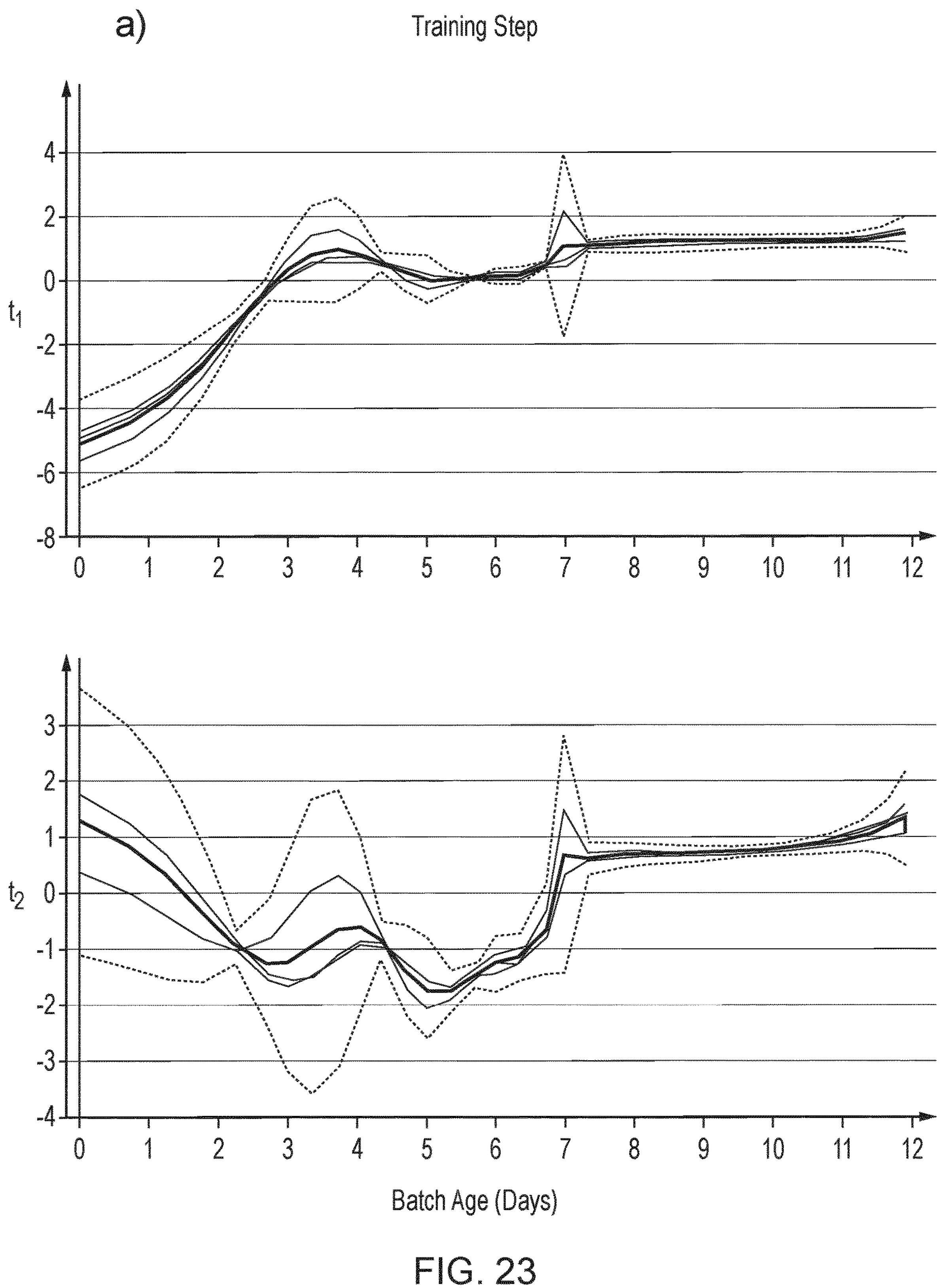
FIG. 23 shows Batch Evolution Model control charts generated from transport rate data alone for the fed batch experiments of FIGS. 8, 11 and 13; (A) illustrates the training step in which a BEM is fitted using only normal batch data—the dashed lines represent the ±3 standard deviations envelope around the average of the solid lines shown (each of which represent a separate run of the fed batch process run in normal conditions); and (B) illustrates the results of the prediction step in which the model that generated the scores in (A) is used to predict scores for runs with non-normal temperatures—the dashed lines are the same as on Figure A.
Figure 23:
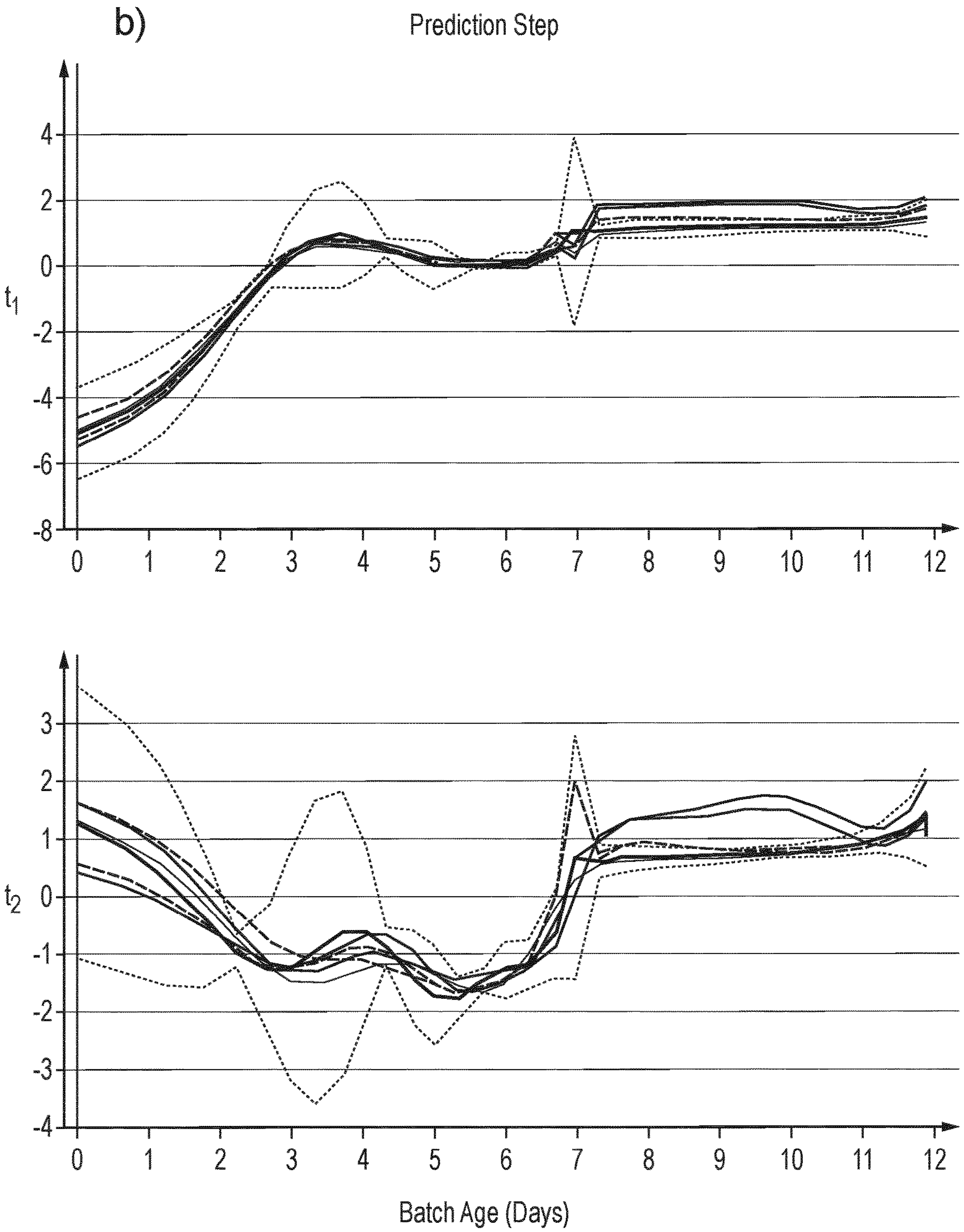

Transport Rate Data Model: In this model, only the transport rate data (output from the material balance analysis module) was used, i.e. the transport rate data model uses the 5 transport rates as X block features. In this case, the first two principal components were found to characterise 98.7% of the variability in the transport rate data and 79.4% of the variability in maturity with a $Q^2$ of 0.782. The BEM control charts generated by the training step are shown in FIG. 23A and the results of the prediction step are shown in FIG. 23B for the first two principal components. Here there is a significant improvement in the model robustness. At most only a single data point appears outside of the control limits before day 7 on either principal component (compared with several days in a row being outside of the control limits in FIG. 22B). In addition, the normal batch does not move outside of the control limits after day 7 like it did several times in FIG. 22B. There is also a significant improvement in the detection of process deviations. On both principal components, the extreme temperature shift appears outside of the control limits after day 7 (excluding the last 1.5 days on the second principal component). In addition, the low temperature batches appear slightly outside of the control limits for most of the stationary phase on the first principal component and briefly on the second principal component. However, even when it is not correctly detecting a deviation for the low temperature batch, the effect is still captured consistently in this model. The low temperature batch appears above the normal batch, even for the regions where it remains in the control limits (excluding the end of the batch on PC2); furthermore, the extreme low temperature batch appears above the low temperature batches (again excluding the end of the batch on PC2). Finally, the deviation is detected on the primary process driver (PC1) in the transport rate model instead of on the secondary process driver (PC2).

Figure 18:
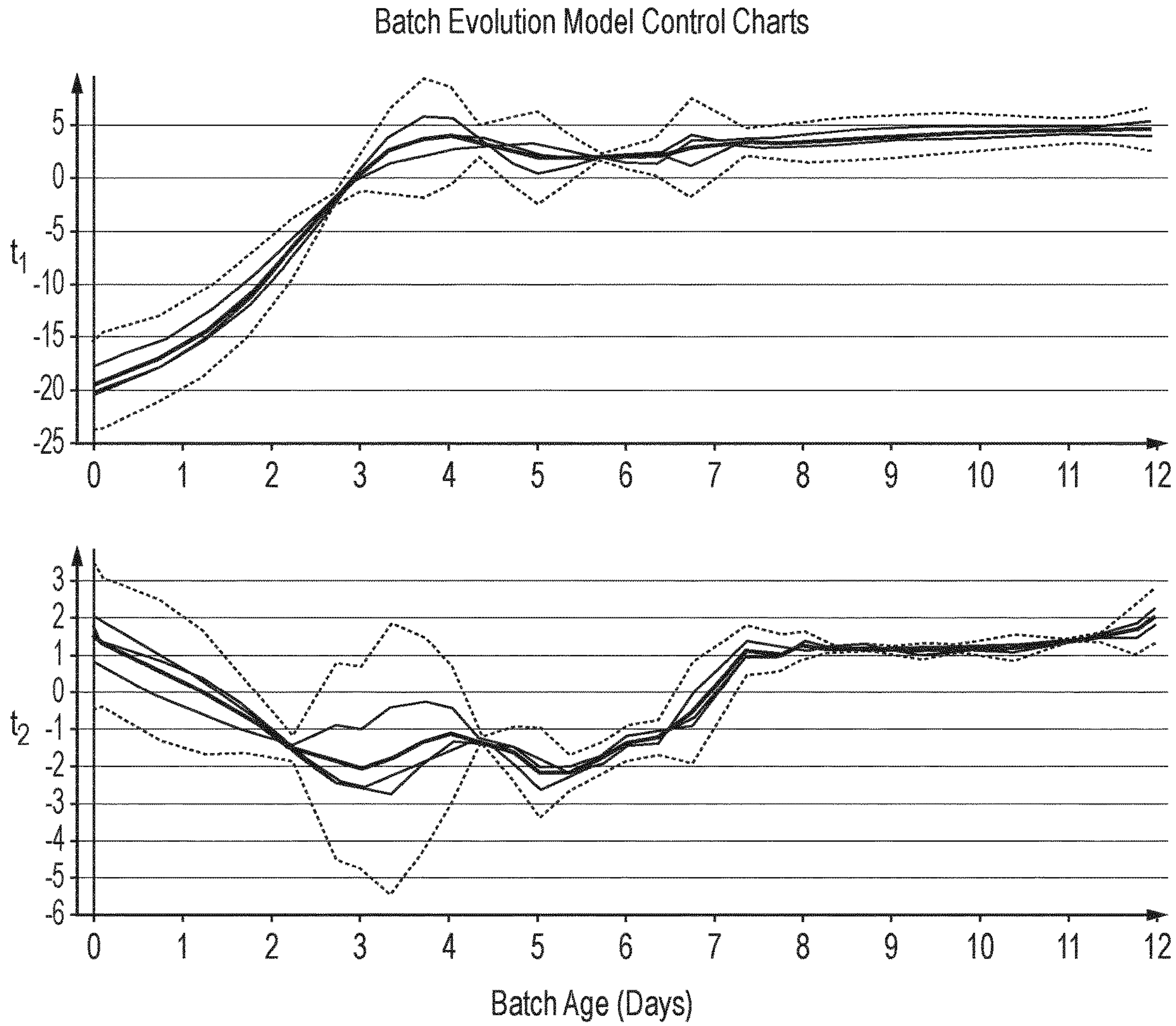
FIG. 18 shows batch evolution model (BEM) control charts for the fed-batch processes operated under normal conditions, derived from the data on FIG. 16; the top chart shows the scores for the first principal component as a function of maturity, and the bottom chart shows the scores for the second principal component as a function of maturity; in both charts, the central solid line is the average of the other solid lines, and the dashed lines represent the ±3 standard deviations envelope around the average line.

Flux Data Model: In this model, all 95 reaction rates in the metabolic model and the total ATP generated (output from the systems biology module module) were used, i.e. the flux data model uses the 96 internal flux rates as X block features. This is the same model as in Example 2. In this case, the first two principal components were found to characterize 94.4% of the variability in the transport rate data and 87.5% of the variability in maturity with a $Q^2$ of 0.872. The BEM control charts generated by the training step are shown in FIG. 18 and the results of the prediction step are shown in FIG. 19A and FIG. 19E for the first two principal components. The interpretation is very similar to the transport rate model, except the results are improved. In terms of robustness, a similar amount of single data points move outside of the control window during the first 7 days. In terms of detecting process deviations, the low temperature batch no longer goes back inside the control limits (or to a negligible degree) during the stationary phase on the first principal component. Furthermore, the separation between normal, low temperature and extreme low temperature batches is more pronounced. The detection of process deviations is most accurate here.

Discussion: The data in this example demonstrates that there is a clear advantage of using the material balance module's output as inputs for the multivariate analysis module (compared to using the process data alone). There is a smaller advantage seen when using the systems biology module's output as inputs for the multivariate analysis module (compared to using the output from the material balance module directly). Of note, the performance of the process data model depends on the variables that are included in the model. As such, it is likely that the improvement between the models shown here would be less pronounced for an industrial process that had determined all critical process parameters and used a robust DoE to manipulate the CPPs when training the batch evolution model from process data alone. Nevertheless, an improvement would still be expected when comparing the transport rate data or flux data models to the corresponding model trained on the same raw data but not including the representation of the metabolic condition. Conversely, as shown above, the use of the metabolic condition variables allows to obtain a model without requiring as much data as would be needed to obtain a similar model using process data alone. Finally, as previously mentioned, the use of the metabolic condition variables in the characterisation of the process enable to pursue scale-up and regulatory filings in parallel (as a product specification can be characterised in terms of metabolic condition instead of solely in terms of process condition), as well as adjustment of process parameters between scales without re-characterising the process, by ensuring that the internal state (metabolic condition) is maintained.

EQUIVALENTS AND SCOPE

All documents mentioned in this specification are incorporated herein by reference in their entirety.

The terms "computer system" includes the hardware, software and data storage devices for embodying a system or carrying out a method according to the above described embodiments. For example, a computer system may comprise a central processing unit (CPU), input means, output means and data storage, which may be embodied as one or more connected computing devices. Preferably the computer system has a display or comprises a computing device that has a display to provide a visual output display (for example in the design of the business process). The data storage may comprise RAM, disk drives or other computer readable media. The computer system may include a plurality of computing devices connected by a network and able to communicate with each other over that network.

The methods of the above embodiments may be provided as computer programs or as computer program products or computer readable media carrying a computer program which is arranged, when run on a computer, to perform the method(s) described above.

The term "computer readable media" includes, without limitation, any non-transitory medium or media which can be read and accessed directly by a computer or computer system. The media can include, but are not limited to, magnetic storage media such as floppy discs, hard disc storage media and magnetic tape; optical storage media such as optical discs or CD-ROMs; electrical storage media such as memory, including RAM, ROM and flash memory; and hybrids and combinations of the above such as magnetic/optical storage media.

Unless context dictates otherwise, the descriptions and definitions of the features set out above are not limited to any particular aspect or embodiment of the invention and apply equally to all aspects and embodiments which are described.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about" or "approximately", it will be understood that the particular value forms another embodiment. The terms "about" or "approximately" in relation to a numerical value is optional and means for example+/−10%.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

Other aspects and embodiments of the invention provide the aspects and embodiments described above with the term "comprising" replaced by the term "consisting of" or "consisting essentially of", unless the context dictates otherwise.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

The invention claimed is:

1. A computer implemented method for monitoring a bioprocess comprising a cell culture in a bioreactor, the method including:

obtaining measurements of an amount of biomass and an amount of one or more metabolites in the bioreactor as a function of bioprocess maturity;

determining one or more metabolic condition variables selected from: specific transport rates between cells and a culture medium in the bioreactor for some or all of the one or more metabolites as a function of bioprocess maturity, internal concentration of one or more metabolites as a function of bioprocess maturity, and reaction rates for one or more metabolic reactions that form part of a metabolism of the cells as a function of bioprocess maturity;

using a pre-trained multivariate model to determine one or more values of one or more latent variables as a function of bioprocess maturity, wherein the pre-trained multivariate model is a linear model that uses process variables including the metabolic condition variables as predictor variables;

comparing the one or more values of the one or more latent variables to one or more predetermined values as a function of maturity; and determining, based on results of the comparing, whether the bioprocess is operating normally.

2. The method of claim 1, wherein determining one or more metabolic condition variables comprises determining the specific transport rate of the one or more metabolites between the cells and the culture medium, wherein the specific transport rate of a metabolite i is an amount of the metabolite i transported between the cells and the culture medium, per cell and per unit of maturity, optionally wherein the specific transport rate of the metabolite i at a particular maturity m is determined using equation (7):

[total change of metabolite amount in reactor]=[total flow of metabolite into reactor]−[total flow of metabolite out of reactor]+[secretion of metabolite by cells in reactor]−[consumption of metabolite by cells in reactor] (7).

3. The method of claim 2, wherein the specific transport rate of a metabolite is a specific consumption rate or a specific production rate.

4. The method of claim 1, wherein measurements of the amount of biomass in the bioreactor comprise measurements of viable cell density, and/or wherein the cell culture comprises cells cultured in a culture medium, and measurements of the amount of one or more metabolites in the bioreactor comprise measurements of the amount or concentration of one or more metabolites in the cells, in the culture medium, or in the cell culture as a whole.

5. The method of claim 1, wherein determining one or more metabolic condition variables comprises determining reaction rates for one or more metabolic reactions that form part of the metabolism of the cells in the culture as a function of bioprocess maturity.

6. The method of claim 5, wherein determining reaction rates for one or more metabolic reactions comprises obtaining a metabolic model comprising said reactions and solving the metabolic model using at least the specific transport rate of the one or more metabolites as constraints of the metabolic model.

7. The method of claim 6, wherein a metabolic model comprises a stoichiometric matrix S and a set of reaction rates v and solving the metabolic model comprises determining reaction rates y that satisfy:

$$\text{maximize}/minimise\ Z(x) = \Sigma_k \alpha_k * x_k^{\beta_k} \quad (3)$$

$$\text{subject to } S * v = \frac{dmet}{dt} \quad (4)$$

$$\forall\, i, \text{ lower bound}_i \leq v_i \quad (5a)$$

$$\forall\, j, v_j \leq \text{upper bound}_j \quad (5b)$$

where x are k variables that contribute to a cell goal expressed as objective function Z, α and β are coefficients that describe impact of x on the objective function Z, $$\frac{dmet}{dt}$$

is a rate of change of internal concentration of the metabolites in the metabolic model, i and j are indices of sets of reaction rates in the metabolic model for which a lower bound and an upper bound, respectively, are available, wherein at least one lower bound and/or upper bound value is a predetermined function of a specific transport rate of one of the one or more metabolites.

8. The method of claim 6, wherein using the specific transport rate of the one or more metabolites as constraints of the metabolic model comprises specifying an allowable range of values for at least one of the metabolic reaction rates as a function of at least one of the specific transport rates.

9. The method of claim 1, wherein determining or obtaining measurements of any variable as a function of maturity comprises determining or obtaining measurements of the variable as a function of time.

10. The method of claim 1, wherein the multivariate model is a linear model that uses process variables including the metabolic condition variables as predictor variables and maturity as a response variable and/or wherein the multivariate model has been pre-trained using data from a plurality of bioprocesses considered to operate normally, and that use the same cells as cells used in the cell culture in the bioreactor for biomanufacturing of the same product.

11. The method of claim 10, wherein the method further comprises predicting an effect of a change in one or more process conditions of the bioprocess on the one or more latent variables and/or the one or more metabolic condition variables.

12. The method of claim 10, wherein at least some of the data for the plurality of bioprocesses used to train the multivariate model are associated with one or more critical quality attributes (CQAs), and wherein the method further comprises using the values of one or more process variables including one or more metabolic condition variables and a model trained using the values of the one or more metabolic condition variables for the plurality of bioprocesses and corresponding CQAs to predict one or more CQAs of the bioprocess.

13. The method of claim 1, further comprising:

merging multiple measurements and/or metabolic condition variables into a single table where the measurements and/or metabolic condition variables are aligned by maturity;

subsampling or binning at least some of the measurements and/or metabolic condition variables; and smoothing and/or supersampling at least some of the measurements and/or metabolic condition variables.

14. A system for monitoring and/or controlling a bioprocess, the system including:

at least one processor; and at least one non-transitory computer readable medium containing instructions that, when executed by the at least one processor, cause the at least one processor to perform:

obtaining measurements of an amount of biomass and an amount of one or more metabolites in a bioreactor as a function of bioprocess maturity;

determining one or more metabolic condition variables selected from: specific transport rates between cells and a culture medium in the bioreactor for some or all of the one or more metabolites as a function of bioprocess maturity, internal concentration of one or more metabolites as a function of bioprocess maturity, and reaction rates for one or more metabolic reactions that form part of a metabolism of the cells as a function of bioprocess maturity;

using a pre-trained multivariate model to determine one or more values of one or more latent variables as a function of bioprocess maturity, wherein the pre-trained multivariate model is a linear model that uses process variables including the metabolic condition variables as predictor variables;

comparing the one or more values of the one or more latent variables to one or more predetermined values as a function of maturity; and determining, based on results of the comparing, whether the bioprocess is operating normally.

15. The system of claim 14, wherein the system further comprises, in operable connection with the processor, one or more of:

a user interface, wherein the instructions further cause the processor to provide, to the user interface for outputting to a user, one or more of: the value of the one or more latent variables as a function of bioprocess maturity, the one or more predetermined values as a function of maturity, results of the comparing, and a signal indicating that the bioprocess has been determined to operate normally or to not operate normally;

one or more biomass sensor(s);

one or more metabolite sensor(s);

one or more process condition sensors; and one or more effector device(s).

16. The method of claim 10, wherein the multivariate model has been pre-trained using data from a plurality of similar bioprocesses in which at least some of the bioprocesses differ from each other by one or more process conditions as a function of maturity.

17. The method of claim 8, wherein using the specific transport rate of a metabolite i as a constraint of the metabolic model comprises specifying:

$$\text{lower bound}_i = f_{low,i}(q\text{Met}_i) \leq v_{Exchange,i} \leq \text{upperbound}_i = f_{up,i}(q\text{Met}_i) \quad (10)$$

where $q\text{Met}_i$ is the specific transport rate of metabolite i, $f_{low,i}$ is a first function, $f_{up,i}$ is a second function, and $v_{Exchange,i}$ is the rate of a reaction in the metabolic model that captures consumption or secretion of the metabolite i by the cell.

18. The method of claim 7, wherein determining reaction rates for one or more metabolic reactions is performed using a flux balance analysis approach.

19. The method of claim 5, wherein the reaction rates for the one or more metabolic reactions are determined at least in part using the specific transport rate of the one or more metabolites between the cells and a culture medium in the bioreactor as a function of bioprocess maturity.

* * * * *